(12) United States Patent
Hosoi et al.

(10) Patent No.: US 11,031,123 B2
(45) Date of Patent: Jun. 8, 2021

(54) ENDOSCOPIC EXAMINATION WORK SUPPORT SYSTEM

(71) Applicant: OLYMPUS CORPORATION, Tokyo (JP)

(72) Inventors: Takaharu Hosoi, Tokyo (JP); Hirokazu Nishimura, Tokyo (JP); Yasushi Okoshi, Tokyo (JP); Kohei Yada, Tokyo (JP); Katsuyoshi Ishibashi, Tokyo (JP); Toshiro Baba, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 257 days.

(21) Appl. No.: 15/617,121

(22) Filed: Jun. 8, 2017

(65) Prior Publication Data

US 2017/0270259 A1 Sep. 21, 2017

Related U.S. Application Data

(63) Continuation of application No. PCT/JP2015/083083, filed on Nov. 25, 2015.

(30) Foreign Application Priority Data

Dec. 12, 2014 (JP) .............................. JP2014-252314

(51) Int. Cl.
*G16H 40/20* (2018.01)
*G16H 40/40* (2018.01)
(Continued)

(52) U.S. Cl.
CPC .............. *G16H 40/20* (2018.01); *A61B 1/12* (2013.01); *G06Q 10/109* (2013.01); *G16H 40/40* (2018.01)

(58) Field of Classification Search
CPC ........ G16H 40/20; G16H 40/40; G06Q 50/22; G06Q 10/04; G06Q 10/109
(Continued)

(56) References Cited

U.S. PATENT DOCUMENTS 5,830,121 A * 11/1998 Enomoto ........... A61B 1/00059
600/117
6,436,032 B1 8/2002 Eto et al.
(Continued)

FOREIGN PATENT DOCUMENTS

CN 102203820 A 9/2011
JP H09-136109 A 5/1997
(Continued)

OTHER PUBLICATIONS

International Search Report dated Dec. 28, 2015 issued in PCT/JP2015/083083.
(Continued)

*Primary Examiner* — Hiep V Nguyen
(74) *Attorney, Agent, or Firm* — Scully, Scott, Murphy & Presser, P.C.

(57) ABSTRACT

An examination schedule management unit manages an examination schedule of a plurality of endoscopic examinations, including an examination room, information on scheduled examination start time, that on scheduled examination end time, and examination type information on examination contents. A cleaning schedule management unit manages a cleaning schedule of a plurality of endoscopes, including a cleaning machine, information on scheduled cleaning start time, and that on scheduled cleaning end time. An endoscope assignment unit assigns an endoscope to an endoscopic examination. A cleaning machine assignment unit assigns a cleaning machine for cleaning an endoscope assigned to the endoscopic examination.

13 Claims, 40 Drawing Sheets

(51) Int. Cl.
  *G06Q 10/10* (2012.01)
  *A61B 1/12* (2006.01)
(58) Field of Classification Search
  USPC .............................................................. 705/2
  See application file for complete search history.

(56) References Cited

U.S. PATENT DOCUMENTS

| | | | | |
|---|---|---|---|---|
| 2005/0171814 | A1* | 8/2005 | Kobayashi | G06Q 50/22 |
| | | | | 705/2 |
| 2010/0030573 | A1* | 2/2010 | Araki | G06Q 10/087 |
| | | | | 705/2 |
| 2010/0268545 | A1* | 10/2010 | Inaba | G06Q 10/04 |
| | | | | 705/2 |

FOREIGN PATENT DOCUMENTS

| | | |
|---|---|---|
| JP | 2001-046326 A | 2/2001 |
| JP | 2003-328576 A | 11/2003 |
| JP | 2004-344216 A | 12/2004 |
| JP | 2008-117382 A | 5/2008 |
| JP | 2008-282403 A | 11/2008 |
| JP | 2009-095502 A | 5/2009 |
| JP | 2010-039560 A | 2/2010 |
| JP | 2012-164285 A | 8/2012 |
| JP | 2015-195867 A | 11/2015 |
| WO | WO 2010/047081 A1 | 4/2010 |

OTHER PUBLICATIONS

English translation of International Preliminary Report on Patentability dated Jun. 13, 2017 together with the Written Opinion in related International Application No. PCT/JP2015/083083.
Extended Supplementary European Search Report dated Aug. 7, 2018 in European Patent Application No. 15 86 7461.4.
Japanese Office Action dated Jul. 7, 2016 in JP 2016-536267.
Chinese Office Action dated Mar. 31, 2020 in Chinese Patent Application No. 201580065993.3.
Office Action dated Oct. 28, 2020 in Chinese Patent Application No. 201580065993.3.
Chinese Office Action dated Jul. 20, 2020 in Chinese Patent Application No. 201580065993.3.

\* cited by examiner

FIG. 4

(EXAMINATION SCHEDULE)

| | FIRST EXAMINATION ROOM | SECOND EXAMINATION ROOM | THIRD EXAMINATION ROOM | FOURTH EXAMINATION ROOM |
|---|---|---|---|---|
| 9:00 | UPPER ROUTINE DR. B E1 | UPPER ROUTINE DR. C E2 | UPPER ROUTINE DR. E E3 | LOWER ROUTINE DR. D E4 |
| 9:15 | UPPER ROUTINE DR. A E5 | UPPER ROUTINE DR. B E6 | UPPER ROUTINE DR. E E7 | LOWER ROUTINE DR. C E8 |
| 9:30 | UPPER NASAL DR. A E9 | UPPER SCRUTINY DR. B E10 | UPPER ROUTINE DR. D E11 | |
| 9:45 | | UPPER ROUTINE DR. B E15 | UPPER ROUTINE DR. D E13 | LOWER ROUTINE DR. E E12 |
| 10:00 | UPPER ROUTINE DR. A E14 | UPPER ROUTINE DR. E E18 | UPPER ROUTINE DR. D E16 | |
| 10:15 | UPPER SCRUTINY DR. C E17 | UPPER ROUTINE DR. E E21 | UPPER NASAL DR. B E20 | LOWER ROUTINE DR. A E19 |
| 10:30 | UPPER ROUTINE DR. C E22 | UPPER ROUTINE DR. E E24 | UPPER ROUTINE DR. B E25 | LOWER ROUTINE DR. D E23 |
| 10:45 | UPPER ROUTINE DR. A E26 | UPPER ROUTINE DR. E E28 | UPPER ROUTINE DR. B E29 | |
| 11:00 | UPPER ROUTINE DR. A E30 | UPPER SCRUTINY DR. B E31 | UPPER SCRUTINY DR. D E32 | LOWER SCRUTINY DR. C E27 |
| 11:15 | UPPER ROUTINE DR. A E33 | UPPER ROUTINE DR. B E36 | UPPER ROUTINE DR. D E37 | LOWER ROUTINE DR. E E34 |
| 11:30 | UPPER ROUTINE DR. C E35 | UPPER ROUTINE DR. B E39 | UPPER ROUTINE DR. D E40 | |
| 11:45 | UPPER ROUTINE DR. E E38 | | | LOWER SCRUTINY DR. A E41 |

FIG. 5

| EXAMINATION TYPE NO. | EXAMINATION TYPE NAME | EXAMINATION SCHEDULE TIME (MINUTE) |
|---|---|---|
| 1 | UPPER ROUTINE | 10 |
| 2 | UPPER NASAL | 15 |
| 3 | UPPER SCRUTINY | 15 |
| 4 | UPPER TREATMENT A, RELATIVELY SHORT | 30 |
| 5 | UPPER TREATMENT B, RELATIVELY LONG | 60 |
| 6 | UPPER TREATMENT, STOMACH ESD | 80 |
| 7 | UPPER TREATMENT, ESOPHAGUS ESD | — |
| 8 | UPPER EMERGENCY | — |
| 9 | LOWER ROUTINE | 15 |
| 10 | LOWER CHECKUP | 10 |
| 11 | LOWER SCRUTINY (INCLUDING IBD, ETC.) | 25 |
| 12 | LOWER TREATMENT A, RELATIVELY SHORT | 30 |
| 13 | LOWER TREATMENT B, RELATIVELY LONG | 80 |
| 14 | LOWER TREATMENT, LARGE INTESTINE ESD | 100 |
| 15 | LOWER EMERGENCY | — |
| 16 | LOWER ROUTINE (EXPERIENCE 3 YEARS) | 20 |

| ENDOSCOPE NO. | MODEL NAME | INDIVIDUAL NAME |
|---|---|---|
| 1 | UPPER ROUTINE MODEL | G-R-1 |
| 2 | UPPER ROUTINE MODEL | G-R-2 |
| 3 | UPPER ROUTINE MODEL | G-R-3 |
| 4 | UPPER ROUTINE MODEL | G-R-4 |
| 5 | UPPER ROUTINE MODEL | G-R-5 |
| 6 | UPPER ROUTINE MODEL | G-R-6 |
| 7 | UPPER HIGH IMAGE QUALITY MODEL | G-H-1 |
| 8 | UPPER HIGH IMAGE QUALITY MODEL | G-H-2 |
| 9 | UPPER HIGH IMAGE QUALITY MODEL | G-H-3 |
| 10 | UPPER NASAL MODEL | G-N-1 |
| 11 | UPPER EXPANSION MODEL | G-Z-1 |
| 12 | UPPER EXPANSION MODEL | G-Z-2 |
| 13 | UPPER TREATMENT MODEL | G-T-1 |
| 14 | UPPER TREATMENT MODEL | G-T-2 |
| 15 | LOWER ROUTINE MODEL | C-R-1 |
| 16 | LOWER ROUTINE MODEL | C-R-2 |
| 17 | LOWER ROUTINE MODEL | C-R-3 |
| 18 | LOWER EXPANSION MODEL | C-Z-1 |
| 19 | LOWER TREATMENT MODEL | C-T-1 |

(EXAMINATION SCHEDULE)

| | FIRST EXAMINATION ROOM | SECOND EXAMINATION ROOM | THIRD EXAMINATION ROOM | FOURTH EXAMINATION ROOM |
|---|---|---|---|---|
| 9:00 | UPPER ROUTINE DR. B E1 G-R-1 | UPPER ROUTINE DR. C E2 G-R-2 | UPPER ROUTINE DR. E E3 G-R-3 | LOWER ROUTINE DR. D E4 C-R-1 |
| 9:15 | UPPER ROUTINE DR. A E5 | UPPER ROUTINE DR. B E6 | UPPER ROUTINE DR. E E7 | LOWER ROUTINE DR. C E8 |
| 9:30 | UPPER NASAL DR. A E9 | UPPER SCRUTINY DR. B E10 | UPPER ROUTINE DR. D E11 | |
| 9:45 | | | | LOWER ROUTINE DR. E E12 |
| | | UPPER ROUTINE DR. B E15 | UPPER ROUTINE DR. D E13 | |
| 10:00 | UPPER ROUTINE DR. A E14 | UPPER ROUTINE DR. E E18 | UPPER ROUTINE DR. D E16 | LOWER ROUTINE DR. A E19 |
| 10:15 | UPPER SCRUTINY DR. C E17 | UPPER ROUTINE DR. E E21 | UPPER NASAL DR. B E20 | |
| 10:30 | UPPER ROUTINE DR. C E22 | UPPER ROUTINE DR. E E24 | UPPER ROUTINE DR. B E25 | LOWER ROUTINE DR. D E23 |
| 10:45 | UPPER ROUTINE DR. A E26 | UPPER ROUTINE DR. E E28 | UPPER ROUTINE DR. B E29 | LOWER SCRUTINY DR. C E27 |
| 11:00 | UPPER ROUTINE DR. A E30 | UPPER SCRUTINY DR. B E31 | UPPER SCRUTINY DR. D E32 | |
| 11:15 | UPPER ROUTINE DR. C E33 | UPPER ROUTINE DR. B E35 | UPPER ROUTINE DR. D E36 | LOWER ROUTINE DR. E E34 |
| 11:30 | UPPER ROUTINE DR. E E38 | UPPER ROUTINE DR. B E39 | UPPER ROUTINE DR. D E37 | |
| 11:45 | | | UPPER ROUTINE DR. D E40 | LOWER SCRUTINY DR. A E41 |

| ENDOSCOPE NO. | INDIVIDUAL NAME | 9:00 | | | | | | 10:00 | | | | | | | | | | | | 11:00 | | | | | | | | | | | | 12:00 | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| | | 0 | 5 | 10 | 15 | 20 | 25 | 30 | 35 | 40 | 45 | 50 | 55 | 0 | 5 | 10 | 15 | 20 | 25 | 30 | 35 | 40 | 45 | 50 | 55 | 0 | 5 | 10 | 15 | 20 | 25 | 30 | 35 | 40 | 45 | | | | |
| 1 | G-R-1 | E1 | | C1 | | | | | | | | | | | | | | | | | | | | | | | | | | | | | | | | | | | | |
| 2 | G-R-2 | E2 | | C2 | | | | | | | | | | | | | | | | | | | | | | | | | | | | | | | | | | | | |
| 3 | G-R-3 | E3 | | C3 | | | | | | | | | | | | | | | | | | | | | | | | | | | | | | | | | | | | |
| 4 | G-R-4 | | | | | | | | | | | | | | | | | | | | | | | | | | | | | | | | | | | | | | | |
| 5 | G-R-5 | | | | | | | | | | | | | | | | | | | | | | | | | | | | | | | | | | | | | | | |
| 6 | G-R-6 | | | | | | | | | | | | | | | | | | | | | | | | | | | | | | | | | | | | | | | |
| 7 | G-H-1 | | | | | | | | | | | | | | | | | | | | | | | | | | | | | | | | | | | | | | | |
| 8 | G-H-2 | | | | | | | | | | | | | | | | | | | | | | | | | | | | | | | | | | | | | | | |
| 9 | G-H-3 | | | | | | | | | | | | | | | | | | | | | | | | | | | | | | | | | | | | | | | |
| 10 | G-N-1 | | | | | | | | | | | | | | | | | | | | | | | | | | | | | | | | | | | | | | | |
| 11 | G-Z-1 | | | | | | | | | | | | | | | | | | | | | | | | | | | | | | | | | | | | | | | |
| 12 | G-Z-2 | | | | | | | | | | | | | | | | | | | | | | | | | | | | | | | | | | | | | | | |
| 13 | G-T-1 | | | | | | | | | | | | | | | | | | | | | | | | | | | | | | | | | | | | | | | |
| 14 | G-T-2 | | | | | | | | | | | | | | | | | | | | | | | | | | | | | | | | | | | | | | | |
| 15 | C-R-1 | E4 | | C4 | | | | | | | | | | | | | | | | | | | | | | | | | | | | | | | | | | | |
| 16 | C-R-2 | | | | | | | | | | | | | | | | | | | | | | | | | | | | | | | | | | | | | | | |
| 17 | C-R-3 | | | | | | | | | | | | | | | | | | | | | | | | | | | | | | | | | | | | | | | |
| 18 | C-Z-1 | | | | | | | | | | | | | | | | | | | | | | | | | | | | | | | | | | | | | | | |
| 19 | C-T-1 | | | | | | | | | | | | | | | | | | | | | | | | | | | | | | | | | | | | | | | |

(EXAMINATION SCHEDULE)

| | FIRST EXAMINATION ROOM | SECOND EXAMINATION ROOM | THIRD EXAMINATION ROOM | FOURTH EXAMINATION ROOM |
|---|---|---|---|---|
| 9:00 | UPPER ROUTINE DR. B E1 G-R-1 | UPPER ROUTINE DR. C E2 G-R-2 | UPPER ROUTINE DR. E E3 G-R-3 | LOWER ROUTINE DR. D E4 C-R-1 |
| 9:15 | UPPER ROUTINE DR. A E5 G-R-4 | UPPER ROUTINE DR. B E6 G-R-5 | UPPER ROUTINE DR. E E7 G-R-6 | LOWER ROUTINE DR. C E8 C-R-2 |
| 9:30 | UPPER NASAL DR. A E9 G-R-1 | UPPER SCRUTINY DR. B E10 G-R-2 | UPPER ROUTINE DR. D E11 G-R-3 | LOWER ROUTINE DR. E E12 |
| 9:45 | UPPER ROUTINE DR. A E14 G-R-4 | UPPER ROUTINE DR. B E15 G-R-5 | UPPER ROUTINE DR. D E13 G-H-1 | LOWER ROUTINE DR. E C-R-1 |
| 10:00 | UPPER SCRUTINY DR. C E17 | UPPER ROUTINE DR. E E18 | UPPER ROUTINE DR. B E16 | LOWER ROUTINE DR. A E19 |
| 10:15 | UPPER ROUTINE DR. C E22 | UPPER ROUTINE DR. E E21 | UPPER NASAL DR. B E20 | |
| 10:30 | UPPER ROUTINE DR. A E26 | UPPER ROUTINE DR. E E24 | UPPER ROUTINE DR. B E25 | LOWER ROUTINE DR. D E23 |
| 10:45 | UPPER ROUTINE DR. A E30 | UPPER ROUTINE DR. E E28 | UPPER ROUTINE DR. B E29 | LOWER SCRUTINY DR. C E27 |
| 11:00 | UPPER ROUTINE DR. A E33 | UPPER SCRUTINY DR. B E31 | UPPER SCRUTINY DR. D E32 | |
| 11:15 | UPPER ROUTINE DR. C E35 | UPPER ROUTINE DR. B E36 | UPPER ROUTINE DR. D E37 | LOWER ROUTINE DR. E E34 |
| 11:30 | UPPER ROUTINE DR. E E38 | UPPER ROUTINE DR. B E39 | UPPER ROUTINE DR. D E40 | LOWER SCRUTINY DR. A E41 |
| 11:45 | | | | |

(CLEANING SCHEDULE)

| | FIRST CLEANING MACHINE | SECOND CLEANING MACHINE | THIRD CLEANING MACHINE | FOURTH CLEANING MACHINE |
|---|---|---|---|---|
| 9:00 | | | | |
| 9:15 | G-R-1 | G-R-2 | G-R-3 | C-R-1 |
| 9:30 | G-R-4 | G-R-5 | G-R-6 | C-R-2 |
| 9:45 | G-R-1 | G-R-2 | G-R-3 | G-H-1 |
| 10:00 | C-R-1 | G-R-4 | G-R-5 | |
| 10:15 | | | | |

FIG. 19

| ENDOSCOPE NO. | INDIVIDUAL NAME | 9:00 | | | | | | | | | | | 10:00 | | | | | | | | | | | 11:00 | | | | | | | | | | | | 12:00 | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | 0 | 5 | 10 | 15 | 20 | 25 | 30 | 35 | 40 | 45 | 50 | 55 | 0 | 5 | 10 | 15 | 20 | 25 | 30 | 35 | 40 | 45 | 50 | 55 | 0 | 5 | 10 | 15 | 20 | 25 | 30 | 35 | 40 | 45 | 50 | 55 | 0 | 5 | 10 | 15 | 20 | 25 | 30 | 35 | 40 | 45 |
| 1 | G-R-1 | E1 | | C1 | | | | | | | | | | | | | | | | | | | | | | | | | | | | | | | | | | | | | | | | | |
| 2 | G-R-2 | E2 | | | C2 | | | | | | | | | | | | | | | | | | | | | | | | | | | | | | | | | | | | | | | | |
| 3 | G-R-3 | E3 | | | | C3 | | | | | | | | | | | | | | | | | | | | | | | | | | | | | | | | | | | | | | | |
| 4 | G-R-4 | | | | | | E5 | | E9 | | C1 | | | | C2 | C3 | | | | | | | | | | | | | | | | | | | | | | | | | | | | | |
| 5 | G-R-5 | | | | | | | E6 | | E10 | | C2 | | | | | | | | | | | | | | | | | | | | | | | | | | | | | | | | | |
| 6 | G-R-6 | | | | | | | E7 | | E11 | | C3 | | | | | | | | | | | | | | | | | | | | | | | | | | | | | | | | | |
| 7 | G-H-1 | | | | | | | | | | E14 | | | | | | | | | | | | | | | | | | | | | | | | | | | | | | | | | | |
| 8 | G-H-2 | | | | | | | | | | | E15 | | | | | | | | | | | | | | | | | | | | | | | | | | | | | | | | | |
| 9 | G-H-3 | | | | | | | | | | | | E13 | | C4 | | | | | | | | | | | | | | | | | | | | | | | | | | | | | | |
| 10 | G-N-1 | | | | | | | | | | | | | | | | | | | | | | | | | | | | | | | | | | | | | | | | | | | | |
| 11 | G-Z-1 | | | | | | | | | | | | | | | | | | | | | | | | | | | | | | | | | | | | | | | | | | | | |
| 12 | G-Z-2 | | | | | | | | | | | | | | | | | | | | | | | | | | | | | | | | | | | | | | | | | | | | |
| 13 | G-T-1 | | | | | | | | | | | | | | | | | | | | | | | | | | | | | | | | | | | | | | | | | | | | |
| 14 | G-T-2 | | | | | | | | | | | | | | | | | | | | | | | | | | | | | | | | | | | | | | | | | | | | |
| 15 | C-R-1 | E4 | | | | | C4 | | | | | | E12 | | | | | | | | | | | | | | | | | | | | | | | | | | | | | | | | |
| 16 | C-R-2 | | | | | | | E8 | | | | | | C4 | | | | | | | | | | | | | | | | | | | | | | | | | | | | | | | |
| 17 | C-R-3 | | | | | | | | | | | | | | | | C1 | | | | | | | | | | | | | | | | | | | | | | | | | | | | |
| 18 | C-Z-1 | | | | | | | | | | | | | | | | | | | | | | | | | | | | | | | | | | | | | | | | | | | | |
| 19 | C-T-1 | | | | | | | | | | | | | | | | | | | | | | | | | | | | | | | | | | | | | | | | | | | | |

FIG. 20

(EXAMINATION SCHEDULE)

| | FIRST EXAMINATION ROOM | SECOND EXAMINATION ROOM | THIRD EXAMINATION ROOM | FOURTH EXAMINATION ROOM |
|---|---|---|---|---|
| 9:00 | UPPER ROUTINE DR. B E1<br>G-R-1 | UPPER ROUTINE DR. C E2<br>G-R-2 | UPPER ROUTINE DR. E E3<br>G-R-3 | LOWER ROUTINE DR. D E4<br>C-R-1 |
| 9:15 | UPPER ROUTINE DR. A E5<br>G-R-4 | UPPER ROUTINE DR. B E6<br>G-R-5 | UPPER ROUTINE DR. E E7<br>G-R-6 | LOWER ROUTINE DR. C E8<br>C-R-2 |
| 9:30 | UPPER NASAL DR. A E9<br>G-R-1 | UPPER SCRUTINY DR. B E10<br>G-R-2 | UPPER ROUTINE DR. D E11<br>G-R-3 | LOWER ROUTINE DR. E E12<br>C-R-1 |
| 9:45 | UPPER ROUTINE DR. A E14<br>G-R-4 | UPPER ROUTINE DR. B E15<br>G-R-5 | UPPER ROUTINE DR. D E13<br>G-H-1 | |
| 10:00 | UPPER SCRUTINY DR. C E17<br>G-H-2 | UPPER ROUTINE DR. E E18<br>G-H-3 | UPPER ROUTINE DR. D E16<br>G-R-6 | LOWER ROUTINE DR. A E19<br>C-R-2 |
| 10:15 | UPPER ROUTINE DR. C E22<br>G-R-3 | UPPER ROUTINE DR. E E21<br>G-R-2 | UPPER NASAL DR. B E20<br>G-R-1 | LOWER ROUTINE DR. D E23<br>G-R-3 |
| 10:30 | UPPER ROUTINE DR. A E26<br>G-R-6 | UPPER ROUTINE DR. E E24<br>G-R-4 | UPPER ROUTINE DR. B E25<br>G-R-5 | |
| 10:45 | UPPER ROUTINE DR. A E30<br>G-R-1 | UPPER ROUTINE DR. E E28<br>G-H-1 | UPPER ROUTINE DR. B E29<br>G-H-2 | LOWER SCRUTINY DR. C E27<br>C-R-1 |
| 11:00 | UPPER ROUTINE DR. A E33<br>G-R-2 | UPPER SCRUTINY DR. B E31<br>G-H-3 | UPPER SCRUTINY DR. D E32<br>G-N-1 | |
| 11:15 | UPPER ROUTINE DR. C E35<br>G-R-3 | UPPER ROUTINE DR. B E36<br>G-R-4 | UPPER ROUTINE DR. D E37<br>G-Z-1 | LOWER ROUTINE DR. E E34<br>C-R-2 |
| 11:30 | UPPER ROUTINE DR. E E38<br>G-R-5 | UPPER ROUTINE DR. B E39<br>G-R-6 | UPPER ROUTINE DR. D E40<br>G-H-1 | LOWER SCRUTINY DR. A E41<br>C-R-1 |
| 11:45 | | | | |

(CLEANING SCHEDULE)

| | FIRST CLEANING MACHINE | SECOND CLEANING MACHINE | THIRD CLEANING MACHINE | FOURTH CLEANING MACHINE |
|---|---|---|---|---|
| 9:00 | | | | |
| 9:15 | G-R-1 | G-R-2 | G-R-3 | G-R-1 |
| 9:30 | G-R-4 | G-R-5 | G-R-6 | C-R-2 |
| 9:45 | G-R-1 | G-R-2 | G-R-3 | G-H-1 |
| 10:00 | C-R-1 | G-R-4 | G-R-5 | G-R-6 |
| 10:15 | G-H-3 | G-H-2 | C-R-2 | G-R-1 |
| 10:30 | G-R-2 | G-R-3 | G-R-3 | G-R-4 |
| 10:45 | G-R-5 | G-R-6 | G-R-1 | G-H-1 |
| 11:00 | G-H-2 | G-R-1 | G-H-3 | G-N-1 |
| 11:15 | G-R-2 | G-R-2 | G-R-3 | G-R-4 |
| 11:30 | G-Z-1 | G-R-5 | G-R-6 | G-H-1 |
| 11:45 | G-R-1 | | | |
| 12:00 | | | | |
| 12:15 | | | | |
| 12:30 | | | | |

| EXAMINATION TYPE NO. | EXAMINATION TYPE NAME | PREFERENTIAL ENDOSCOPE MODEL 1 | PREFERENTIAL ENDOSCOPE MODEL 2 |
|---|---|---|---|
| 1 | UPPER ROUTINE | UPPER ROUTINE MODEL | UPPER HIGH IMAGE QUALITY MODEL |
| 2 | UPPER NASAL | UPPER NASAL MODEL | - |
| 3 | UPPER SCRUTINY | UPPER HIGH IMAGE QUALITY MODEL | UPPER EXPANSION MODEL |
| 4 | UPPER TREATMENT A. RELATIVELY SHORT | UPPER TREATMENT MODEL | - |
| 5 | UPPER TREATMENT B. RELATIVELY LONG | UPPER TREATMENT MODEL | - |
| 6 | UPPER TREATMENT. STOMACH ESD | UPPER TREATMENT MODEL | - |
| 7 | UPPER TREATMENT. ESOPHAGUS ESD | UPPER TREATMENT MODEL | - |
| 8 | UPPER EMERGENCY | UPPER TREATMENT MODEL | UPPER HIGH IMAGE QUALITY MODEL |
| 9 | LOWER ROUTINE | LOWER ROUTINE MODEL | LOWER EXPANSION MODEL |
| 10 | LOWER CHECKUP | LOWER ROUTINE MODEL | LOWER EXPANSION MODEL |
| 11 | LOWER SCRUTINY (INCLUDING IBD, ETC.) | LOWER EXPANSION MODEL | LOWER ROUTINE MODEL |
| 12 | LOWER TREATMENT A. COMPARATIVELY SHORT | LOWER TREATMENT MODEL | - |
| 13 | LOWER TREATMENT B. RELATIVELY LONG | LOWER TREATMENT MODEL | - |
| 14 | LOWER TREATMENT. LARGE INTESTINE ESD | LOWER TREATMENT MODEL | - |
| 15 | LOWER EMERGENCY | LOWER TREATMENT MODEL | LOWER EXPANSION MODEL |

| ENDOSCOPE NO. | INDIVIDUAL NAME | NUMBER OF TIMES OF USE | HOUR OF USE (MINUTE) |
|---|---|---|---|
| 1 | G-R-1 | 100 | 1000 |
| 2 | G-R-2 | 50 | 500 |
| 3 | G-R-3 | 40 | 650 |
| 4 | G-R-4 | 50 | 600 |
| 5 | G-R-5 | 200 | 2000 |
| 6 | G-R-6 | 100 | 1000 |
| 7 | G-H-1 | 5 | 100 |
| 8 | G-H-2 | 12 | 240 |
| 9 | G-H-3 | 10 | 200 |
| 10 | G-N-1 | 30 | 300 |
| 11 | G-Z-1 | 100 | 2000 |
| 12 | G-Z-2 | 120 | 2400 |
| 13 | G-T-1 | 130 | 2600 |
| 14 | G-T-2 | 80 | 800 |
| 15 | C-R-1 | 40 | 800 |
| 16 | C-R-2 | 20 | 400 |
| 17 | C-R-3 | 50 | 1000 |
| 18 | C-Z-1 | 10 | 300 |
| 19 | C-T-1 | 5 | 100 |

| ENDOSCOPE NO. | INDIVIDUAL NAME | FIRST CLEANING MACHINE (MEDICINAL SOLUTION A) | SECOND CLEANING MACHINE (MEDICINAL SOLUTION A) | THIRD CLEANING MACHINE (MEDICINAL SOLUTION B) | FOURTH CLEANING MACHINE (MEDICINAL SOLUTION C) |
|---|---|---|---|---|---|
| 1 | G-R-1 |  | 1 | 2 | 0 |
| 2 | G-R-2 | 1 |  | 2 | 0 |
| 3 | G-R-3 |  | 1 | 2 | 0 |
| 4 | G-R-4 | 1 |  | 2 | 0 |
| 5 | G-R-5 |  | 1 | 2 | 0 |
| 6 | G-R-6 | 1 |  | 2 | 0 |
| 7 | G-H-1 |  | 1 | 2 | 0 |
| 8 | G-H-2 | 1 |  | 2 | 0 |
| 9 | G-H-3 |  | 1 | 1 | 0 |
| 10 | G-N-1 | 2 | 2 | 1 | 0 |
| 11 | G-Z-1 | 2 | 2 | 3 | 0 |
| 12 | G-Z-2 | 2 | 2 | 3 | 0 |
| 13 | G-T-1 | 1 | 1 | 2 | 2 |
| 14 | G-T-2 | 1 |  | 2 | 0 |
| 15 | C-R-1 |  | 1 | 2 | 0 |
| 16 | C-R-2 | 1 |  | 2 | 0 |
| 17 | C-R-3 |  | 1 | 1 | 0 |
| 18 | C-Z-1 | 2 | 2 | 3 | 2 |
| 19 | C-T-1 | 1 |  | 3 | 2 |

| DOCTOR NAME | MODEL NAME | PREFERENTIAL ENDOSCOPE 1 | PREFERENTIAL ENDOSCOPE 2 | PREFERENTIAL ENDOSCOPE 3 |
|---|---|---|---|---|
| DOCTOR A | UPPER ROUTINE MODEL | G-R-2 | G-R-1 | |
| DOCTOR A | UPPER HIGH IMAGE QUALITY MODEL | G-H-2 | | |
| DOCTOR A | LOWER ROUTINE MODEL | C-R-2 | C-R-1 | |
| DOCTOR B | UPPER ROUTINE MODEL | G-R-3 | G-R-1 | G-R-2 |
| DOCTOR B | UPPER HIGH IMAGE QUALITY MODEL | G-H-3 | G-H-1 | |
| DOCTOR B | LOWER ROUTINE MODEL | | | |
| DOCTOR C | UPPER ROUTINE MODEL | G-R-1 | G-R-5 | G-R-4 |
| DOCTOR C | UPPER HIGH IMAGE QUALITY MODEL | | | |
| DOCTOR C | LOWER ROUTINE MODEL | C-R-1 | | |
| DOCTOR D | UPPER ROUTINE MODEL | G-R-4 | G-R-6 | G-R-3 |
| DOCTOR D | UPPER HIGH IMAGE QUALITY MODEL | | | |
| DOCTOR D | LOWER ROUTINE MODEL | C-R-3 | | |
| DOCTOR E | UPPER ROUTINE MODEL | G-R-5 | G-R-6 | G-R-4 |
| DOCTOR E | UPPER HIGH IMAGE QUALITY MODEL | | | |
| DOCTOR E | LOWER ROUTINE MODEL | | | |

(EXAMINATION SCHEDULE)

| Time | FIRST EXAMINATION ROOM | SECOND EXAMINATION ROOM | THIRD EXAMINATION ROOM | FOURTH EXAMINATION ROOM |
|---|---|---|---|---|
| 9:00 | UPPER ROUTINE DR. B E1 G-R-3 | UPPER ROUTINE DR. C E2 G-R-1 | UPPER ROUTINE DR. E E3 G-R-5 | LOWER ROUTINE DR. D E4 G-R-3 |
| 9:15 | UPPER ROUTINE DR. A E5 | UPPER ROUTINE DR. B E6 | UPPER ROUTINE DR. E E7 | LOWER ROUTINE DR. C E8 |
| 9:30 | UPPER NASAL DR. A E9 | UPPER SCRUTINY DR. B E10 | UPPER ROUTINE DR. D E11 | |
| 9:45 | | | | LOWER ROUTINE DR. E E12 |
| 10:00 | UPPER ROUTINE DR. A E14 | UPPER ROUTINE DR. B E15 | UPPER ROUTINE DR. D E13 | |
| 10:15 | UPPER SCRUTINY DR. C E17 | UPPER ROUTINE DR. E E18 | UPPER ROUTINE DR. D E16 | LOWER ROUTINE DR. A E19 |
| 10:30 | UPPER ROUTINE DR. C E22 | UPPER ROUTINE DR. E E21 | UPPER NASAL DR. B E20 | |
| 10:45 | UPPER ROUTINE DR. A E26 | UPPER ROUTINE DR. E E24 | UPPER ROUTINE DR. B E25 | LOWER ROUTINE DR. D E23 |
| 11:00 | UPPER ROUTINE DR. A E30 | UPPER ROUTINE DR. E E28 | UPPER ROUTINE DR. B E29 | |
| 11:15 | UPPER ROUTINE DR. A E33 | UPPER SCRUTINY DR. B E31 | UPPER SCRUTINY DR. D E32 | LOWER SCRUTINY DR. C E27 |
| 11:30 | UPPER ROUTINE DR. C E35 | UPPER ROUTINE DR. B E36 | UPPER ROUTINE DR. D E37 | LOWER ROUTINE DR. E E34 |
| 11:45 | UPPER ROUTINE DR. E E38 | UPPER ROUTINE DR. B E39 | UPPER ROUTINE DR. D E40 | LOWER SCRUTINY DR. A E41 |

FIG. 33

DISPLAY PERIOD 2013/11/1~2014/10/30

NUMBER OF TIMES OF USE FOR EACH DOCTOR

| INDIVIDUAL NAME | MODEL NAME | DATE OF BEGINNING OF USE | DOCTOR A | DOCTOR B | DOCTOR C | DOCTOR D | DOCTOR E | TOTAL | NUMBER OF TIMES OF FAILURE |
|---|---|---|---|---|---|---|---|---|---|
| G-R-1 | UPPER ROUTINE MODEL | 2012/4/1 | 200 | 100 | 600 | 100 | 0 | 1000 | 5 |
| G-R-2 | UPPER ROUTINE MODEL | 2012/4/1 | 700 | 100 | 0 | 100 | 100 | 1000 | 4 |
| G-R-3 | UPPER ROUTINE MODEL | 2012/4/1 | 0 | 500 | 100 | 200 | 100 | 900 | 0 |
| G-R-4 | UPPER ROUTINE MODEL | 2012/4/1 | 0 | 100 | 100 | 600 | 100 | 900 | 0 |
| G-R-5 | UPPER ROUTINE MODEL | 2012/4/1 | 100 | 100 | 200 | 100 | 500 | 900 | 4 |
| G-R-6 | UPPER ROUTINE MODEL | 2012/4/1 | 100 | 100 | 100 | 300 | 300 | 900 | 1 |

| ENDOSCOPE NO. | INDIVIDUAL NAME | PREFERENTIAL PERSON IN CHARGE 1 | PREFERENTIAL PERSON IN CHARGE 2 |
|---|---|---|---|
| 1 | G-R-1 | TECHNICIAN A | TECHNICIAN B |
| 2 | G-R-2 | TECHNICIAN C | TECHNICIAN A |
| 3 | G-R-3 | TECHNICIAN B | TECHNICIAN C |
| 4 | G-R-4 | TECHNICIAN A | TECHNICIAN C |
| 5 | G-R-5 | TECHNICIAN C | TECHNICIAN B |
| 6 | G-R-6 | TECHNICIAN B | TECHNICIAN A |
| 7 | G-H-1 | TECHNICIAN A | TECHNICIAN B |
| 8 | G-H-2 | TECHNICIAN C | TECHNICIAN A |
| 9 | G-H-3 | TECHNICIAN B | TECHNICIAN C |
| 10 | G-N-1 | TECHNICIAN A | TECHNICIAN C |
| 11 | G-Z-1 | TECHNICIAN C | TECHNICIAN B |
| 12 | G-Z-2 | TECHNICIAN B | TECHNICIAN A |
| 13 | G-T-1 | TECHNICIAN A | TECHNICIAN B |
| 14 | G-T-2 | TECHNICIAN C | TECHNICIAN A |
| 15 | C-R-1 | TECHNICIAN B | TECHNICIAN C |
| 16 | C-R-2 | TECHNICIAN A | TECHNICIAN C |
| 17 | C-R-3 | TECHNICIAN C | TECHNICIAN B |
| 18 | C-Z-1 | TECHNICIAN B | TECHNICIAN A |
| 19 | C-T-1 | TECHNICIAN A | TECHNICIAN B |

(EXAMINATION SCHEDULE)

| | FIRST EXAMINATION ROOM | SECOND EXAMINATION ROOM | THIRD EXAMINATION ROOM | FOURTH EXAMINATION ROOM |
|---|---|---|---|---|
| 9:00 | UPPER ROUTINE DR. B E1 | UPPER ROUTINE DR. C E2 | UPPER ROUTINE DR. E E3 | LOWER ROUTINE DR. D E4 |
| 9:15 | UPPER ROUTINE DR. A E5 | UPPER ROUTINE DR. B E6 | UPPER ROUTINE DR. E E7 | LOWER ROUTINE DR. C E8 |
| 9:30 | UPPER NASAL DR. A E9 | UPPER SCRUTINY DR. B E10 | UPPER ROUTINE DR. D E11 | |
| 9:45 | | | | LOWER ROUTINE DR. E E12 |
| 10:00 | UPPER ROUTINE DR. A E14 | UPPER ROUTINE DR. B E15 | UPPER ROUTINE DR. D E13 | |
| | | | UPPER ROUTINE DR. D E16 | LOWER ROUTINE DR. A E19 |
| 10:15 | UPPER SCRUTINY DR. C E17 | UPPER ROUTINE DR. E E18 | UPPER NASAL DR. B E20 | |
| 10:30 | UPPER ROUTINE DR. C E22 | UPPER ROUTINE DR. E E21 | UPPER ROUTINE DR. B E25 | LOWER ROUTINE DR. D E23 |
| 10:45 | UPPER ROUTINE DR. A E26 | UPPER ROUTINE DR. E E24 | UPPER ROUTINE DR. B E29 | LOWER SCRUTINY DR. C E27 |
| 11:00 | UPPER ROUTINE DR. A E30 | UPPER ROUTINE DR. E E28 | UPPER SCRUTINY DR. B E32 | |
| 11:15 | UPPER ROUTINE DR. A E33 | UPPER SCRUTINY DR. B E31 | UPPER ROUTINE DR. D E37 | LOWER ROUTINE DR. E E34 |
| 11:30 | UPPER ROUTINE DR. C E35 | UPPER ROUTINE DR. B E36 | UPPER ROUTINE DR. D E40 | |
| 11:45 | UPPER ROUTINE DR. E E38 | UPPER ROUTINE DR. B E39 | | LOWER SCRUTINY DR. A E41 |

(CLEANING SCHEDULE)

| | FIRST CLEANING MACHINE | SECOND CLEANING MACHINE | THIRD CLEANING MACHINE | FOURTH CLEANING MACHINE |
|---|---|---|---|---|
| 9:00 | | | | |
| 9:15 | G-R-3 TECHNICIAN B | G-R-1 TECHNICIAN A | | |
| 9:30 | | | G-R-5 TECHNICIAN C | C-R-3 TECHNICIAN C |

FIG. 39

DISPLAY PERIOD 2013/11/1~2014/10/30

| INDIVIDUAL NAME | MODEL NAME | DATE OF BEGINNING OF USE | NUMBER OF TIMES OF CLEANING FOR EACH PERSON IN CHARGE | | | | NUMBER OF TIMES OF FAILURE |
|---|---|---|---|---|---|---|---|
| | | | TECHNICIAN A | TECHNICIAN B | TECHNICIAN C | TOTAL | |
| G-R-1 | UPPER ROUTINE MODEL | 2012/4/1 | 900 | 100 | 0 | 1000 | 5 |
| G-R-2 | UPPER ROUTINE MODEL | 2012/4/1 | 200 | 0 | 800 | 1000 | 4 |
| G-R-3 | UPPER ROUTINE MODEL | 2012/4/1 | 0 | 800 | 100 | 900 | 0 |
| G-R-4 | UPPER ROUTINE MODEL | 2012/4/1 | 800 | 0 | 100 | 900 | 0 |
| G-R-5 | UPPER ROUTINE MODEL | 2012/4/1 | 0 | 200 | 700 | 900 | 4 |
| G-R-6 | UPPER ROUTINE MODEL | 2012/4/1 | 100 | 700 | 100 | 900 | 1 |

12

ENDOSCOPIC EXAMINATION WORK SUPPORT SYSTEM

CROSS-REFERENCE TO RELATED APPLICATIONS

This application is a U.S. continuation application of PCT International Patent Application No. PCT/JP2015/083083, filed on Nov. 25, 2015, claiming the benefit of priority of Japanese Patent Application No. 2014-252314, filed on Dec. 12, 2014, the entire contents of which are incorporated herein by reference.

TECHNICAL FIELD

The present invention relates to a technique for supporting endoscopic examination work in which scheduling of endoscopes to be used in endoscopic examinations is performed.

BACKGROUND ART

The order of an endoscopic examination (hereinafter, also referred to as an "examination order") is generated in a hospital information system such as, for example, an ordering system, and is issued to an endoscopy department system. The examination order includes order information on an endoscopic examination, such as scheduled examination start time and examination end time, patient identification information (patient ID), examination type, primary doctor of examination, and examination room.

An examination schedule for one day in an endoscopy department is generated by a plurality of examination orders, but cleaning processing of an endoscope to be used (hereinafter, also referred to as an "endoscope" or simply as a "scope") and a used endoscope is not included in an examination order. It is left to the determination on the spot which endoscope is to be used in an examination or which cleaning machine is to be used for the cleaning of a used endoscope. For example, a doctor instructs, immediately before an examination, a person preparing for examination, such as a technician or a nurse, to bring an endoscope to be used into an examination room by orally giving him/her information on the model of the endoscope. Alternatively, a person preparing for examination voluntarily brings an endoscope into an examination room by confirming an examination to be performed from now from an examination schedule table. Used endoscopes are brought into a cleaning room by persons preparing for examination, and ideally a person preparing for examination cleans the endoscopes in descending order of priority in consideration of the subsequent examination schedule.

Patent Document 1 discloses a technique for determining whether endoscopes to be used in each examination are insufficient according to examination start time specified by an examination schedule and scheduled cleaning end times specified by a cleaning schedule.

RELATED ART DOCUMENT

Patent Document

[PATENT DOCUMENT 1] Japanese Patent Application Publication No. 2010-39560

DISCLOSURE OF THE INVENTION

Problem to be Solved by the Invention

A medical facility where numerous endoscopic examinations are performed possesses various models of endoscopes and possesses multiple individuals of a frequently used model. In the medical facility where there are many endoscopes, as described above, a person preparing for examination cannot easily understand which endoscope should be brought into an examination room, and hence it takes time for preparation or determination. When a person preparing for examination brings an endoscope under an instruction from a doctor, the work is initiated after the instruction is received, and hence it takes extra time.

Because such a medical facility has a plurality of endoscope cleaning machines, it is also necessary to confirm the state of each cleaning machine each time. In a large hospital or an endoscopy center, a preparation time between examinations is only about several minutes, and hence there is a challenge for improving work efficiency or labor saving, but in reality there is an actual situation where it is difficult to efficiently perform work.

Additionally, a situation is not preferable, in which models that a primary doctor intends to use in an examination are all being used in other examinations or being cleaned. For example, when a primary doctor intends to use a small-diameter endoscope in a routine examination and when no small-diameter endoscope is available, it is inevitable to use, as a substitute, an endoscope for precise examination that is not small in diameter. For this reason, it is preferable that: an endoscope suitable for examination is used by avoiding, as much as possible, a situation where a small-diameter endoscope is used in an examination where it is not essential to use a small-diameter endoscope.

Additionally, an endoscope that has become more worn and aged is more likely to cause functional deterioration or a malfunction. An endoscope, which has been used extremely more times, used for a longer time, or used in the larger number of times of biopsies than other similar observation endoscopes in a medical facility, or which has been used in the extremely larger number of times of various treatments and procedures, used for a longer time, or used in the larger number of times of various treatment tools than other similar treatment endoscopes, is to be exceptionally worn out and aged. If the orientation of an angle changes due to extension of a wire, or if perforation of a forceps channel occurs due to insertion of a forceps or a cleaning brush, such an endoscope needs to be repaired. Usually, endoscopes are managed to be inspected regularly, but an endoscope that has been particularly worn out is put out of service for unscheduled repair, which is not preferable because the number of the endoscopes that can be used becomes small in a medical facility. Therefore, there is a demand for avoiding the use of the endoscopes that may be exceptionally worn out.

When a medical facility possesses endoscope cleaning machines of multiple types, a person preparing for examination is required to determine which cleaning machine is used for the cleaning of an endoscope that was used in an examination, but demanding always suitable determinations in the intervals among busy endoscopic examinations puts a burden on a person preparing for examination. Also, medicinal solutions to be used for the cleaning are generally different depending on the models of cleaning machines, but there are medicinal solutions that can have an undesirable influence, such as deterioration of an endoscope member. This is also referred to as an attack property of a medicinal solution, and when a specific individual of endoscopes is cleaned many times by a cleaning machine using a medicinal solution having a strong attack property, there is the possibility that the deterioration of the individual may be accelerated, which is not preferable.

Therefore, it is preferable to set an appropriate examination schedule and a cleaning schedule with respect to each individual of endoscopes such that a doctor and a person preparing for examination perform an examination and preparation work according to the respective schedules.

With the spread and development of IT systems, new information and knowledge, etc., using various accumulated data have been discovered, and also in a medical field, similar phenomena are expected to occur, the similar phenomena being referred to as "secondary use of data."

In endoscopic examinations, there is a challenge where endoscopes are maintained in good conditions for a long time by preventing the aging and a malfunction thereof. Early aging or frequent occurrence of malfunctions is an obstacle for an efficient examination, and further it may cause an economic loss in which maintenance and repair cost is increased. In order to prevent such aging or occurrence of malfunctions, correct operation and handling of various devices such as endoscopes and treatment tools, etc., become very important. The operation and handling of an endoscope include, for example, an endoscope operation by a doctor and insertion of a forceps assisted by a person preparing for examination during an examination, transportation of an endoscope before and after an examination, connection to a camera control unit (CCU), cleaning thereof after the use in an examination, and the like. These operations and handling are performed by doctors and persons preparing for examination, and endoscope manufacturers distribute materials or hold workshops to enlighten them on correct operations and handling.

In reality, however, a situation occurs in which the degrees of aging or malfunctions are different for each endoscope. These differences may be caused due to the handling by individuals of doctors and persons preparing for examination, and it becomes possible to share the information on appropriate operations and handling in a medical facility by recording and analyzing any useful data on the usage condition thereof in the case where an endoscope can be used in a good condition for a long time and in the case where, conversely, aging is accelerated or malfunctions occur frequently.

The present invention has been made in view of these situations, and a purpose thereof is to provide a technique for appropriately performing scheduling of endoscopes.

Means for Solving the Problem

In order to solve the above problem, an endoscopic examination work support system according to an embodiment of the present invention comprises: an examination schedule management unit that manages an examination schedule of a plurality of endoscopic examinations, including an examination room where an endoscopic examination is to be performed, information on scheduled examination start time, that on scheduled examination end time, and examination type information on the examination content of an endoscopic examination; an endoscope assignment unit that assigns, from a plurality of endoscopes, an endoscope to be used to each endoscopic examination managed by the examination schedule management unit; a cleaning machine assignment unit that assigns, from a plurality of cleaning machines, a cleaning machine for cleaning an endoscope to be used in each endoscopic examination; and a cleaning schedule management unit that manages a cleaning schedule of a plurality of endoscopes, including a cleaning machine, information on scheduled cleaning start time, and that on scheduled cleaning end time. The cleaning machine assignment unit assigns a cleaning machine for cleaning an endoscope, to an endoscope assigned to an endoscopic examination by the endoscope assignment unit, so that a time after a scheduled examination end time of the endoscope becomes a scheduled cleaning start time, and the endoscope assignment unit assigns the endoscope to an endoscopic examination such that a time after a scheduled cleaning end time assigned to the endoscope by the cleaning machine assignment unit becomes a scheduled examination start time.

Arbitrary combinations of the above constituting elements and implementations of the invention in the form of methods, apparatuses, systems, recording media, computer programs and so forth may also be effective as additional modes of the present invention.

BRIEF DESCRIPTION OF THE DRAWINGS

FIG. 4 is a view illustrating one example of the generated examination schedule;

FIG. 5 is a view illustrating one example of an examination type master table;

FIG. 6 is a view illustrating one example of a possessed endoscope master table;

FIG. 12 is a view illustrating an examination schedule updated by an examination schedule management unit;

FIG. 14 is a view illustrating a cleaning schedule generated by a cleaning schedule management unit;

FIG. 15 is a view illustrating schedule information on the individuals of endoscopes;

FIG. 16 is a view illustrating an examination schedule generated by the examination schedule management unit and a cleaning schedule generated by the cleaning schedule management unit;

FIG. 17 is a view illustrating an examination schedule generated by the examination schedule management unit and a cleaning schedule generated by the cleaning schedule management unit;

FIG. 18 is a view illustrating an examination schedule generated by the examination schedule management unit and a cleaning schedule generated by the cleaning schedule management unit;

FIG. 19 is a view illustrating the individual schedules of endoscopes;

FIG. 20 is a view illustrating an examination schedule generated by the examination schedule management unit and a cleaning schedule generated by the cleaning schedule management unit;

FIG. 21 is a view illustrating individual schedules of endoscopes for one day;

FIG. 22 is a view illustrating an endoscope order table held in an endoscope order holding unit;

FIG. 24 is a view illustrating a usage condition table stored in a usage condition storage unit;

FIG. 26 is a view illustrating a cleaning machine order table held in a cleaning machine order holding unit;

FIG. 29 is a view illustrating a cleaning schedule generated by the cleaning schedule management unit in Example 3;

FIG. 30 is a view illustrating a preferential endoscope table stored in an assigned endoscope information holding unit;

FIG. 32 is a view illustrating an examination schedule updated by the examination schedule management unit;

FIG. 33 is a view illustrating one example of usage history information displayed on a terminal device;

FIG. 35 is a view illustrating a preferential person-in-charge table stored in an assigned person-in-charge information holding unit;

FIG. 37 is a view illustrating a cleaning schedule generated by the cleaning schedule management unit;

FIG. 38 is a view illustrating a cleaning schedule updated by the cleaning schedule management unit;

FIG. 39 is a view illustrating one example of cleaning history information displayed on a terminal device.

MODE FOR CARRYING OUT THE INVENTION

Figure 1:
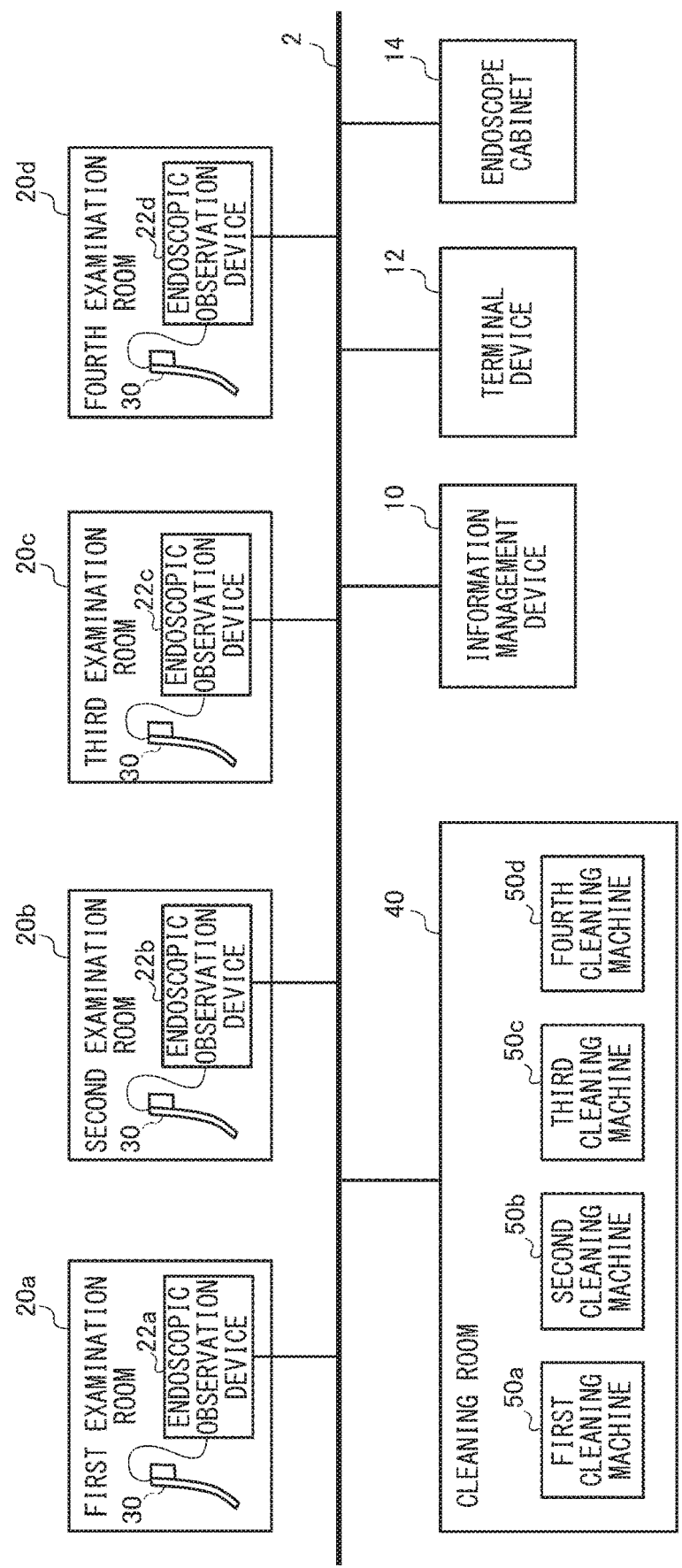
FIG. 1 is a view illustrating a configuration of an endoscopic examination work support system according to an embodiment of the present invention.

FIG. 1 is a view illustrating a configuration of an endoscopic examination work support system 1 according to an embodiment of the present invention. The endoscopic examination work support system 1 is a system for supporting endoscopic examination work, and achieves the function of appropriately scheduling the use schedule and the cleaning schedule of the individuals of endoscopes (hereinafter, also and simply referred to as a "scope") 30. The endoscopic examination work support system 1 comprises: an information management device 10, a terminal device 12, an endoscope cabinet 14, endoscopic observation devices 22a to 22d, and a first cleaning machine 50a to a fourth cleaning machine 50d, which are interconnected to each other by a network 2, such as LAN (local area network).

The endoscopic observation device is installed in each of a plurality of examination rooms. In this embodiment, the endoscopic observation device 22a is installed in a first examination room 20a, the endoscopic observation device 22b in a second examination room 20b, the endoscopic observation device 22c in a third examination room 20c, and the endoscopic observation device 22d in a fourth examination room 20d. In a medical facility, examination rooms are frequently divided into rooms for upper examinations and rooms for lower examinations. In the embodiment illustrated in FIG. 1, the first examination room 20a, the second examination room 20b, and the third examination room 20c are used for upper examinations, and the fourth examination room 20d is used for lower examinations. Hereinafter, when the first examination room 20a to the fourth examination room 20d are not particularly distinguished, each of them may be referred to as an "examination room 20", and when the endoscopic observation devices 22a to 22d are not particularly distinguished, each of them may be referred to as an "endoscopic observation device 22." The endoscope 30 is connected to the endoscopic observation device 22 such that an endoscopic examination is performed by a doctor.

A medical facility such as a large hospital or an endoscopy center possess various models of endoscopes (scopes) and possess a plurality of individuals of the model that is frequently used in order to perform a large number of endoscopic examinations a day. For example, the models of an endoscope for upper examination include an upper routine model to be used in a routine examination, an upper high image quality model that can provide a high resolution image, an upper nasal model to be inserted through a nostril, an upper expansion model that allows observation of the morphology of fine blood vessels on a mucosal surface and a structural pattern by the ducts of a gland, etc., an upper treatment model having a treatment function, and the like. On the other hand, the models of an endoscope for lower examination include a lower routine model to be used in a routine examination, a lower expansion model that allows observation of the morphology of fine blood vessels on a mucosal surface and a structure pattern by the ducts of a gland, etc., a lower treatment model having a treatment function, and the like. The endoscopes possessed by a medical facility are managed by being registered in a database.

A plurality of cleaning machines are installed in a cleaning room 40, and in this embodiment the first cleaning machine 50a, the second cleaning machine 50b, the third cleaning machine 50c, and the fourth cleaning machine 50d are provided. Hereinafter, when the first cleaning machine 50a to the fourth cleaning machine 50d are not particularly distinguished, each of them may also be referred to as a "cleaning machine 50." Although four cleaning machines 50 are installed in the single cleaning room 40 in this embodiment, they may be dispersedly installed in multiple cleaning rooms.

Medicinal solutions to be used for the cleaning are generally different depending on the models of the cleaning machine 50. For example, examples of the medicinal solutions to be used for the cleaning typically include peracetic acid, phtharal, strongly acidic electrolyzed water, and the like, and the cleaning machine 50 is designed to use only a predetermined medicinal solution. That is, the model of the cleaning machine 50 and a medicinal solution to be used are associated in one-to-one correspondence, and it is not recommended that the cleaning machine 50 uses a medicinal solution other than the determined medicinal solution. Additionally, the cleaning time may be different depending on the model of the cleaning machine 50, and thus the cleaning machine 50 has a characteristic peculiar to the model.

The endoscope cabinet 14 stores the endoscope 30. Before the endoscopic examination work for one day is started, all the endoscopes 30 are stored in the endoscope cabinet 14, and a person preparing for examination, such as a technician, takes out the endoscope 30 from the endoscope cabinet 14, and brings it into the examination room 20 to connect to the endoscopic observation device 22. When an examination by a doctor is ended, a person preparing for examination brings the used endoscope 30 into the cleaning room 40 to clean it by putting into the cleaning tank of the cleaning machine 50, and the cleaned endoscope 30 is brought into an examination room such that a doctor reuses it in a new examination.

In a medical facility, it is common that an individual name is given to an individual of the endoscope 30 in order to distinguish from other individuals. For example, the endoscopes 30 of the same type have the same shape, and hence each of them is managed by being provided with an individual name. A seal, or the like, on which an individual name is printed, is attached to the endoscope 30 in order to be distinguish by the individual name, whereby a doctor and a person preparing for examination can distinguish the respective individuals from each other. Additionally, RFID tags, or the like, have recently been embedded in the main bodies of endoscopes, so that each individual can be electronically distinguished by reading it when the endoscopic observation device 22 is connected to a camera control unit (CCU) or with the use of a tag reading means. Such an endoscope 30 can be distinguished similarly to the case where a seal is used, by acquiring the individual identification information in an RFID tag when connected to an CCU or before or after the cleaning in a cleaning machine.

The endoscopic examination work support system 1 of the embodiment sets, for each individual of the endoscope 30, schedule information in which it is determined: which examination uses the individual; which cleaning machine cleans the individual; and the like. Thereby, a person preparing for examination can understand which examination room 20 the individual should be brought into and which cleaning machine 50 the individual should be cleaned by, by seeing the schedule information. At the time, the person preparing for examination can transfer the endoscope 30 properly and clean it according to the schedule information in accordance with the individual name printed on the seal attached to the endoscope 30.

The schedule information on the endoscope 30 is generated by the information management device 10. The timing when the schedule information is generated is before endoscopic examination work for one day starts, and a person preparing for examination can determine the handling of the endoscope 30 by seeing the schedule information displayed on the screen of the terminal device 12. Although the terminal device 12 may be a stationary personal computer, it may be a terminal device such as a portable PDA (Personal Digital Assistant) or a tablet. Additionally, the endoscopic examination work support system 1 may have a large display that everyone can watch, so that the schedule information may be displayed on the large display.

When generating the schedule information, the information management device 10 determines which endoscope 30 is to be assigned to an examination that is scheduled to start at a certain timing, but the endoscope 30 scheduled to be used at the timing or that scheduled to be cleaned at the timing cannot naturally be assigned to the examination. Therefore, the information management device 10 sets, when performing scheduling processing, a virtual status for each endoscope 30, thereby allowing the status of each endoscope 30 at an arbitrary timing to be confirmed.

Figure 2:
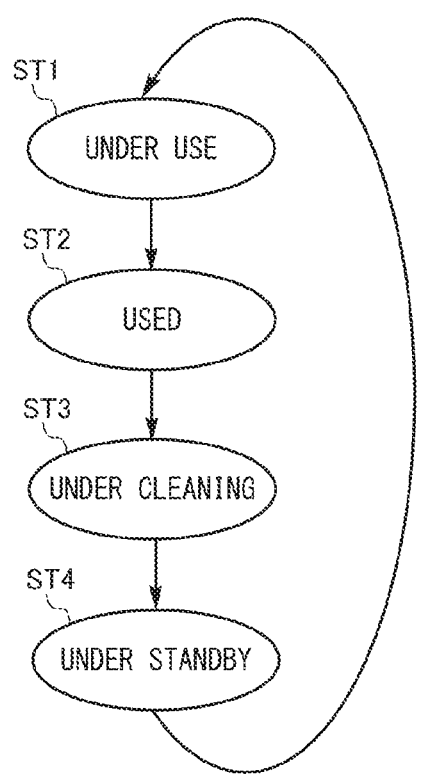
FIG. 2 is a view for explaining a virtual status of an endoscope set during the generation of schedule information.

FIG. 2 is a view for explaining the virtual status of the endoscope 30 that is set during the generation of the schedule information. The endoscope 30 takes any one of the statuses including "under use" (ST1), "used" (ST2), "under cleaning" (ST3) and "under standby" (ST4). The arrows illustrated in FIG. 2 indicate the transition direction of the statuses. By grasping the statuses of all the endoscopes 30 at an arbitrary timing, the information management device 10 assigns the endoscope 30 proper at the timing to an examination.

In the four statuses illustrated in FIG. 2, the endoscope 30 that can be assigned to an examination is the endoscope whose status is "under standby", and the endoscopes 30 that are in other statuses cannot be assigned to an examination. The statuses of the endoscopes 30 stored in the endoscope cabinet 14 are "under standby", and therefore when the processing for generating the schedule information is started, it is assumed that the statuses of all the endoscopes 30 are "under standby."

Figure 3:
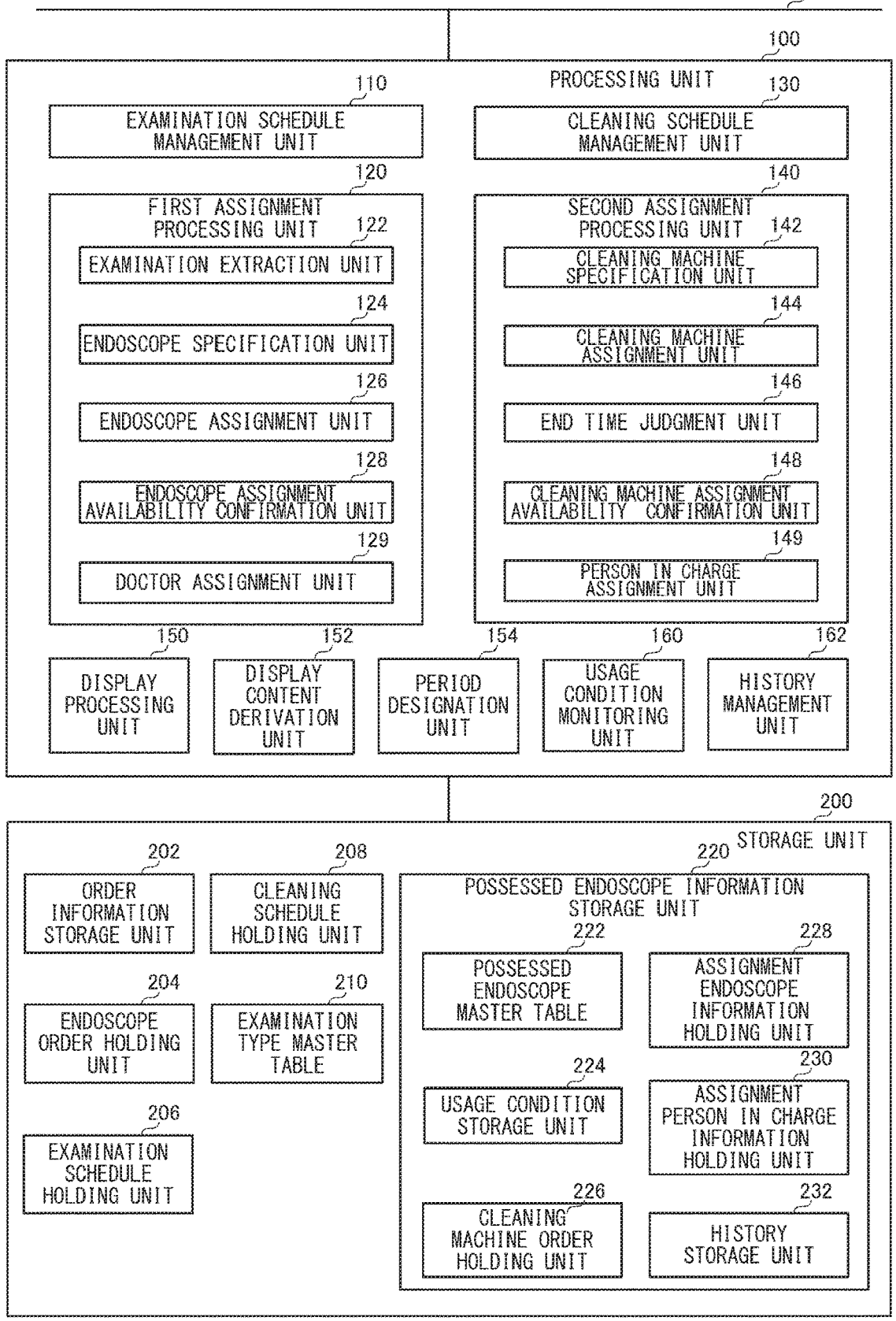
FIG. 3 is a view illustrating a configuration of an information management device for generating schedule information on an endoscope.

FIG. 3 illustrates a configuration of the information management device 10 that generates the schedule information on the endoscope 30. The information management device 10 comprises a processing unit 100 and a storage unit 200, and the processing unit 100 includes an examination schedule management unit 110, a first assignment processing unit 120, a cleaning schedule management unit 130, a second assignment processing unit 140, a display processing unit 150, a display content derivation unit 152, a period designation unit 154, a usage condition monitoring unit 160, and a history management unit 162.

Each component of the information management device 10 can be realized by a CPU, memory, or other LSIs of an arbitrary computer in terms of hardware, and realized by a program or the like loaded in a memory in terms of software, but herein functional blocks realized by the cooperation of hardware and software are depicted. Therefore, it is to be understood by those skilled in the art that these functional blocks can be realized in various forms, namely, solely in hardware, solely in software, or through a combination of hardware and software.

An examination order is generated in a hospital information system such as, for example, an ordering system, and is issued to an endoscopy department system. Before the endoscopic examination work for one day starts, the information management device 10 acquires the examination orders for the one day that have been generated in the hospital information system, so that the use schedule and cleaning schedule of each individual of the endoscopes 30 possessed in a medical facility are scheduled. The acquired examination orders for the one day are stored in an order information storage unit 202. For example, the timing of the scheduling may be before the first examination on the examination day is performed or after the examination work on the previous day is ended, and in any case the scheduling only has to be performed at a timing when the examination orders for one day are fixed.

The examination order includes order information on an endoscopic examination, such as information on scheduled examination start time, that on scheduled examination end time, patient identification information (patient ID), examination type information, primary doctor of the examination, and examination room. In the endoscopic examination work support system 1 illustrated in FIG. 1, it is determined that: the first examination room 20a, the second examination room 20b, and the third examination room 20c are used for upper examinations; and the fourth examination room 20d is used for lower examinations, and therefore any one of the first examination room 20a, the second examination room 20b, and the third examination room 20c is assigned, as an examination room, to an upper examination order, and the fourth examination room 20d is assigned to a lower examination order.

When the scheduling processing is started, the examination schedule management unit 110 first acquires a plurality of order information for one day from the order information storage unit 202 to generate an examination schedule. Specifically, the examination schedule management unit 110 generates and manages an examination schedule of a plurality of endoscopic examinations, including examination rooms where endoscopic examinations are to be performed, information on scheduled examination start time, that on scheduled examination end time, examination type information on the examination contents of the endoscopic examinations, and primary doctors. The examination schedule management unit 110 stores the generated examination schedule in an examination schedule holding unit 206. Thereafter, the examination schedule management unit 110 updates the examination schedule by registering information on the endoscope 30 assigned to each examination by the first assignment processing unit 120 to the examination schedule, as described from now on.

FIG. 4 illustrates one example of the generated examination schedule. When acquiring the order information from the order information storage unit 202, the examination schedule management unit 110 sets examination Nos. in the order starting from the earliest scheduled examination start time. In FIG. 4, the number of examinations for one day is 41, and examination Nos. E1 to E41 are set to the respective examinations. Herein, the examination schedule with examination No. E1 is indicated as follows: the examination room is the first examination room 20a; the scheduled examination start time is 9:00; the scheduled examination end time is 9:10; the examination type is an "upper routine examination"; and the primary doctor is a "doctor B."

In the present embodiment, the examination schedule illustrated in FIG. 4 is automatically derived from a plurality of examination orders for one day, but when information on scheduled examination start time, that on scheduled examination end time, that on a primary doctor, and that on an examination room are not included in the order information, the examination schedule management unit 110 may generate an examination schedule.

For example, the storage unit 200 stores: an examination type master table in which the scheduled examination time of each examination type is stored; a primary doctor master table in which primary doctors are stored; and the condition of an examination to be performed in an examination room (i.e., information for specifying whether it is an upper examination or a lower examination). The examination order includes patient identification information (patient ID) and examination type information, and when acquiring the examination order for one day, the examination schedule management unit 110 generates an examination schedule by referring to the examination type master table, the primary doctor master table, and the examination condition.

FIG. 5 illustrates one example of an examination type master table 210. In the examination type master table 210, the scheduled examination time of each examination type is recorded. When patient identification information (patient ID) and examination type information are included in the examination order, the examination schedule management unit 110 first assigns one examination to each examination room by referring to the examination type information on each examination included in the examination order. When the examination type information designates an upper examination, the examination is assigned to any one of the first examination room 20a, the second examination room 20b, and the third examination room 20c by referring to the examination condition for an examination room, on the other hand, when the examination type information designates a lower examination, the examination is assigned to the fourth examination room 20d. Further, the examination schedule management unit 110 sets a predetermined preparation time (e.g., 5 minutes) as an interval between examinations.

In the examination type master table 210, it is recorded, for example, that: the scheduled examination time of the "upper routine examination" with examination type No. 1 is 10 minutes; that of the "upper nasal examination" with examination type No. 2 is 15 minutes; and the like. The scheduled examination time of the "lower routine examination (experience 3 years)" with examination type No. 16 is set to be 5 minutes longer than that of the "lower routine examination" with examination type No. 9, but this means that: it is incorporated in advance as scheduled time that when a doctor (young doctor) with less than 3-year experience performs an examination, it takes about 5 minutes longer than a doctor (veteran doctor) with 3-year or more experience. Alternatively, it may be set in the primary doctor master table that a young doctor needs more time than a veteran doctor. The examination schedule management unit 110 assigns one examination to each examination room 20 and sets scheduled examination start time and scheduled examination end time, according to the examination type master table 210.

Next, the doctor assignment unit 129 in the first assignment processing unit 120 assigns a doctor to an examination in each examination room 20. At this time, the doctor assignment unit 129 assigns primary doctors to examinations such that the same primary doctor does not overlap in the same time zone. As described above, the examination schedule management unit 110 assigns one examination to each examination room 20, and the doctor assignment unit 129 assigns a doctor to the assigned examination, so that an examination schedule is generated. When the doctor assignment unit 129 assigns a doctor to an examination, the examination schedule management unit 110 again assigns one examination to each examination room by referring to the examination type information on each examination included in an unprocessed examination order, and the doctor assigning unit 129 assigns a doctor to the assigned examination. The examination schedule illustrated in FIG. 4 is generated by repeating this.

In the examination schedule illustrated in FIG. 4, the scheduled examination time of the lower routine examination indicated by examination No. E12 is set to be 20 minutes. This is because when a doctor E is assigned to the lower routine examination indicated by examination No. E12 by the doctor assignment unit 129, the scheduled time of the examination indicated by the examination No. E12 is set to be 5 minutes longer than the scheduled examination time (15 minutes) of a normal lower routine examination since the doctor E is a young doctor with less than 3-year experience. When the examination schedule management unit 110 assigns the lower routine examination indicated by the examination No. E12 to the fourth examination room 20d, the examination schedule management unit 110 sets the scheduled examination time to be 15 minutes as usual; on the other hand, when the doctor assignment unit 129 assigns the doctor E to the examination, the examination schedule management unit 110 resets the scheduled examination end time by lengthening the scheduled examination times by 5 minutes with reference to the scheduled examination time of the examination type No. 16 illustrated in FIG. 5.

As described above, when examination room information, information on scheduled examination start time, that on scheduled examination end time, primary doctor information, and the like are not included in the order information, the processing unit 100 may have the function of automatically generating an examination schedule, which is achieved in the following way: the examination schedule management unit 110 sets, as the premise of assigning the endoscope 30 to an examination, an examination room where the examination is to be performed, scheduled examination start time, and scheduled examination end time by referring to the examination type master table 210, etc., as described above; and the doctor assignment unit 129 assigns a doctor to the examination.

A possessed endoscope information storage unit 220 stores information and data on the endoscopes 30 that a medical facility possesses, and includes a possessed endoscope master table 222, a usage condition storage unit 224, a cleaning machine order holding unit 226, an assigned endoscope information holding unit 228, an assigned person-in-charge information holding unit 230, and a history recording unit 232. The possessed endoscope master table 222 is a database for managing the endoscopes 30 that a medical facility possesses, and the information on all the endoscopes 30 that the medical facility possesses are registered.

FIG. 6 illustrates one example of the possessed endoscope master table 222. The possessed endoscope master table 222 registers the endoscope Nos. set in the medical facility, model names, and individual names in the medical facility, by associating them with each other. Herein, as endoscope models for upper examination, an upper routine model to be used in a routine examination, an upper high image quality model that can provide a high resolution image, an upper nasal model to be inserted through a nostril, an upper expansion model that allows observation of the morphology of fine blood vessels on a mucosal surface and a structural pattern by the ducts of a gland, etc., and an upper treatment model having a treatment function are registered.

Six upper routine models are possessed in the medical facility, which are provided with individual names of G-R-1, G-R-2, G-R-3, G-R-4, G-R-5, and G-R-6, respectively. Three upper high image quality models are possessed, which are provided with individual names of G-H-1, G-H-2, and G-H-3, respectively; one upper nasal endoscope is possessed, which is provided with an individual name of G-N-1; two upper expansion models are possessed, which are provided with individual names of G-Z-1 and G-Z-2, respectively; and two upper treatment models are possessed, which are provided with individual names of G-T-1 and G-T-2, respectively.

On the other hand, as endoscope models for lower examinations, a routine lower model to be used in a routine examination, a lower expansion model that allows observation of the morphology of fine blood vessels on a mucosal surface and a structure pattern by the ducts of a gland, etc., and a lower treatment model having a treatment function are registered. Three lower routine models are possessed, which are provided with individual names of C-R-1, C-R-2, and C-R-3, respectively; one lower expansion model is possessed, which is provided with an individual name of C-Z-1; and one lower treatment model is possessed, which is provided with an individual name of C-T-1.

Each endoscope 30 is attached with a tape or the like on which each individual name is printed so that a doctor or a person preparing for examination can visually specify individuals. A means for specifying and displaying individuals is not limited to tapes, but in particular, when there are a plurality of endoscopes 30 of the same model, it is preferable that a means, which allows individuals to be visually specified so that they can be distinguished within the same model, is provided.

Hereinafter, the processing for generating the schedule information on the endoscope 30 will be described. Generating the schedule information on the endoscope 30 means assigning the endoscopes 30 to examinations and assigning the endoscopes 30 that were used in examinations to cleaning machines, and as a result, an examination schedule and a cleaning schedule are generated, and a schedule of the individuals of the endoscopes 30 is also generated.

Figure 7:
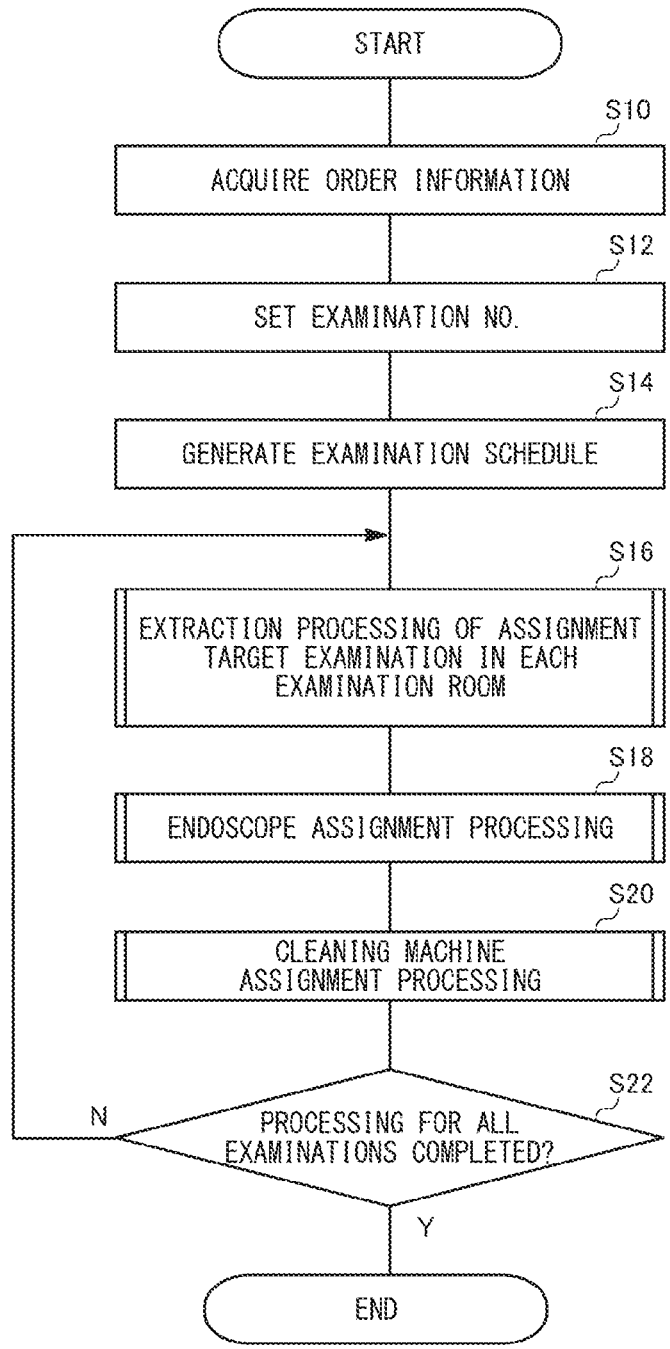
FIG. 7 is a view illustrating a basic flowchart in which schedule information on an endoscope is generated.

FIG. 7 illustrates a basic flowchart for generating the schedule information on the endoscope 30. The examination schedule management unit 110 acquires a plurality of order information for one day from the order information storage unit 202 (S10). With reference to the scheduled examination start times in a plurality of order information, the examination schedule management unit 110 sets examination Nos. in the order starting from the earliest scheduled examination start time (S12), whereby generates an examination schedule (S14). For a plurality of examinations whose scheduled examination start times are the same, examination Nos. may be set in ascending order of examination room Nos. The examination room Nos. are set to be "1" for the first examination room 20a, "2" for the second examination room 20b, "3" for the third examination room 20c, and "4" for the fourth examination room 20d. The examination schedule generated in S14 is the one illustrated in FIG. 4, in which by taking time axis as the vertical axis and examination rooms as the horizontal axis, an examination order is assigned within a time frame designated by the information on scheduled examination start time and that on scheduled examination end time.

The information on scheduled examination start time and that on scheduled examination end time may be information on time itself indicating hour and minute, but may be ones indicating time zones in 5-minute increments. For example, when the scheduling is performed with 5 minutes as one unit in an endoscopy department, the information on scheduled examination start time and that on scheduled examination end time may designate a scheduled examination start time and a scheduled examination end time, respectively, based on a frame with 5 minutes as one unit.

The schedule information on the endoscope 30 is generated by assigning the endoscope 30 to an examination in the examination schedule and assigning a cleaning machine, which performs cleaning after the scheduled examination end time, to the assigned endoscope 30. Therefore, processing for extracting an examination, to which the endoscope 30 is to be assigned in each examination room, is first performed (S16). When the examination in each examination room is extracted by the assignment target examination extraction processing, processing for assigning the endoscope 30 to the extracted examination is performed by the first assignment processing unit 120 (S18). When the endoscope 30 is assigned to the examination by the endoscope assignment processing, the information on the assigned endoscope 30 is registered in the examination schedule, and subsequently processing for assigning the cleaning machine 50 for cleaning to the assigned endoscope 30 is performed by the second assignment processing unit 140 (S20). The information on the cleaning machine 50 assigned to the endoscope 30 is registered in the cleaning schedule. The steps of S16 to S20 are repeated until all the examinations are completed (S22/N), and when the assignment processing is completed for all the examinations (S22/Y), scheduling processing of the endoscope 30 ends.

When the steps of S16 to S20 are performed, the endoscope 30 is assigned to an examination in each examination room 20, and the cleaning machine 50 is assigned to the assigned endoscope 30. When the use schedule and cleaning schedule of the endoscope 30 are thus determined, the second assignment processing unit 140, which assigned the cleaning machine 50, sets a processed flag for the examination No. of the examination to which the endoscope 30 was assigned. The first assignment processing unit 120 that assigns the endoscope 30 to an examination refers to the flag of each examination No. and performs the step of S16 until the flags of all the examination Nos. are processed (S22/N), and the flags of all the examination Nos. are processed (S22/Y), the scheduling processing of the endoscope 30 ends without returning to the step of S16.

Returning to FIG. 3, the first assignment processing unit 120 performs processing for assigning the endoscope 30 to an examination in the examination schedule. Specifically, the first assignment processing unit 120 has the function of performing the steps of S16 and S18 of the basic flowchart, and includes an examination extraction unit 122, an endoscope specification unit 124, an endoscope assignment unit 126, an endoscope assignment availability confirmation unit 128, and a doctor assignment unit 129. As described above, the doctor assignment unit 129 takes charge of processing for assigning a doctor to an examination in generating the examination schedule.

Figure 8:
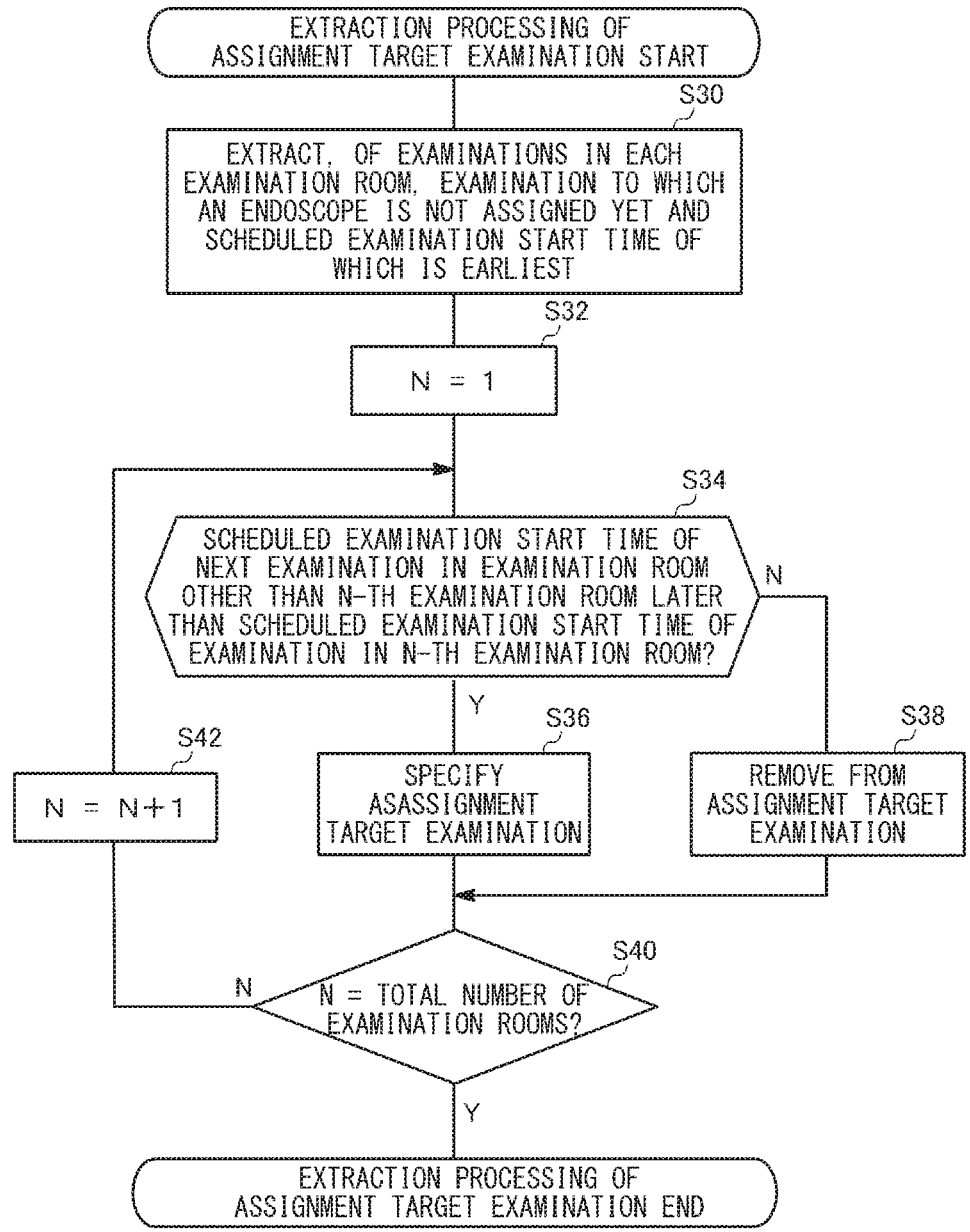
FIG. 8 is a view illustrating a detailed flowchart of the assignment target examination extraction processing illustrated in S16 of the basic flowchart.

FIG. 8 illustrates a detailed flowchart of the assignment target examination extraction processing illustrated in S16 of the basic flowchart. In the first assignment processing unit 120, the examination extraction unit 122 extracts, of the examinations in each examination room 20 in the examination schedule, an examination that is not yet assigned with the endoscope 30 and the scheduled examination start time of which is earliest (S30). In the examination schedule illustrated in FIG. 4, the endoscope 30 is not yet assigned to any examination, so that the examination extraction unit 122 extracts the respective examinations the scheduled examination start time of each of which is earliest in each examination room 20. Herein, the examination with examination No. E1, the examination with examination No. E2, the examination with examination No. E3, and the examination with examination No. E4 are extracted from the first examination room 20a, the second examination room 20b, the third examination room 20c, and the fourth examination room 20d, respectively. Hereinafter, for convenience of description, the examination with examination No. E1 may be referred to as an "examination E1", and the examination with examination No. E2 as an "examination E2", etc.

Subsequently, the examination extraction unit 122 sets "N=1" (S32), and determines whether the scheduled examination start time of the examination next to the examination extracted from an examination room other than the N-th examination room is later than the scheduled examination start time of the examination extracted from the N-th examination room (S 34). Herein, by comparing the scheduled examination start time of the examination E1 extracted from the first examination room 20a with the scheduled examination start times of the examinations next to the examinations E2, E3, and E4 respectively extracted from the second examination room 20b, the third examination room 20c, and the fourth examination room 20d, that is, with the scheduled examination start times of the examinations E6, E7, and E8, the examination extraction unit 122 determines whether all of the scheduled examination start times of the examinations E6, E7, and E8 are later than the scheduled examination start time of the examination E1. In the examination schedule illustrated in FIG. 4, all of the scheduled examination start times of the examinations E6, E7, and E8 are later than the scheduled examination start time of the examination E1 (S34/Y), and hence the examination extraction unit 122 specifies the examination E1 as an examination to which the endoscope 30 is to be assigned (S36). If even any one of the scheduled examination start times of the examinations E6, E7, and E8 is earlier than the scheduled examination start time of the examination E1 (S34/N), the examination extraction unit 122 excludes the examination E1 from the examinations to which the endoscope 30 is to be assigned (S 38).

Subsequently, it is determined whether N is equal to the total number of examination rooms (in this embodiment, the total number thereof=4) (S40), and when N does not reach the total number of examination rooms (S40/N), N is incremented by 1 (S42) and the processing returns to S34.

In S34, by comparing the scheduled examination start time of the examination E2 extracted from the second examination room 20b with the scheduled examination start times of the examinations next to the examinations E1, E3, and E4 respectively extracted from the first examination room 20a, the third examination room 20c, and the fourth examination room 20d, that is, with the scheduled examination start times of the examinations E5, E7, and E8, the examination extraction unit 122 determines whether all of the scheduled examination start times of the examinations E5, E7, and E8 are later than the scheduled examination start time of the examination E1. In the examination schedule illustrated in FIG. 4, all of the scheduled examination start times of the examinations E5, E7, and E8 are later than the scheduled examination start time of the examination E2 (S34/Y), and hence the examination extraction unit 122 specifies the examination E2 as an examination to which the endoscope 30 is to be assigned (S36).

As described above, the determination processing of S34 is performed for all the examinations extracted from each examination room 20 in S30. Herein, all the examinations with examination Nos. E1, E2, E3, and E4 extracted from each examination room 20 in S 30 are specified as examinations to which the endoscope 30 is to be assigned (S36), and because N reaches the total number of examination rooms at that time (S40/Y), the assignment target examination extraction processing ends. With reference to the basic flowchart illustrated in FIG. 7, when the assignment target examination extraction processing of S16 ends, the endoscope assignment processing of S18 is started.

Figure 9:
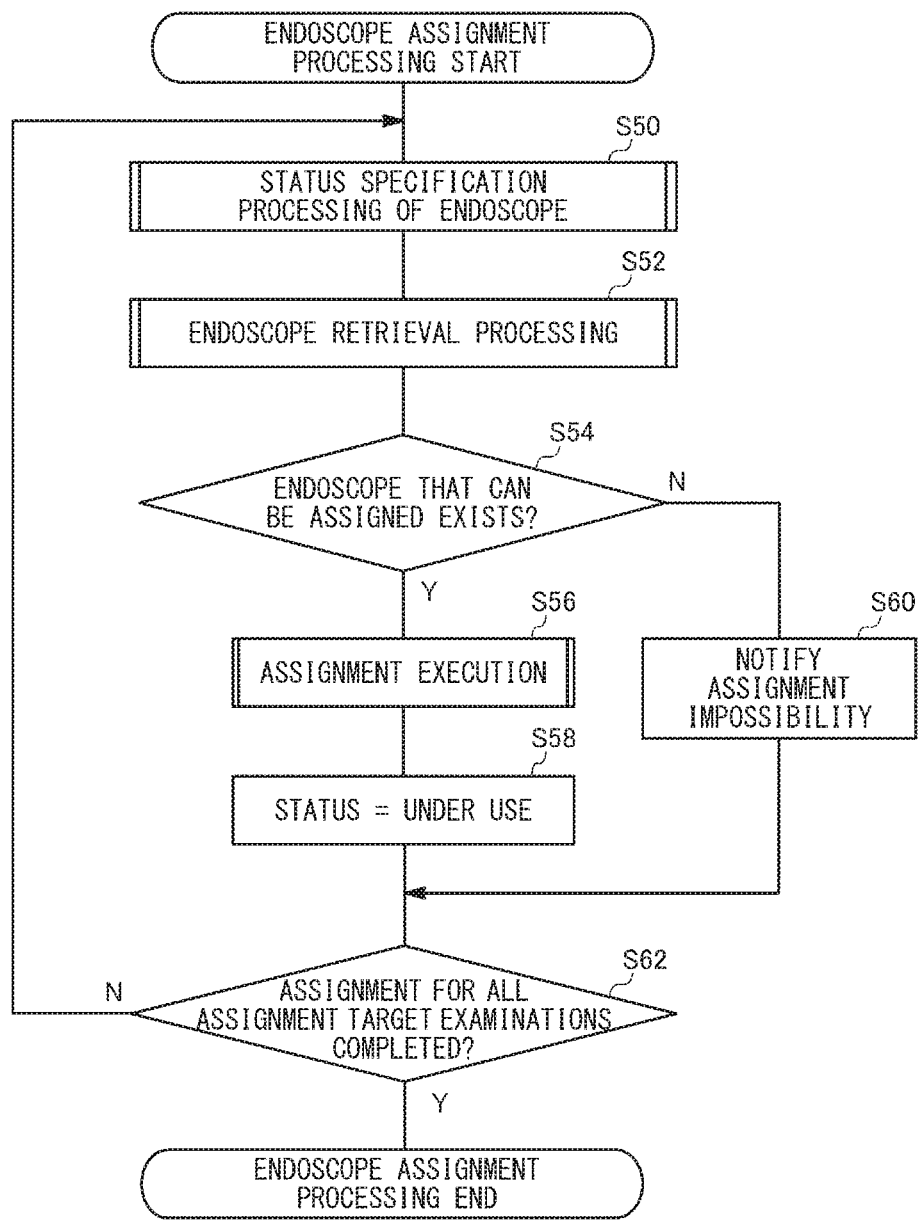
FIG. 9 is a view illustrating a detailed flowchart of the endoscope assignment processing illustrated in S18 of the basic flowchart.

FIG. 9 illustrates a detailed flowchart of the endoscope assignment processing illustrated in S18 of the basic flowchart. In the first assignment processing unit 120, the endoscope assignment unit 126 performs processing for assigning, of a plurality of possessed endoscopes 30, an endoscope to be used to each endoscopic examination whose schedule is managed by the examination schedule management unit 110.

As a premise for performing the endoscope assignment processing, the endoscope specification unit 124 first specifies the statuses of all the endoscopes 30 at the scheduled start time of the examination extracted as an endoscope assignment target (S50). As described with reference to FIG. 2, the status of the endoscope 30 is specified by any one of ST1 to ST4.

Figure 10:
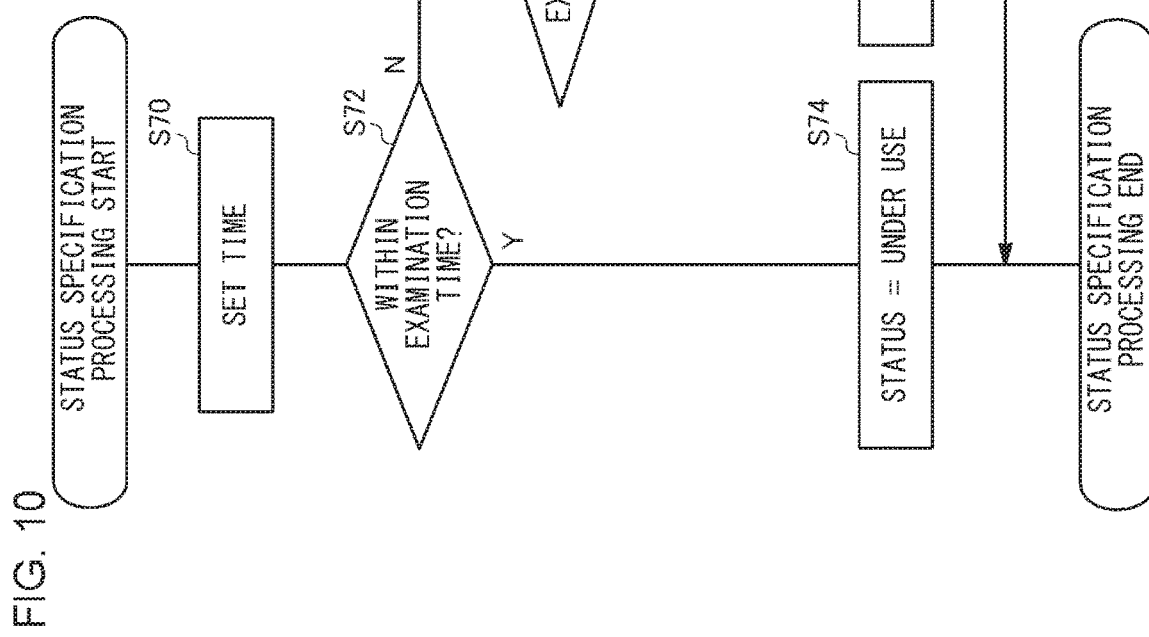
FIG. 10 is a view illustrating a detailed flowchart of the status specification processing of S50.

FIG. 10 illustrates a detailed flowchart of the status specification processing of S50. The endoscope specification unit 124 first sets the scheduled examination start time of an examination to be an assignment target (S70). Because the scheduled examination start times of the examinations E1 to E4 are all 9:00, time is set to 9:00 herein. The endoscope specification unit 124 specifies the statuses, at the set time, of all the endoscopes with endoscope Nos. 1 to 19 recorded in the possessed endoscope master table 222.

With reference to the schedule information on the endoscope 30, if the set time (9:00) is within the time period of the assigned examination (S72/Y), the status of the endoscope 30 is specified as "under use" (S74). Also, if the set time is outside the time period of the examination (S72/N) and is after the end of the assigned examination and before the start of cleaning (S76/Y), the status of the endoscope 30 is specified as "used" (S78). Also, if the set time is after the end of the examination and is not before the start of cleaning (S76/N) but within a cleaning time (S80/Y), the status of the endoscope 30 is specified as "under cleaning" (S82). Also, if the set time is not even within a cleaning time (S80/N), the status of the endoscope 30 is specified as "under standby" (S84). In this way, the endoscope specification unit 124 can grasp which endoscope is "under standby" at a scheduled examination start time, that is, which endoscope can be assigned, by specifying the statuses, at the set time, of all the endoscopes.

Returning to FIG. 9, the endoscope specification unit 124 performs retrieval processing on the possessed endoscopes to specify an available endoscope 30 (S52). Herein, the endoscope specification unit 124 performs the retrieval processing by narrowing down to the endoscopes specified as "under standby" in S50. Because the endoscope 30, the status of which is other than "under standby", that is, "under use", "used", or "under cleaning", cannot be assigned to an examination at that time, retrieval efficiency can be improved by excluding it from the retrieval targets.

Figure 11:
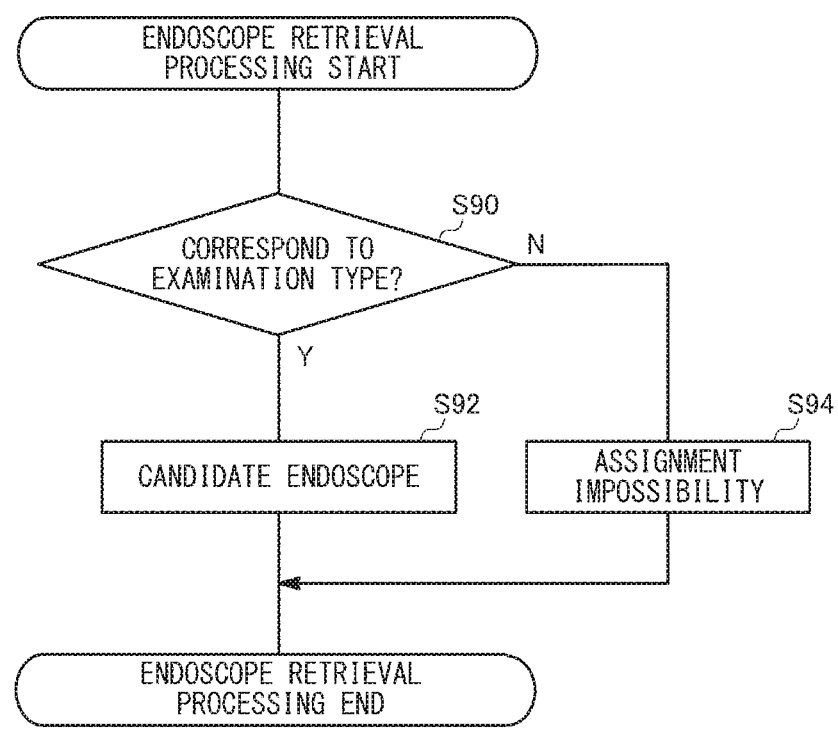
FIG. 11 is a view illustrating a detailed flowchart of the endoscope retrieval processing of S52.

FIG. 11 illustrates a detailed flowchart of the endoscope retrieval processing in S52. The endoscope specification unit 124 performs retrieval processing on all the endoscopes 30 whose statuses are "under standby." Herein, the endoscope specification unit 124 specifies the examination type of an examination to be an assignment target. Herein, the scheduled examination start times of all the examinations E1 to E4 that are assignment targets are 9:00, and it is specified in S50 that the statuses of all the endoscopes 30 are "under standby" at 9:00. Therefore, the endoscope specification unit 124 determines whether the endoscope 30 whose status is "under standby" corresponds to the examination type of each of the examinations E1, E2, E3, and E4 (S90).

In the embodiment, the endoscope specification unit 124 specifies an available endoscope 30 based on the examination type information on an endoscopic examination to be an assignment target. In the embodiment, the examination type is distinguished by whether it is an upper examination or a lower examination. Therefore, when the examination type information on an examination indicates an upper examination, it is determined in S90 that an endoscope for upper examination corresponds and an endoscope for lower examination does not correspond. Similarly, when the examination type information on an examination indicates a lower examination, it is determined that an endoscope for lower examination corresponds and an endoscope for upper examination does not correspond.

With reference to the possessed endoscope master table 222 illustrated in FIG. 6 and the examination schedule illustrated in FIG. 4, the endoscope specification unit 124 determines the endoscopes with endoscope Nos. 1 to 14, which are endoscopes for upper examination, as candidate endoscopes for the upper examinations with examination Nos. E1, E2, and E3 (S92); on the other hand, determines the endoscopes with endoscope Nos. 15 to 19, which are endoscopes for lower examination, as unassignable for the examinations with examination Nos. E1, E2, and E3 (S94). Additionally, the endoscope specification unit 124 determines the endoscopes with endoscope Nos. 15 to 19, which are endoscopes for lower examination, as candidate endoscopes for the lower examination with examination No. E4 (S92); on the other hand, determines the endoscopes with endoscope Nos. 1 to 14, which are endoscopes for upper examination, as unassignable for the examination with examination No. E4 (S94). The endoscope specification unit 124 notifies the endoscope assignment unit 126 of the correspondence between the specified candidate endoscopes and the examination Nos.

Returning to FIG. 9, the endoscope assignment unit 126 assigns the endoscope 30 to be used to each examination managed by the examination schedule management unit 110 based on the candidate endoscopes specified by the endoscope specification unit 124. Specifically, the endoscope assignment unit 126 assigns one of the candidate endoscopes specified by the endoscope specification unit 124 to an endoscopic examination. In the following example, of the plurality of candidate endoscopes, an endoscope with a smaller endoscope No., set in the possessed endoscope master table 222 illustrated in FIG. 6, is sequentially assigned to an examination, but it is not intended to limit to this order.

The endoscope assignment unit 126 first determines that there is an endoscope assignable to the examination E1 (S54/Y). Herein, it is notified by the endoscope specification unit 124 that the endoscopes with endoscope Nos. 1 to 14 can be assigned to the examinations E1, E2, and E3, and therefore the endoscope assignment unit 126 assigns the endoscope G-R-1 with endoscope No. 1 to the examination E 1 (S56). The endoscope assignment unit 126 sets the status of the endoscope G-R-1 to be "under use" such that the same endoscope G-R-1 is not assigned to another examination (S 58). When the status is set to be "under use", the endoscope G-R-1 is excluded from the candidate endoscopes in the next assignment by the endoscope assignment unit 126.

Next, the endoscope assignment unit 126 determines that there is an endoscope that can be assigned to the examination E 2 (S54/Y), and assigns the endoscope G-R-2 with endoscope No. 2 to the examination E2 (S56), and sets the status of the endoscope G-R-2 to be "under use" (S58). Similarly, the endoscope assignment unit 126 assigns the endoscope G-R-3 with endoscope No. 3 to the examination E3 (S56), and sets the status of the endoscope G-R-3 to be "under use" (S58).

Next, the endoscope assignment unit 126 determines that there is an endoscope assignable to an examination E4 (S54/Y). Herein, it is notified by the endoscope specification unit 124 that the endoscopes with endoscope Nos. 15 to 19 can be assigned to the examination E4, and therefore the endoscope assignment unit 126 assigns an endoscope C-R-1 with endoscope No. 15 to the examination E4 (S56), and sets the status of the endoscope C-R-1 to be "under use" (S58).

In S54, when there is no endoscope that can be assigned to an examination (S54/N), the endoscope assignment unit 126 notifies a user that assignment cannot be performed (S60). The timing of this notification may be after the assignment processing of the endoscope 30 is completed for all the examinations. Before the endoscopic examination work for one day starts, at least the user needs to recognize that there is an examination to which the endoscope 30 is not assigned.

The assignment processing by the endoscope assignment unit 126 is repeated until the assignment of the endoscopes 30 to all the extracted examinations to be assignment targets is completed (S62/N), and when the endoscopes 30 are assigned to all the examinations (herein, E1 to E4) (S62/Y), this endoscope assignment processing ends. The results of the assignment by the endoscope assignment unit 126 is notified to the examination schedule management unit 110.

FIG. 12 illustrates an examination schedule updated by the examination schedule management unit 110. When the results of the assignment is notified from the endoscope assignment unit 126, the examination schedule management unit 110 registers the assigned endoscope 30 in the corresponding examination. Herein, it is registered that: the endoscope G-R-1 is used in the examination E1; the endoscope G-R-2 in the examination E2; the endoscope G-R-3 in the examination E3; and the endoscope C-R-1 in the examination E4. The examination schedule management unit 110 stores the updated examination schedules in the examination schedule holding unit 206. In this way, the schedule information on the endoscopes G-R-1, G-R-2, G-R-3, and C-R-1 are generated.

Returning to FIG. 7, when the endoscope assignment processing of S18 end, the cleaning machine assignment processing of S20 is started. In FIG. 3, the cleaning schedule management unit 130 manages a cleaning schedule of a plurality of endoscopes, including the cleaning machines 50, information on scheduled cleaning start time, and that on scheduled cleaning end time. The second assignment processing unit 140 assigns, of a plurality of the cleaning machines 50, a cleaning machine 50 for cleaning the endoscope 30 to be used in each endoscopic examination. The cleaning schedule management unit 130 generates a cleaning schedule of the endoscopes 30 based on the cleaning machines 50 assigned to the endoscopes 30 by the second assignment processing unit 140, and records it in the cleaning schedule holding unit 208.

Figure 13:
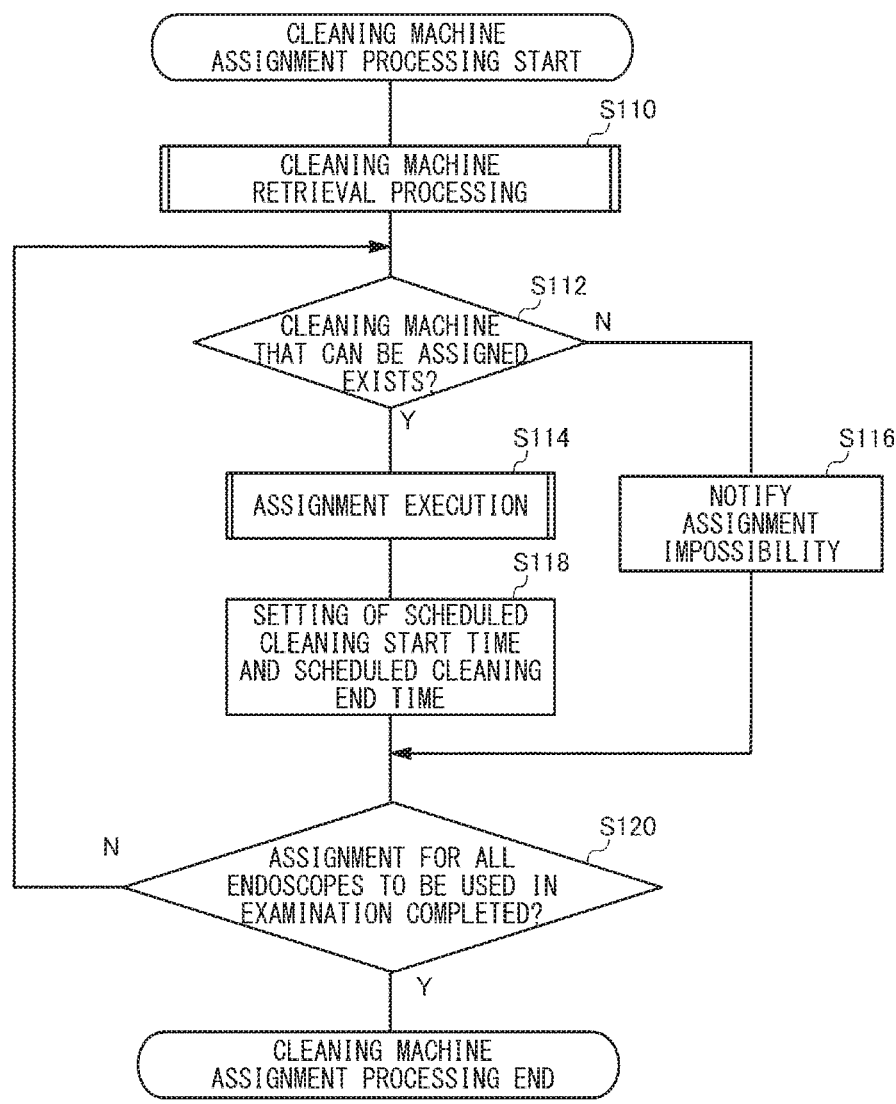
FIG. 13 is a view illustrating a detailed flowchart of the cleaning machine assignment processing illustrated in S20 of the basic flowchart.

FIG. 13 illustrates a detailed flowchart of the cleaning machine assignment processing indicated by S20 of the basic flowchart. The second assignment processing unit 140 includes a cleaning machine specification unit 142, a cleaning machine assignment unit 144, an end time determination unit 146, a cleaning machine assignment availability confirmation unit 148, and a person-in-charge assignment unit 149.

The cleaning machine specification unit 142 specifies available cleaning machines 50 by performing retrieval processing on the possessed cleaning machines 50 for the respective endoscopes 30 assigned in S18 (S110). When the use of the cleaning machine 50 is not restricted, that is, when the use of all the cleaning machines 50 is permitted to the endoscopes 30, the cleaning machine specification unit 142 specifies that all of the first cleaning machine 50a to the fourth cleaning machine 50d are available. At this time, the cleaning machine specification unit 142 acquires an available time zone for each cleaning machine 50 by referring to the cleaning schedule held in the cleaning schedule holding unit 208. The available time zone means a time zone during which cleaning is not scheduled. When the second assignment processing unit 140 initially executes the cleaning machine assignment processing, the cleaning schedule is blank, that is, no cleaning schedule is registered with any of the cleaning machines 50, and therefore all the time zones are available. The available cleaning machines 50 and their available time zones are notified to the cleaning machine assignment unit 144.

The cleaning machine assignment unit 144 assigns, of a plurality of available cleaning machines 50, a cleaning machine 50 for cleaning the endoscope 30 to be used in each endoscopic examination. Herein, the cleaning machine assignment unit 144 assigns the cleaning machine 50 for cleaning an endoscope 30 assigned to an endoscopic examination by the endoscope assignment unit 126, so that a time after the scheduled end time of examination of the endoscope 30 becomes a scheduled cleaning start time. In the present embodiment, it is made possible from the viewpoint of improving work efficiency to set the same time as the scheduled examination end time to be the scheduled cleaning start time, but an interval of a predetermined period of time may be provided between the scheduled examination end time and the scheduled cleaning start time. Further, in the embodiment, it is assumed that the cleaning machine 50 cleans one endoscope 30, but the cleaning machine 50 can clean a plurality of (e.g., two) endoscopes 30 depending on the specification, and hence the cleaning machine assignment unit 144 may assign the cleaning machine 50 to a plurality of the endoscopes 30.

The cleaning machine assignment unit 144 assigns the cleaning machine 50 to, of a plurality of the endoscopes 30 to which the cleaning machine 50 is to be assigned, that is, of a plurality of the endoscopes 30 assigned to examinations in S18, the endoscopes 30 in the order starting from the earliest scheduled examination end time. Herein, the scheduled examination end times of the examinations E1 to E3 are 9:10 and that of the examination E4 is 9:15, and hence the cleaning machine assignment unit 144 assigns the cleaning machines 50 to the endoscopes to be used, in the order of the examinations E1, E2, E3, and E4. In the present embodiment, it is assumed that the cleaning machine 50, which can be assigned to the endoscope 30, always exists (S112/Y), but when the assignable cleaning machine 50 does not exist (S112/N), it is notified that the cleaning machine 50 cannot be assigned to the endoscope 30 (S116).

The cleaning machine assignment unit 144 assigns the first cleaning machine 50a to the endoscope G-R-1 to be used in the examination E1 (S114). In the embodiment, the scheduled cleaning times of all the cleaning machines 50 are set to be 20 minutes, but the scheduled cleaning time may be different for each cleaning machine 50, and that may also be different depending on cleaning modes in the cleaning machine 50. The cleaning machine assignment unit 144 sets the scheduled end time of the examination E1 to be a scheduled cleaning start time, and sets the time 20 minutes after that to be a scheduled cleaning end time (S118). As a result of this assignment, the status of the first cleaning machine 50a between 9:10 and 9:30 is set to be "under use." The status of the cleaning machine 50 becomes either "under use" or "under standby", and when the processing for generating schedule information is started, it is assumed that the statuses of all the cleaning machines 50 are "under standby." The status of the endoscope G-R-1 between 9:10 and 9:30 is "under cleaning."

Next, the cleaning machine assignment unit 144 assigns the second cleaning machine 50b to the endoscope G-R-2 to be used in the examination E2 (S114). The cleaning machine assignment unit 144 sets the scheduled end time of the examination E2 to be a scheduled cleaning start time (9:10), and sets the time 20 minutes after that (9:30) to be a scheduled cleaning end time (S118). As a result of this assignment, the status of the second cleaning machine 50*b* between 9:10 and 9:30 is set to be "under use."

Next, the cleaning machine assignment unit 144 assigns the third cleaning machine 50*c* to the endoscope G-R-3 to be used in the examination E3 (S114). The cleaning machine assignment unit 144 sets the scheduled end time of the examination E3 to be a scheduled cleaning start time (9:10), and sets the time 20 minutes after that (9:30) to be a scheduled cleaning end time (S118). As a result of this assignment, the status of the third cleaning machine 50*c* between 9:10 and 9:30 is set to be "under use."

Finally, the cleaning machine assignment unit 144 assigns the fourth cleaning machine 50*d* to the endoscope C-R-1 to be used in the examination E4 (S114). The cleaning machine assignment unit 144 sets the scheduled end time of the examination E4 to be a scheduled cleaning start time (9:15), and sets the time 20 minutes after that (9:35) to be a scheduled cleaning end time (S118). As a result of this assignment, the status of the fourth cleaning machine 50*d* between 9:15 and 9:35 is set to be "under use."

As described above, the cleaning machine assignment processing is repeated until the cleaning machines 50 are assigned to all the endoscopes 30 to be used in examinations (S120/N). When the cleaning machines 50 are assigned to all the endoscopes 30 to be used in examinations (S120/Y), the cleaning machine assigning processing ends. The results of the assignment by the cleaning machine assignment unit 144 is notified to the cleaning schedule management unit 130.

Figure 14:
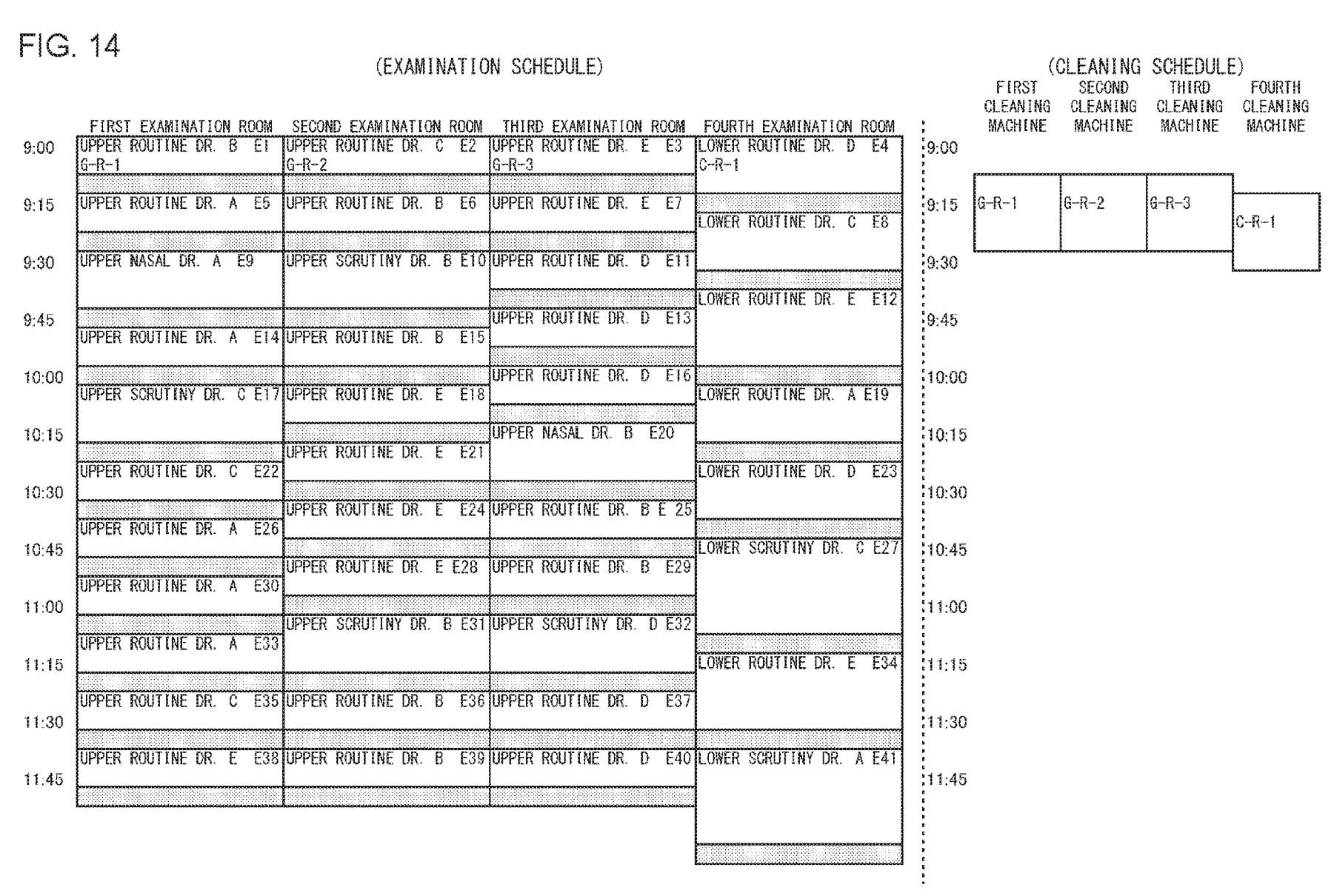

FIG. 14 illustrates a cleaning schedule generated by the cleaning schedule management unit 130. Herein, the results of the assignment by the cleaning machine assignment unit 144 are reflected in the cleaning schedule, and specifically it is registered that between 9:10 and 9:30: the endoscope G-R-1 is cleaned by the first cleaning machine 50*a*; the endoscope G-R-2 by the second cleaning machine 50*b*; and the endoscope G-R-3 by the third cleaning machine 50*c*, and registered that between 9:15 and 9:35 the endoscope C-R-1 is cleaned by the fourth cleaning machine 50*d*. The cleaning schedule management unit 130 records the updated cleaning schedule in the cleaning schedule holding unit 208.

FIG. 15 illustrates schedule information on the individuals of the endoscope 30. Herein, for the sake of easy understanding, an example is illustrated, in which the display processing unit 150 displays an individual schedule at the stage where the above processing is completed, but in fact the display processing unit 150 displays an individual schedule at the stage where all the scheduling are completed. In FIG. 15, C1 indicates that the first cleaning machine 50*a* is under cleaning, C2 indicates that the second cleaning machine 50*b* is under cleaning, C3 indicates that the third cleaning machine 50*c* is under cleaning, and C4 indicates that the fourth cleaning machine 50*d* is under cleaning. Each of E1, E2, and the like indicates the examination No. of an examination under use. Information indicated by such an individual schedule serves as schedule information on each individual.

Returning to FIG. 7, when the cleaning machine assignment processing of S20 ends, it is determined whether the processing is completed for the examinations with all examination Nos. (S22), and when not completed, the basic flow is repeated by returning to S16. Hereinafter, a process will be described, in which schedule information on the endoscope 30 is generated by repeatedly executing the steps of S16 to S20. The steps of S16 to S20 described above with respect to the examinations E1 to E4 serve as the first time processing.

<Second Time: S16 to S20>

In S16, the examination extraction unit 122 extracts the examination E5 from the first examination room 20*a*, the examination E6 from the second examination room 20*b*, the examination E7 from the third examination room 20*c*, and the examination E8 from the fourth examination room 20*d*, thereby specifying the examinations E5 to E8 as the examinations to which the endoscope 30 is to be assigned.

In S18, the endoscope specification unit 124 determines the endoscopes with endoscope Nos. 4 to 14, which are endoscopes for upper examination, as candidate endoscopes for the examinations E5, E6, and E7, and determines the endoscopes with endoscope Nos. 16 to 19, which are endoscopes for lower examination, as candidate endoscopes for the examination E8. Because the statuses of the endoscopes with endoscope Nos. 1 to 3 are "under cleaning" at the scheduled examination start time (9:15) of the examinations E5, E6, and E7, they do not become candidate endoscopes for the examinations E5, E6, and E7. Also, because the status of the endoscope with endoscope No. 15 is "under cleaning" at the scheduled examination start time (9:20) of the examination E8, it dose not become a candidate endoscope for the examination E8. The specified candidate endoscopes are notified to the endoscope assignment unit 126.

In response to the notice from the endoscope specification unit 124, the endoscope assignment unit 126 assigns: an endoscope G-R-4 with endoscope No. 4 to the examination E5; an endoscope G-R-5 with endoscope No. 5 to the examination E6; and an endoscope G-R-6 with endoscope No. 6 to the examination E7. Also, the endoscope assignment unit 126 assigns an endoscope C-R-2 with endoscope No. 16 to the examination E8.

In S20, the cleaning machine assignment unit 144 assigns: the first cleaning machine 50*a* to the endoscope G-R-4 for the examination E5; the second cleaning machine 50*b* to the endoscope G-R-5 for the examination E6; the third cleaning machine 50*c* to the endoscope G-R-6 for the examination E7; and the fourth cleaning machine 50*d* to the endoscope C-R-2 for the examination E8. The cleaning machine assignment unit 144 sets: the scheduled cleaning start times of the endoscopes G-R-4, G-R-5, and G-R-6 to be 9:30; the scheduled cleaning end times thereof to be 9:50; the scheduled cleaning start time of the endoscope C-R-2 to be 9:35; and the scheduled cleaning end time thereof to be 9:55.

Figure 16:
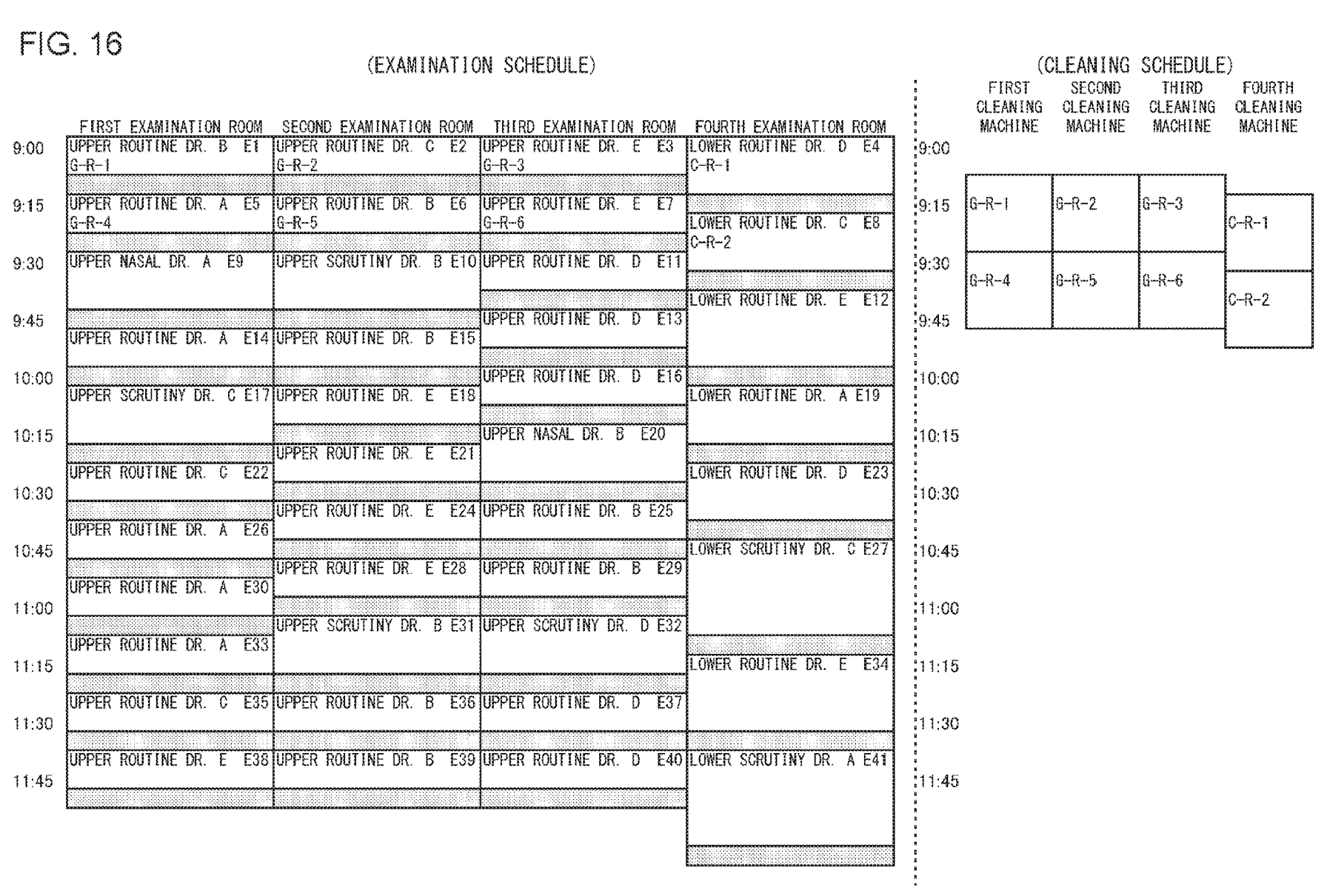

FIG. 16 illustrates an examination schedule generated by the examination schedule management unit 110 and a cleaning schedule generated by the cleaning schedule management unit 130. Herein, the results of the assignment by the endoscope specification unit 124 are reflected in the examination schedule, and those of the assignment by the cleaning machine assignment unit 144 are reflected in the cleaning schedule.

<Third Time: S16 to S20>

In S16, the examination extraction unit 122 extracts: an examination E9 from the first examination room 20*a*; an examination E10 from the second examination room 20*b*; an examination E11 from the third examination room 20*c*; and an examination E12 from the fourth examination room 20*d*, thereby specifying the examinations E9 to E12 as the examinations to which the endoscopes 30 are to be assigned.

In S18, the endoscope specification unit 124 determines the endoscopes with endoscope Nos. 1 to 3 and 7 to 14, which are endoscopes for upper examination, as candidate endoscopes for the examinations E9, E10, and E11, and determines the endoscopes with endoscope Nos. 15 and 17 to 19, which are endoscopes for lower examination, as candidate endoscopes for the examination E12. Because the statuses of the endoscopes with endoscope Nos. 4 to 6 are "under cleaning" at the scheduled examination start times (9:30) of the examinations E9, E10, and E11, they do not become candidate endoscopes for the examinations E9, E10, and E11. Also, because the status of the endoscope with endoscope No. 16 is "under cleaning" at the scheduled examination start time (9:40) of the examination E12, it does not become a candidate endoscope for the examination E12. The specified candidate endoscopes are notified to the endoscope specification unit 124.

The scheduled cleaning end times of the endoscopes with endoscope Nos. 1 to 3 are 9:30 and the cleaning thereof is completed at the time of 9:30, and hence the statuses thereof are "under standby", and they become candidate endoscopes for the examinations E9, E10, and E11. Also, the scheduled cleaning end time of the endoscope with endoscope No. 15 is 9:35, and the status thereof is "under standby" at the time of 9:40, and hence it becomes a candidate endoscope for the examination E12.

In response to the notice from the endoscope specification unit 124, the endoscope assignment unit 126 assigns: the endoscope G-R-1 with endoscope No. 1 to the examination E9; the endoscope G-R-2 with endoscope No. 2 to the examination E10; and the endoscope G-R-3 with endoscope No. 3 to the examination E11. Also, the endoscope assignment unit 126 assigns the endoscope C-R-1 with endoscope No. 15 to the examination E12.

In this way, the endoscope assignment unit 126 can re-assign an endoscope, the cleaning of which is completed at the scheduled examination start time and the status of which is "under standby", to the examination. In other words, in the scheduling processing, the endoscope assignment unit 126 can assign the endoscope 30 to an endoscopic examination such that a time after the scheduled end time of cleaning by the cleaning machine 50, which is assigned to the endoscope 30 by the cleaning machine assignment unit 144, becomes a scheduled examination start time. Because the cleaning machine assignment unit 144 efficiently assigns the cleaning machine 50 to the endoscope 30 in the third time step, each of the endoscopes G-R-1, G-R-2, G-R-3, and C-R-1 is re-assigned to an examination to be started after the scheduled cleaning end time of each of them, thereby enabling efficient scheduling of the endoscopes 30.

In S20, the cleaning machine assignment unit 144 assigns: the first cleaning machine 50a to the endoscope G-R-1 for the examination E9; the second cleaning machine 50b to the endoscope G-R-2 for the examination E10; the third cleaning machine 50c to the endoscope G-R-3 for the examination E11; and the first cleaning machine 50a to the endoscope C-R-1 for the examination E12. The cleaning machine assignment unit 144 sets: the scheduled cleaning start times of the endoscopes G-R-1, G-R-2, and G-R-3 to be 9:50; the scheduled cleaning end times thereof to be 10:10; the scheduled cleaning start time of the endoscope C-R-1 to be 10:10; and the scheduled cleaning end time thereof to be 10:30.

Figure 17:
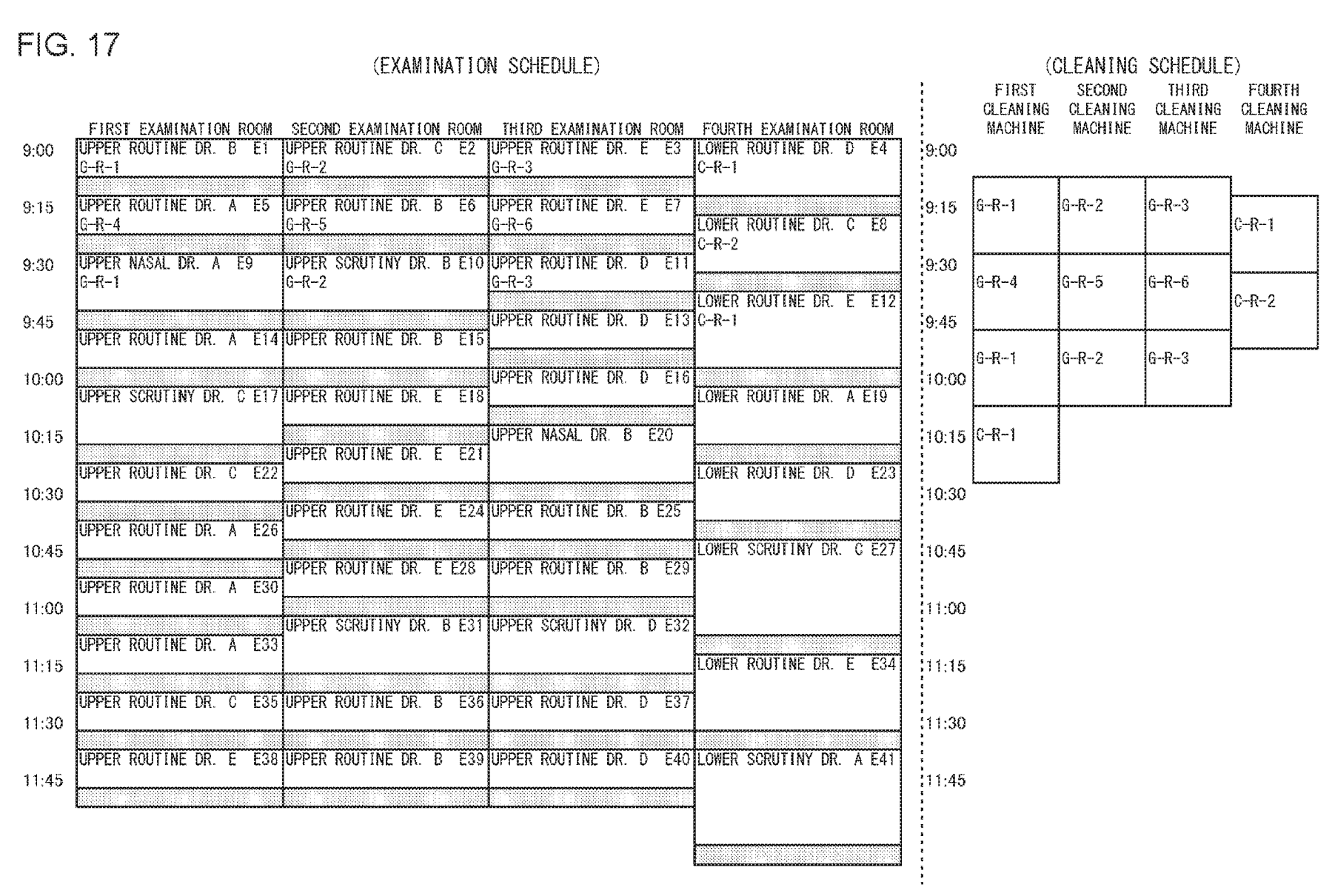

FIG. 17 illustrates an examination schedule generated by the examination schedule management unit 110 and a cleaning schedule generated by the cleaning schedule management unit 130. Herein, the results of the assignment by the endoscope specification unit 124 are reflected in the examination schedule, and those of the assignment by the cleaning machine assignment unit 144 are reflected in the cleaning schedule.

As illustrated in the examination schedule, the scheduled examination end time of the examination E12 in which the endoscope C-R-1 is to be used is 10:00, on the other hand, according to the cleaning schedule of the fourth cleaning machine 50d, the fourth cleaning machine 50d is available after 9:55. Therefore, the cleaning machine assignment unit 144 can assign, from 10:00, the fourth cleaning machine 50d to the endoscope C-R-1 for the examination E12, but a 5-minute unused time occurs with the fourth cleaning machine 50d, and hence the cleaning machine assignment unit 144 assigns the first cleaning machine 50a to the endoscope C-R-1.

<Fourth Time: S16 to S20>

In S16, the examination extraction unit 122 extracts: an examination E14 from the first examination room 20a; an examination E15 from the second examination room 20b; an examination E13 from the third examination room 20c; and an examination E19 from the fourth examination room 20d. Herein, when the step of S34 in FIG. 8 is executed, the scheduled examination start time (10:00) of the examination E16 next to the examination E13 in the third examination room 20c is earlier than the scheduled examination start time (10:05) of the examination E19 in the fourth examination room 20d (S34/N). That is, the examination E19 extracted from the fourth examination room 20d is started after the examination E16 in the third examination room 20c that is not yet extracted. Therefore, the examination extraction unit 122 determines that an endoscope should not be assigned to the examination E19 before the examination E16, and excludes the examination E19 from the examinations to which endoscopes are to be assigned (S38). The examinations E13, E14, and E15 are specified as the examinations to which the endoscopes 30 are to be assigned.

In S18, the endoscope specification unit 124 determines the endoscopes with endoscope Nos. 7 to 14, which are endoscopes for upper examination, as candidate endoscopes for the examination E13 whose scheduled examination start time is 9:45. At this scheduled examination start time (9:45), the statuses of the endoscopes with endoscope Nos. 1 to 3 are "used", and those of the endoscopes with endoscope Nos. 4 to 6 are "under cleaning", and hence they do not become candidate endoscopes for the examination E13. Also, the endoscope specification unit 124 determines the endoscopes with endoscope Nos. 4 to 14, which are endoscopes for upper examination, as candidate endoscopes for the examinations E14 and E15 whose scheduled examination start times are 9:50. At this scheduled examination start time (9:50), the statuses of the endoscopes with endoscope Nos. 1 to 3 are "under cleaning", and hence they do not become candidate endoscopes for the examination E13. The specified candidate endoscopes are notified to the endoscope specification unit 124.

In response to the notice from the endoscope specification unit 124, the endoscope assignment unit 126 assigns: an endoscope G-H-1 with endoscope No. 7 to the examination E13; the endoscope G-R-4 with endoscope No. 4 to the examination E14; and the endoscope G-R-5 with endoscope No. 5 to the examination E15. The endoscopes G-R-4 and G-R-5 are re-assigned to examinations after being cleaned at 9:50.

In S20, the cleaning machine assignment unit 144 assigns: the fourth cleaning machine 50d to the endoscope G-H-1 for the examination E13; the second cleaning machine 50b to the endoscope G-R-4 for the examination E14; and the third cleaning machine 50c to the endoscope G-R-5 for the examination E15. The cleaning machine assignment unit 144 sets: the scheduled cleaning start time of the endoscope G-H-1 to be 9:55; the scheduled cleaning end time thereof to be 10:15; the scheduled cleaning start times of the G-R-4 and G-R-5 to be 10:10; and the scheduled cleaning end times thereof to be 10:30.

FIG. 18 illustrates an examination schedule generated by the examination schedule management unit 110 and a cleaning schedule generated by the cleaning schedule management unit 130. Herein, the results of the assignment by the endoscope specification unit 124 are reflected in the examination schedule, and those of the assignment by the cleaning machine assignment unit 144 are reflected in the cleaning schedule.

FIG. 19 illustrates an individual schedule of the endoscope 30. In this way, individual schedule information on the endoscope 30 are generated as illustrated in FIG. 19 by repeating four times S16 to S20 of the basic flowchart.

As described above, the processing of S16 to S20 is repeated until the assignment processing for the last examination is completed. FIG. 20 illustrates an examination schedule generated by the examination schedule management unit 110 and a cleaning schedule generated by the cleaning schedule management unit 130. Herein, the results of the assignment by the endoscope specification unit 124 are reflected in the examination schedule, and those of the assignment by the cleaning machine assignment unit 144 are reflected in the cleaning schedule. As described above, the processing for generating the schedule information on the endoscope 30 is completed when the assignment of the endoscopes 30 to all the examinations is completed and when the assignment of the cleaning machines 50 to the endoscopes 30 is completed.

Figure 21:
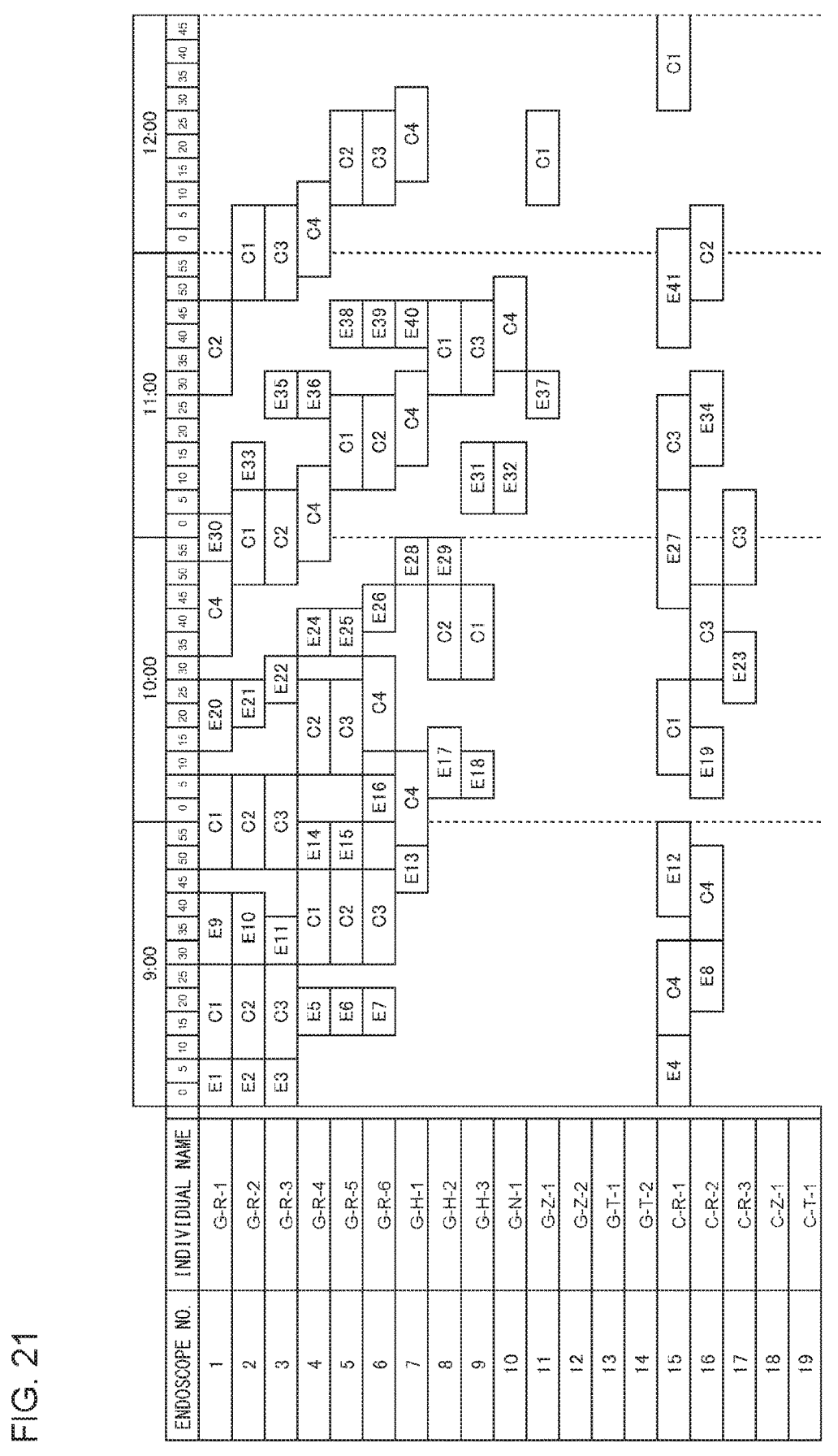

FIG. 21 illustrates an individual schedule of the endoscopes 30 for one day. The results of the assignment of the endoscopes 30 by the endoscope assignment unit 126 and/or the results of the assignment of the cleaning machines 50 by the cleaning machine assignment unit 144 are displayed on the display of the terminal device 12 by the display processing unit 150. For example, the display processing unit 150 may read the examination schedule information from the examination schedule holding unit 206 and display the examination schedule table illustrated in FIG. 20 on the terminal device 12. Also, the display processing unit 150 may read the cleaning schedule information from the cleaning schedule holding unit 208 and display the cleaning schedule table illustrated in FIG. 20 on the terminal device 12. Also, the display processing unit 150 may display the examination schedule table and the cleaning schedule table on the same screen. As a result, a doctor and a person preparing for examination can easily recognize which endoscope 30 is to be used in an examination, and a person preparing for examination can easily recognize which cleaning machine 50 is to be used for the cleaning of the used endoscope 30.

Also, the display processing unit 150 may read the examination schedule information from the examination schedule holding unit 206 and read the cleaning schedule information from the cleaning schedule holding unit 208, and may display the individual schedule table of the endoscopes 30 on the terminal device 12. This individual schedule table is illustrated in FIG. 21, and by generating such an individual schedule table, a person preparing for examination can understand the schedule of each individual of the endoscope 30. In the case of wanting to understand the situation of the endoscope 30 at a certain time, a person preparing for examination can understand, by the individual schedule table, the situation such as whether the endoscope 30 is under cleaning or under use in an examination.

As illustrated in FIG. 21, the endoscope C-R-1 is scheduled to be under cleaning between 12:30 and 12:50. Depending on a medical facility, if the lunch break of persons preparing for examination is defined to be, for example, between 12:30 and 13:30, it may be notified that this cleaning processing is performed outside working hours.

The end time determination unit 146 determines whether, as a result of the assignment of the cleaning machine 50 to the endoscope 30 by the cleaning machine assignment unit 144, the scheduled cleaning end time is after a reference time (12:30). When it is determined by the end time determination unit 146 that the scheduled cleaning end time is after the reference time, the cleaning machine assignment availability confirmation unit 148 may transmit a notice to a user (e.g., an operator) to confirm whether the cleaning machine assignment is permitted. For example, the timing of this notification may be after the assignment processing of the endoscopes 30 is completed for all the examinations. With reference to FIG. 21, the scheduled cleaning end time of the endoscope G-H-1 is 12:35, and hence also with respect to this cleaning schedule, the cleaning machine assignment availability confirmation unit 148 confirms to a user the availability of cleaning machine assignment.

Schedules of doctors are determined by the examination order, and a doctor grasps the scheduled start time and the examination room, etc., of the next examination according to the examination schedule table. Similarly, the information management device 10 may set a schedule to a person preparing for examination. In this schedule, it may be set that a person preparing for examination brings the endoscope 30 into the examination room 20 before the start of an examination and brings the endoscope 30 into the cleaning room 40 after the end of the examination, etc., and it also may be set that he/she assists an examination in an examination room, etc.

Hereinafter, various aspects related to the scheduling processing by the information management device 10 of the embodiment will be described.

Example 1

In the embodiment, the endoscope specification unit 124 specifies an available endoscope 30 based on the examination type information on an endoscopic examination to be an assignment target, in the endoscope retrieval processing illustrated in FIG. 11. At this time, the examination type is distinguished depending on whether it is an upper examination or a lower examination, but in Example 1, the endoscope specification unit 124 specifies an available endoscope 30 based on the examination type information indicating more detailed examination contents.

FIG. 22 illustrates an endoscope order table held in an endoscope order holding unit 204. The endoscope order table records endoscope models to be preferentially assigned to the examination types by associating them with each other. Herein, the "preferential endoscope model 1" means information on the models to be assigned most preferentially, and the "preferential endoscope model 2" means information on the models to be assigned with the second highest priority. If an endoscope 30 designated by the "preferential endoscope model 1" is "under standby", the endoscope specification unit 124 specifies the endoscope 30 as a candidate endoscope. On the other hand, if an endoscope 30 designated by the "preferential endoscope model 1" is not "under standby" and an endoscope 30 designated by the "preferential endoscope model 2" is "under standby", the endoscope specification unit 124 specifies the endoscope 30 designated by the "preferential endoscope model 2" as a candidate endoscope. As described above, the endoscope order holding unit 204 holds the priority of the models of the endoscope 30 to be assigned to the examination types of endoscopic examinations, and the endoscope specification unit 124 specifies the endoscope 30 of a model with higher priority as a candidate endoscope.

Figure 23:
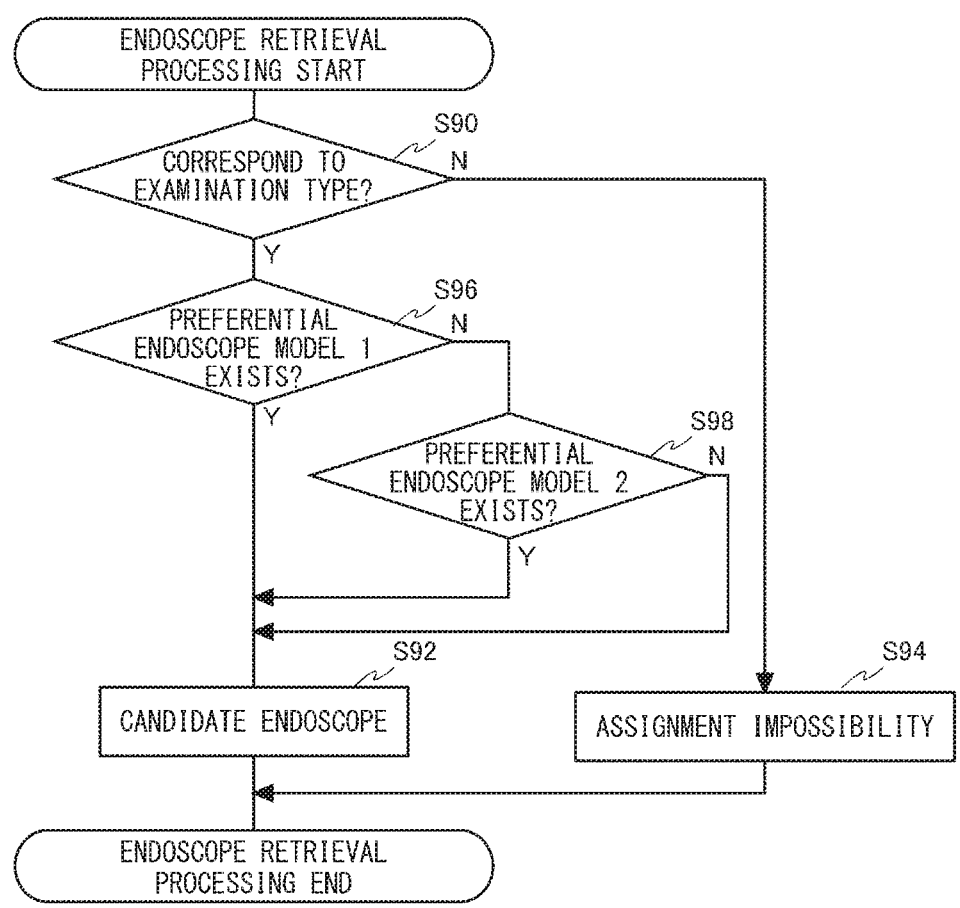
FIG. 23 is a view illustrating a detailed flowchart of the endoscope retrieval processing in Example 1.

FIG. 23 illustrates a detailed flowchart of endoscope retrieval processing in Example 1. The endoscope specification unit 124 performs retrieval processing on all the endoscopes 30 whose statuses are "under standby." The endoscope specification unit 124 specifies an available endoscope 30 based on the examination type information on the endoscopic examination to be an assignment target. In S90, when the examination type information on an examination indicates an upper examination, it is determined that an endoscope for upper examination corresponds and an endoscope for lower examination does not correspond. Similarly, when the examination type information on an examination indicates a lower examination, it is determined that an endoscope for lower examination corresponds and an endoscope for upper examination does not correspond.

When the first time steps of S16 to S20 in the embodiment are described, the endoscope specification unit 124 determines that the endoscopes with endoscope Nos. 1 to 14, which are endoscopes for upper examination, correspond to the examinations E1, E2, and E3; and determines that the endoscopes with endoscope Nos. 15 to 19, which are endoscopes for lower examination, correspond to the examination E4 (S90).

The examination types of the examinations E1, E2, and E3 are "upper routine examination", and the endoscope specification unit 124 recognizes that a model with the highest priority (preferential endoscope model 1) is an "upper routine model", by referring to the endoscope order information held in the endoscope order holding unit 204. Therefore, the endoscope specification unit 124 determines whether an "upper routine model" is included in the corresponding endoscopes (S96). In this case, the endoscopes with endoscope Nos. 1 to 6 exist as an upper routine model (S96/Y), and hence the endoscope specification unit 124 determines the endoscopes with endoscope Nos. 1 to 6 as candidate endoscopes (S92).

The examination type of the examinations E4 is a "lower routine examination", and the endoscope specification unit 124 recognizes that a model with the highest priority (preferential endoscope model 1) is a "lower routine model", by referring to the endoscope order information held in the endoscope order holding unit 204. Therefore, the endoscope specification unit 124 determines whether a "lower routine model" is included in the corresponding endoscopes (S96). In this case, the endoscopes with endoscope Nos. 15 to 17 exist as a lower routine model (S96/Y), and hence the endoscope specification unit 124 determines the endoscopes with endoscope Nos. 15 to 17 as candidate endoscopes (S92).

With respect to the examinations E1 to E3, if the endoscope of the preferential endoscope model 1 is not included in the corresponding endoscopes (S96/N), the endoscope specification unit 124 recognizes that the model with the second highest priority (preferential endoscope model 2) is an "upper high image quality mode 1", by referring to the endoscope order information held in the endoscope order holding unit 204. Therefore, the endoscope specification unit 124 determines whether an "upper high image quality model" is included in the corresponding endoscopes (S98), and if it is included (S98/Y), the endoscope specification unit 124 determines the endoscope of an upper high image quality model as a candidate endoscope (S92).

If the endoscope of the preferential endoscope model 2 is not included in the corresponding endoscopes (S98/N), the endoscope specification unit 124 determines, of the endoscopes determined to correspond to the examination type in S90, an endoscope of a model other than the preferential endoscope models as a candidate endoscope (S92). The endoscope specification unit 124 notifies the endoscope assignment unit 126 of the specified candidate endoscope, and the endoscope assignment unit 126 assigns the endoscope 30 to an examination, as described in the embodiment.

When the endoscope specification unit 124 specifies an endoscope 30 of low priority model and the endoscope assignment unit 126 intends to assign the specified endoscope to an endoscopic examination, it is preferable that the endoscope assignment availability confirmation unit 128 confirms to a user the availability of endoscope assignment. For example, when the preferential endoscope model 1 is not assigned, the endoscope assignment availability confirmation unit 128 may perform confirmation to a user assuming that a model with low priority is assigned, but when the model set by the endoscope order holding unit 204 is assigned (e.g., when the preferential endoscope model 2 is assigned), the endoscope assignment availability confirmation unit 128 may not perform confirmation to a user. That is, only when the endoscope specification unit 124 determines a model other than the preferential endoscope models as a candidate endoscope and the endoscope assignment unit 126 assigns the candidate endoscope to an examination, the endoscope assignment availability confirmation unit 128 may be caused to confirm to a user the availability of the endoscope assignment. When the endoscope specification unit 124 cannot determine the preferential endoscope model as a candidate endoscope (S98/N), the endoscope specification unit 124 may determine that there is no candidate endoscope and the endoscope assignment availability confirmation unit 128 may notify a user of the fact.

The timing of this confirmation may be after the assignment processing of the endoscopes 30 is completed for all the examinations. Before the endoscopic examination work for one day starts, at least a user needs to recognize that there is an examination to which a proper endoscope 30 is not assigned.

When the embodiment and Example 1 are compared with each other, for example, the endoscope G-R-1 that is an upper routine model is assigned to the examination E9 that is an upper nasal examination in the embodiment, as illustrated in FIG. 17. According to Example 1, however, the endoscope specification unit 124 recognizes that the model with the highest priority (preferential endoscope model 1) for the examination E9 is an "upper nasal model", by referring to the endoscope order information held in the endoscope order holding unit 204, thereby allowing the endoscope specification unit 124 to specify the endoscope G-N-1 with endoscope No. 10 as a candidate endoscope for the examination E9. Similarly, the endoscope specification unit 124 specifies the endoscopes G-H-1 to G-H-3 with endoscope Nos. 7 to 9, which are upper high image quality models, as candidate endoscopes for the examination E10 that is an upper scrutiny examination. Therefore, the endoscope assignment unit 126 assigns the endoscope G-N-1 to the examination E9 and the endoscope G-H-1 to the examination E10. In comparison with the embodiment as described above, an endoscope 30 with higher priority, that is, an endoscope 30 suitable for an examination can be assigned to an endoscopic examination in Example 1, and hence the degree of perfection of the examination schedule can be enhanced.

Example 2

In the endoscopic examination work support system 1, an endoscope in which wear or aging has progressed is likely to cause functional deterioration or a malfunction. The case where the wear or aging of an endoscope progresses prominently occurs generally when the number of times of use and the use time of the endoscope are extremely larger and longer than other endoscopes, and hence in Example 2, it is aimed that the number of times of use and the use time of a plurality of endoscopes 30 are equalized.

Returning to FIG. 3, the usage condition storage unit 224 stores the past usage conditions of a plurality of the possessed endoscopes 30. FIG. 24 illustrates a usage condition table stored in the usage condition storage unit 224. The usage condition table records the past usage condition by associating with each endoscope 30. These usage condition is absolutely a thing of the past, and updated when the endoscope 30 is actually used. Herein, the usage condition means the "number of times of use" and "use time", and the "number of times of use" indicates the cumulative number of times used in examinations, and the "use time" indicates the cumulative time used in examinations.

Referring to FIG. 1, the endoscope 30 is connected to the endoscopic observation device 22 when an examination is started, and at this time the identification information on the endoscope 30 (endoscope ID) is transmitted to the information management device 10 via the network 2. When an examination end button is operated (or when the endoscope 30 is withdrawn from the endoscopic observation device 22) in the endoscopic observation device 22 at the end of an examination, a notice of end of the examination is transmitted to the information management device 10. In the information management device 10, the usage condition monitoring unit 160 monitors the information transmitted from the endoscopic observation device 22, and derives the time between the transmission of the endoscope ID and the transmission of the notice of end of examination as an examination use time. When the notice of end of examination is transmitted, the usage condition monitoring unit 160 updates the usage condition table by increasing the number of times of use of the corresponding endoscope 30 in the usage condition table by 1 and by adding the currently derived examination use time to the use time, and records them in the usage condition storage unit 224. The usage condition table is generated as described above.

The usage condition table illustrated in FIG. 24 is an example illustrated for ease of understanding. In FIG. 24, for example, the numbers of times of use and the use times of the upper routine models with endoscope Nos. 1 to 6 are greatly different, and in Example 2, a technique for leveling (equalizing) the numbers of times of use and the use times of a plurality of endoscopes is presented in order to prevent such a situation from occurring. Therefore, please note that the usage condition table illustrated in FIG. 24 is merely an example of the usage conditions.

In Example 2, when there are a plurality of endoscopes 30 that can be assigned to the respective endoscopic examinations managed by the examination schedule management unit 110, the endoscope assignment unit 126 preferentially assigns the endoscope 30, the past number of times of use or past use time of which is relatively small or short, to an endoscopic examination by referring to the usage conditions stored in the usage condition storage unit 224.

Figure 25:
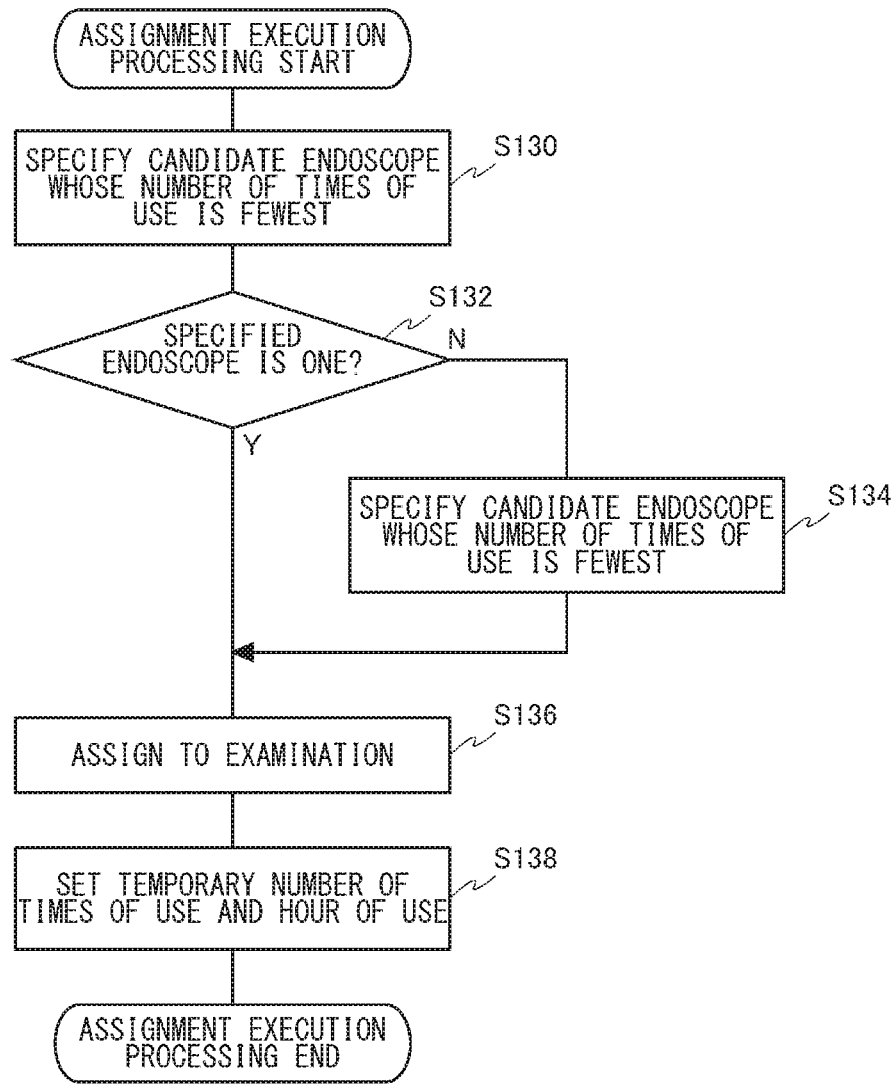
FIG. 25 is a view illustrating a detailed flowchart of S56 of the endoscope assignment processing illustrated in FIG. 9.

FIG. 25 illustrates a detailed flowchart of S56 in the endoscope assignment processing illustrated in FIG. 9. The endoscope assignment unit 126 specifies, of the candidate endoscopes notified from the endoscope specification unit 124, the candidate endoscope whose past number of times of use is smallest, by referring to the usage conditions stored in the usage condition storage unit 224 (S130).

Hereinafter, an example will be described, in which candidate endoscopes for the examinations E1, E2, and E3 are specified by the endoscope retrieval processing described in Example 1. In Example 1, the endoscope specification unit 124 specifies the endoscope with endoscope Nos. 1 to 6 as the candidate endoscopes for the examinations E1, E2, and E3, and notifies the endoscope assignment unit 126.

The endoscope assignment unit 126 specifies, of the endoscopes with endoscope Nos. 1 to 6, the endoscope G-R-3 with endoscope No. 3 for the examination E1 and as the endoscope whose number of times of use is smallest, by referring to the usage conditions of the endoscopes with endoscope Nos. 1 to 6 stored in the usage condition storage unit 224 (S130). The number of times of use of the endoscope G-R-3 is 40, which is relatively smaller than those of the endoscopes G-R-1, G-R-2, G-R-4, G-R-5 and G-R-6, and there is no other endoscope whose number of times of use is 40 (S132/Y), and hence the endoscope assignment unit 126 assigns the endoscope G-R-3 to the examination E1 (S136). The endoscope assignment unit 126 contributes to equalization of the numbers of times of use of the endoscopes by preferentially assigning G-R-3 whose number of times of use is smallest to the examination E1.

When having assigned an endoscope to an examination, the endoscope assignment unit 126 sets the temporary number of times of use and use time (temporary usage condition) as the usage condition of the endoscope (S138). In this case, the number of times of use of the endoscope with endoscope No. 3 is temporarily increased by 1, and the use time is temporarily increased by 10 minutes (scheduled examination time of an upper routine examination is 10 minutes) by referring to the examination type master table 210 illustrated in FIG. 5. As a result, the temporary number of times of use of the endoscope with endoscope No. 3 becomes "41", and the temporary use time becomes "660 minutes." This temporary usage condition will be used later in the assignment execution processing illustrated in FIG. 25.

The temporary number of times of use and use time are not reflected in the usage condition table in the usage condition storage unit 224. The temporary usage condition is set only for the purpose of scheduling the endoscope 30, and may be discarded when the scheduling of the endoscopes 30 is completed for all the examinations.

Next, the endoscope assignment unit 126 specifies, of the endoscopes with endoscope Nos. 1, 2, and 4 to 6, the endoscope G-R-2 with endoscope No. 2 and the endoscope G-R-4 with endoscope No. 4 for the examination E2 and as the endoscopes whose numbers of times of use are smallest, by referring to the usage conditions of the endoscopes with endoscope Nos. 1, 2, and 4 to 6 stored in the usage condition storage unit 224 (S130). The numbers of times of use of the endoscopes G-R-2 and G-R-4 are 50, which is relatively smaller than those of the endoscopes G-R-1, G-R-5, and G-R-6, and two endoscopes, the numbers of times of use of which are equal to each other, are specified (S132/N). Herein, the endoscope assignment unit 126 specifies, of the two endoscopes, the endoscope G-R-2 with endoscope No. 2 as the endoscope whose use time is shortest, by referring to the endoscope usage conditions of the endoscopes with endoscope Nos. 2 and 4 stored in the usage condition storage unit 224 (S134), and assigns the endoscope G-R-2 to the examination E2 (S136). The endoscope assignment unit 126 contributes to equalization of the use times of endoscopes by preferentially assigning, of the candidate endoscopes, G-R-2 whose number of times of use is smallest and whose use time is shortest to the examination E2. The endoscope assignment unit 126 sets the temporary number of times of use and use time (temporary usage condition) as the usage condition of the endoscope with endoscope No. 2 (S138). That is, the temporary number of times of use of the endoscope with endoscope No. 2 becomes "51", and the temporary use time becomes "510 minutes."

Next, the endoscope assignment unit 126 specifies, of the endoscopes with endoscope Nos. 1 and 4 to 6, the endoscope G-R-4 with endoscope No. 4 for the examination E3 and as the endoscope whose number of times of use is smallest, by referring to the usage conditions of the endoscopes with endoscope Nos. 1 and 4 to 6 stored in the usage condition storage unit 224 (S130). The number of times of use of G-R-4 is 50, which is relatively smaller than those of the endoscopes G-R-1, G-R-5, and G-R-6, and hence the endoscope assignment unit 126 assigns the endoscope G-R-4 to the examination E3 (S136). The endoscope assignment unit 126 contributes to equalization of the numbers of times of use of endoscopes by preferentially assigning, of the candidate endoscopes, G-R-4 whose number of times of use is smallest to the examination E3. The endoscope assignment unit 126 sets the temporary number of times of use and use time (temporary usage condition) as the usage condition of the endoscope with endoscope No. 4 (S138).

As described above, when there are a plurality of the endoscopes 30 that can be assigned to respective endoscopic examinations, the endoscope assignment unit 126 preferentially assigns the endoscope 30, the past number of times of use or past use time of which is relatively small or short, to an endoscopic examination by referring to the usage condition stored in the usage condition storage unit 224, thereby contributing to equalization of the numbers of times of use or use times. In FIG. 25, a candidate endoscope whose number of times of use is smallest is specified in S130, and a candidate endoscope whose use time is shortest is specified in S134, but this order may be reversed. When there are a plurality of candidate endoscopes whose numbers of times of use and use times are equal to each other, the endoscope assignment unit 126 may assign any one of them to an endoscopic examination.

In the above Examples 1 and 2, the modes of assigning the endoscope 30 in an examination schedule has been described. In the following Examples 3, the modes of assigning the cleaning machine 50 in a cleaning schedule will be described.

Example 3

Returning to a FIG. 3, the cleaning machine order holding unit 226 holds the priority of the cleaning machines 50 to be assigned to the endoscopes 30. FIG. 26 illustrates a cleaning machine order table held in the cleaning machine order holding unit 226. The cleaning machine order table records the priority of the cleaning machines 50 to be assigned, by associating with the endoscopes 30. In this cleaning machine order table, the respective endoscopes are recorded along the vertical axis and the respective cleaning machines are along the horizontal axis, and priority is set for the combinations of the endoscopes and the cleaning machines. In this example, it is assumed that: the first cleaning machine 50*a* and the second cleaning machine 50*b* use a medicinal solution A; the third cleaning machine 50*c* uses a medicinal solution B; and the fourth cleaning machine 50*d* uses a medicinal solution C. In the cleaning machine order table, the priority of the cleaning machines 50 to be assigned may be associated with the endoscope models, instead of the endoscope individuals.

In Example 3, the model of the first cleaning machine 50*a* and that of the second cleaning machine 50*b* may or may not be the same as each other. The first and second cleaning machines 50*a* and 50*b*, the third cleaning machine 50*c*, and the fourth cleaning machine 50*d* use different medicinal solutions, and therefore these models are different from each other. In the case where a plurality of the cleaning machines 50 are formed by different models in this way, the cleaning machine order holding unit 226 holds the priority of the cleaning machine models.

In the cleaning machine order table illustrated in FIG. 26, a set value 1 indicates that the priority is the highest, and a set value 2 indicates that the priority is the second highest. A set value 3 indicates that the priority is the third highest. A set value 0 indicates that assignment to the endoscope 30 is prohibited.

In the cleaning machine order table illustrated in FIG. 26, the set value 0 is provided to the fourth cleaning machine 50*d* that uses the medicinal solution C. This is because there is a situation in which: for example, the medicinal solution C has a strong attack property by which an endoscope member is likely to be deteriorated, and hence the use of it for cleaning many endoscopes 30 is prohibited in medical facilities. In this example, the set value 2 is provided for the upper treatment models G-T-1 and G-T-2 and the lower treatment model C-T-1, but the set value 0 is provided for the other endoscopes, which prohibits the use for the endoscopes. The medicinal solution C may be, for example, strongly acidic electrolyzed water.

In the example illustrated in FIG. 26, the priority of the cleaning machines 50 to be assigned is thus set based on the attack property of a medicinal cleaning solution to be used in the cleaning machine 50. A cleaning machine order table is appropriately generated according to the policy of a medical facility, and long life of the endoscope 30 can be expected by generating the cleaning machine order table depending on the strength of an attack property.

On the other hand, for example, strongly acidic electrolyzed water has the merit that it is very inexpensive as a medicinal cleaning solution. Therefore, according to a policy focused on the cost of a medicinal solution, it is also possible to provide a set value other than the set value 0 to the cleaning machine 50 that uses strongly acidic electrolyzed water. Thus, the priority of the cleaning machines 50 held in the cleaning machine order holding unit 226 is set based on a medicinal solution to be used in the cleaning machine 50.

Figure 27:
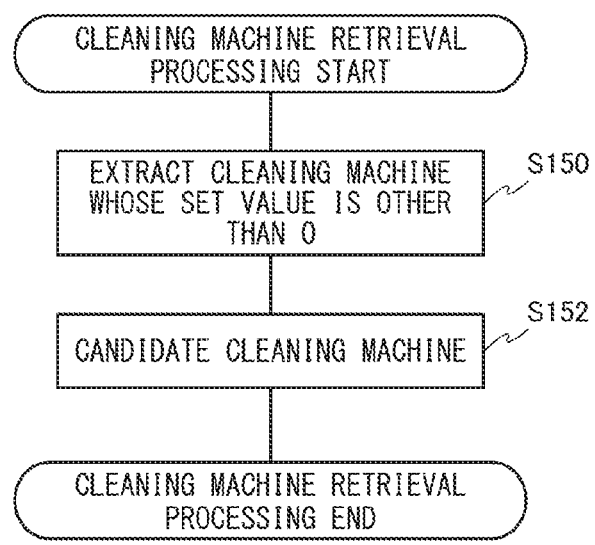
FIG. 27 is a view illustrating a detailed flowchart of S110 of the cleaning machine assignment processing illustrated in FIG. 13.

FIG. 27 illustrates a detailed flowchart of S110 in the cleaning machine assignment processing illustrated in FIG. 13. In S110, the cleaning machine specification unit 142 performs retrieval processing on the possessed cleaning machines 50 for the respective endoscopes 30 assigned by the endoscope assignment processing of S18 (see FIG. 7), and specifies an available cleaning machine 50.

Hereinafter, an example will be described, in which the endoscopes G-R-1, G-R-2, G-R-3 and C-R-1 are respectively assigned to the examinations E1, E2, E3 and E4 by the endoscope assignment processing described in the embodiment. That is, the cleaning machine assignment processing is started in the state where the examination schedule illustrated in FIG. 12 is set.

Returning to FIG. 3, in the second assignment processing unit 140, the cleaning machine specification unit 142 extracts the cleaning machines 50 whose set values are other than 0 for the endoscopes G-R-1, G-R-2, G-R-3, and C-R-1 by referring to the cleaning machine order information held in the cleaning machine order holding unit 226 (S150). In S150, cleaning machines 50, the use of which is not prohibited, are extracted. Herein, for the endoscopes G-R-1, G-R-2, and G-R-3, which are upper routine models, the set values of the first cleaning machine 50a, the second cleaning machine 50b, and the third cleaning machine 50c are not 0, and similarly, for the endoscope C-R-1, which is a lower routine model, the set values of the cleaning machine 50a, the second cleaning machine 50b, and the third cleaning machine 50c are not 0. Therefore, the cleaning machine specification unit 142 specifies the first cleaning machine 50a, the second cleaning machine 50b, and the third cleaning machine 50c as candidate cleaning machines for the respective examinations E1 to E4 (S152). The specified candidate cleaning machines are notified to the cleaning machine assignment unit 144.

Figure 28:
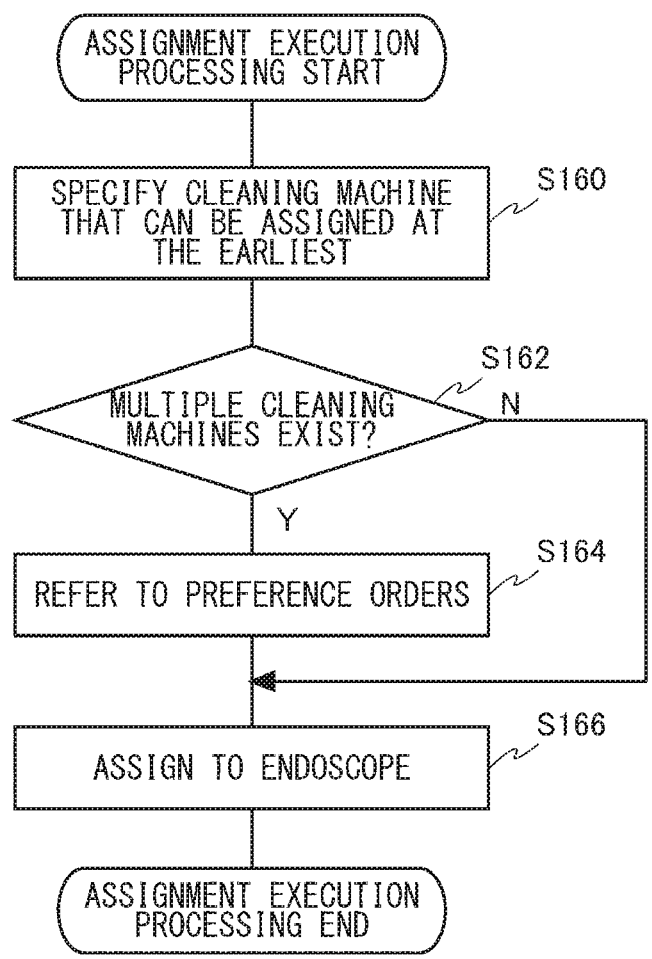
FIG. 28 is a view illustrating a detailed flowchart of S114 of the cleaning machine assignment processing illustrated in FIG. 13.

FIG. 28 illustrates a detailed flowchart of S114 in the cleaning machine assignment processing illustrated in FIG. 13. In S114, the cleaning machine assignment unit 144 assigns the cleaning machine 50 to the endoscope 30.

Initially, the cleaning machine assignment unit 144 assigns a cleaning machine to the endoscope G-R-1 for the examination E1. The cleaning machine assignment unit 144 specifies, of the candidate cleaning machines, the cleaning machine 50 that can be assigned earliest, by referring to the cleaning schedule held in the cleaning schedule holding unit 208 (S160). As described in the embodiment, when the cleaning machine specification unit 142 notifies the cleaning machine assignment unit 144 of a time zone when the candidate cleaning machine can be used, the cleaning machine assignment unit 144 may specify the cleaning machine 50 that can be assigned earliest by referring to the notified time zone.

Herein, the candidate cleaning machines, i.e., the first cleaning machine 50a, the second cleaning machine 50b, and the third cleaning machine 50c can be used in all the time zones in their initial states, that is, the statuses in all the time zones become "under standby". Then, the cleaning machine assignment unit 144 specifies that all of the first cleaning machine 50a, the second cleaning machine 50b, and the third cleaning machine 50c can be assigned earliest (S160), and determines that there are a plurality of cleaning machines that can be assigned earliest (S162/Y). Herein, the cleaning machine assignment unit 144 recognizes that the set value 1 is provided to the first cleaning machine 50a and the second cleaning machine 50b for the endoscope G-R-1 for the examination E1, by referring to the priority held in the cleaning machine order holding unit 226 (S164). Thereby, the cleaning machine assignment unit 144 assigns the first cleaning machine 50a to the endoscope G-R-1 (S166). In this way, the cleaning machine assignment unit 144 assigns the first cleaning machine 50a with high priority to the endoscope G-R-1, whereby it becomes possible to clean by a cleaning machine suitable for an endoscope. The scheduled cleaning start time is set to be 9:10 and the scheduled cleaning end time to be 9:30, which are registered in the cleaning schedule. Thereby, the status of the first cleaning machine 50a between 9:10 and 9:30 becomes "under use."

Next, the cleaning machine assignment unit 144 assigns a cleaning machine to the endoscope G-R-2 for the examination E2. The cleaning machine assignment unit 144 specifies, of the candidate cleaning machines, the cleaning machine 50 that can be assigned earliest, by referring to the cleaning schedule held in the cleaning schedule holding unit 208 (S160). Herein, the first cleaning machine 50a is set to be scheduled to be used between 9:10 and 9:30, and hence the cleaning machine assignment unit 144 specifies that the second cleaning machine 50b and the third cleaning machine 50c can be assigned earliest (S160), and determines that there are a plurality of cleaning machines that can be assigned earliest (S162/Y) Herein, the cleaning machine assignment unit 144 recognizes that the set value 1 is provided to the second cleaning machine 50b for the endoscope G-R-2 for the examination E2, by referring to the priority held in the cleaning machine order holding unit 226 (S164) Thereby, the cleaning machine assignment unit 144 assigns the second cleaning machine 50b to the endoscope G-R-2. Thus, the cleaning machine assignment unit 144 assigns the second cleaning machine 50b with high priority to the endoscope G-R-2. The scheduled cleaning start time is set to be 9:10 and the scheduled cleaning end time to be 9:30, which are registered in the cleaning schedule.

Next, the cleaning machine assignment unit 144 assigns a cleaning machine to the endoscope G-R-3 for the examination E3. The cleaning machine assignment unit 144 specifies, of the candidate cleaning machines, the cleaning machine 50 that can be assigned earliest, by referring to the cleaning schedule held in the cleaning schedule holding unit 208 (S160). Herein, the first cleaning machine 50a and the second cleaning machine 50b are set to be scheduled to be used between 9:10 and 9:30, and hence the cleaning machine assignment unit 144 specifies that the third cleaning machine 50c can be assigned earliest (S160), and determines that one cleaning machine 50 is specified (S162/N). Thereby, the cleaning machine assignment unit 144 assigns the third cleaning machine 50c to the endoscope G-R-3. The scheduled cleaning start time is set to be 9:10 and the scheduled cleaning end time to be 9:30, which are registered in the cleaning schedule.

With respect to the endoscope G-R-3, the setting value of the third cleaning machine 50c is 2, and hence the priority thereof is lower than those of the first cleaning machine 50a and the second cleaning machine 50b. Therefore, it is also possible to assign the first cleaning machine 50a or the second cleaning machine 50b to the endoscope G-R-3 at a time when the first cleaning machine 50a or the second cleaning machine 50b can be used. In such a case, however, the cleaning of the endoscope G-R-3 is delayed, which is not preferable from the viewpoint of working efficiency. Therefore, unless assignment is prohibited, the cleaning machine assignment unit 144 positively assigns the cleaning machine 50, even if the priority thereof is low.

Next, the cleaning machine assignment unit 144 assigns a cleaning machine to the endoscope C-R-1 for the examination E4. The cleaning machine assignment unit 144 specifies, of the candidate cleaning machines, the cleaning machine 50 that can be assigned earliest, by referring to the cleaning schedule held in the cleaning schedule holding unit 208 (S160). Herein, the first cleaning machine 50a, the second cleaning machine 50b, and the third cleaning machine 50c are set to be scheduled to be used between 9:10 and 9:30, and hence the cleaning machine assignment unit 144 specifies that all of the first cleaning machine 50a, the second cleaning machine 50b, and the third cleaning machine 50c can be assigned earliest (S160), and determines that there are a plurality of cleaning machines that can be assigned earliest (S162/Y).

Herein, the cleaning machine assignment unit 144 recognizes that the set value 1 is provided to the first cleaning machine 50a and the second cleaning machine 50b for the endoscope C-R-1 for the examination E4, by referring to the priority held in the cleaning machine order holding unit 226 (S164). Thereby, the cleaning machine assignment unit 144 assigns the first cleaning machine 50a to the endoscope C-R-1 (S166). In this way, the cleaning machine assignment unit 144 assigns the first cleaning machine 50a with high priority to the endoscope C-R-1, whereby it becomes possible to clean by a cleaning machine suitable for an endoscope. The scheduled cleaning start time is set to be 9:30 and the scheduled cleaning end time to be 9:50, which are registered in the cleaning schedule.

Figure 29:
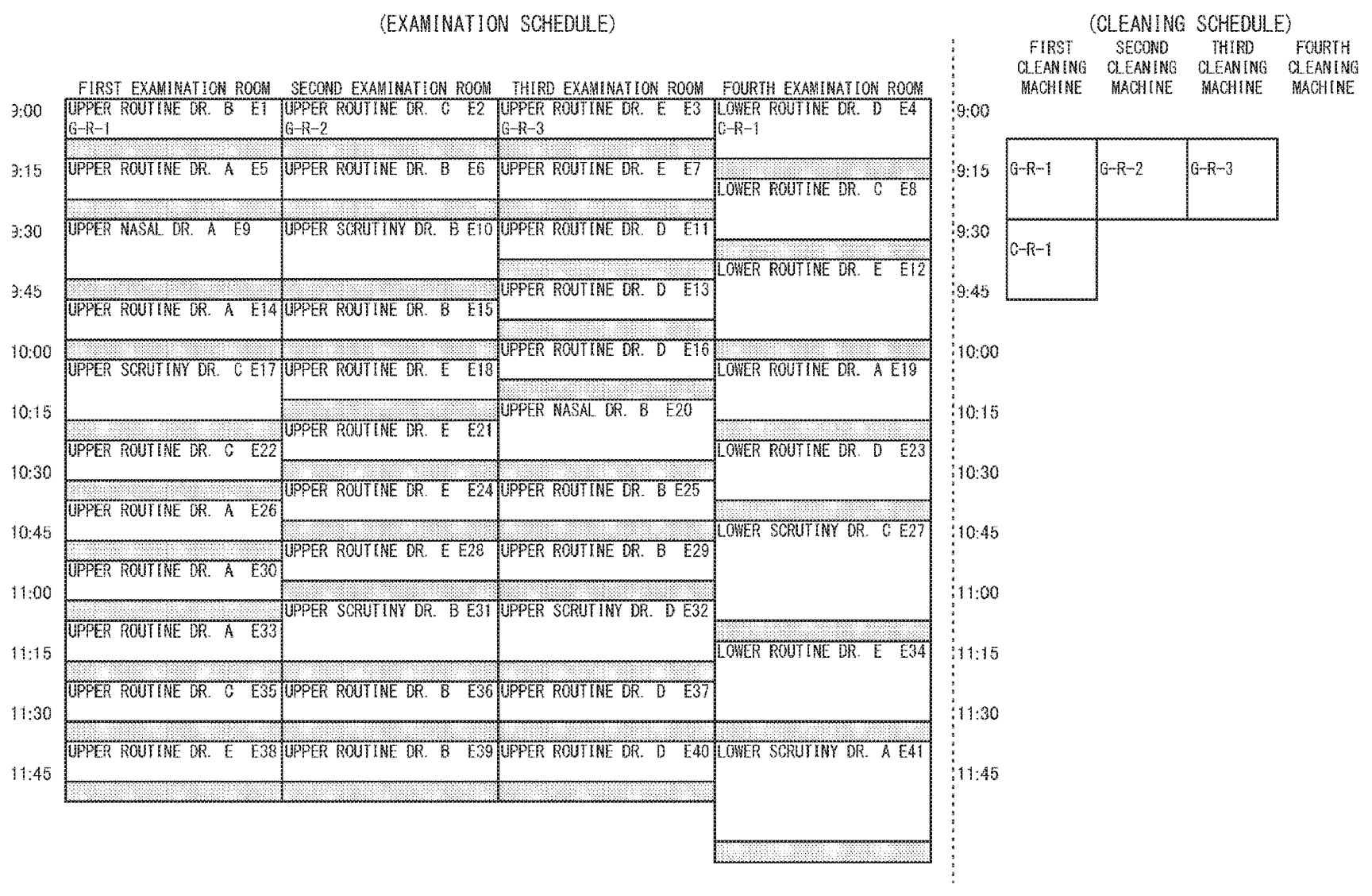

FIG. 29 illustrates a cleaning schedule generated by the cleaning schedule management unit 130 in Example 3. Herein, the results of the assignment by the cleaning machine assignment unit 144 are reflected in the cleaning schedule, and specifically it is registered that between 9:10 and 9:30: the endoscope G-R-1 is cleaned by the first cleaning machine 50a; the endoscope G-R-2 is cleaned by the second cleaning machine 50b; and the endoscope G-R-3 is cleaned by the third cleaning machine 50c, and registered that between 9:30 and 9:50 the endoscope C-R-1 is cleaned by the first cleaning machine 50a. The cleaning schedule management unit 130 records the updated cleaning schedule in the cleaning schedule holding unit 208.

When compared with FIG. 14 described in the embodiment, the fourth cleaning machine 50d is not used in the cleaning schedule illustrated in FIG. 29. This is because: the use of the fourth cleaning machine 50d, in other words, the use of the medicinal solution C is prohibited for the endoscope C-R-1, and hence a state where an endoscope cannot be assigned to the fourth cleaning machine 50d occurs. In FIG. 26, for the endoscopes G-T-1, G-T-2, and C-T-1, the set value of the fourth cleaning machine 50d is 2, and therefore the fourth cleaning machine 50d may be assigned in scheduling the cleaning of these endoscopes.

In the above description, the case where the use of the fourth cleaning machine 50d, the set value of which is 0 in the cleaning machine order holding unit 226, is prohibited has been described; however, the processing for generating a cleaning schedule may be performed by loosening this restriction. It is because, in the above processing in which the use of the fourth cleaning machine 50d is prohibited, it is assumed that a situation may occur in which: the fourth cleaning machine 50d is not usually used; the cleaning processing of the endoscopes 30 is not performed efficiently; and the number of the endoscopes 30 waiting for cleaning is increased. Therefore, on the cleaning machine 50 whose set value is 0, gentle restriction in which the assignment to the endoscope 30 is avoided as much as possible may be imposed, not severe restriction in which the assignment to the endoscope 30 is prohibited. The severe restriction and the gentle restriction may be determined according to, for example, a scheduling mode, and when the efficiency of the cleaning processing is intended to be promoted, a user may assign the cleaning machine 50 whose set value is 0 to the endoscope 30 by selecting the gentle restriction mode.

In this case, it is preferable that the usage condition storage unit 224 (or the later-described history recording unit 232) stores, for each endoscope 30, the number of times of cleaning by the cleaning machine 50 whose set value is 0. It is preferable that the cleaning machine assignment unit 144 assigns the cleaning machines 50 to the endoscopes 30 such that the number of times of cleaning by the cleaning machine 50 whose set value is 0 does not prominently become large, that is, such that the numbers of times of cleaning by the cleaning machines 50 whose set value are 0 become equal. An upper limit (e.g., 20 times) may be set to the number of times of cleaning by the cleaning machine 50 whose set value is 0, and the cleaning machine assignment unit 144 may not assign the cleaning machine 50 whose set value is 0 multiple times more than this upper limit.

Example 4

In Example 4, assignment processing is performed in scheduling the endoscope 30, in which a certain endoscope 30 is used by a specific doctor as much as possible. By making a set of the endoscope 30 and a doctor using it, it can be analyzed that, for example, an endoscope 30, the good condition of which is maintained for a long time, has been skillfully operated by a doctor frequently using it; on the other hand, it can also be analyzed that an endoscope 30, etc., which is likely to cause a malfunction, is problematically operated by a doctor frequently using it, etc.

Returning to a FIG. 3, the assigned endoscope information holding unit 228 holds preferential endoscope information on the endoscope preferentially assigned to a doctor. FIG. 30 illustrates a preferential endoscope table stored in the assigned endoscope information holding unit 228. In the preferential endoscope table, preferential endoscope information that define the priority of the endoscopes 30 to be assigned are recorded for each primary doctor of an endoscopic examination and for each endoscope model. Herein, the priority is provided on the premise that a medical facility possesses a plurality of endoscopes 30 of the same model, and the assigned endoscope information holding unit 228 holds, of the plurality of endoscopes 30 of the same model, the endoscopes to be preferentially assigned to doctors as preferential endoscope information. In FIG. 30, the "preferential endoscope 1" means an endoscope with assignment priority No. 1, the "preferential endoscope 2" means an endoscope with assignment priority No. 2, and the "preferential endoscope 3" means an endoscope with assignment priority No. 3.

For example, for a doctor A and with respect to an upper routine model, the assignment priority of the endoscope G-R-2 is set to be No. 1, and that of the endoscope G-R-1 to be No. 2. This preferential endoscope information is information by which a preferential endoscope is preferentially assigned to a doctor in the case where such an action can be taken, and a preferential endoscope should not necessarily be assigned to the doctor. For example, in an examination scheduled to be performed by the doctor A, if the statuses of the endoscopes G-R-2 and G-R-1 are not "under standby" at the scheduled examination start time, the endoscope assignment unit 126 assigns another upper routine model in order to prevent a delay in examinations.

In Example 4, the endoscope assignment unit 126 determines the endoscope 30 to be assigned to an endoscopic examination, based on the preferential endoscope information held in the assigned endoscope information holding unit 228 and the information on primary doctors of endoscopic examinations that the examination schedule management unit 110 manages.

Figure 31:
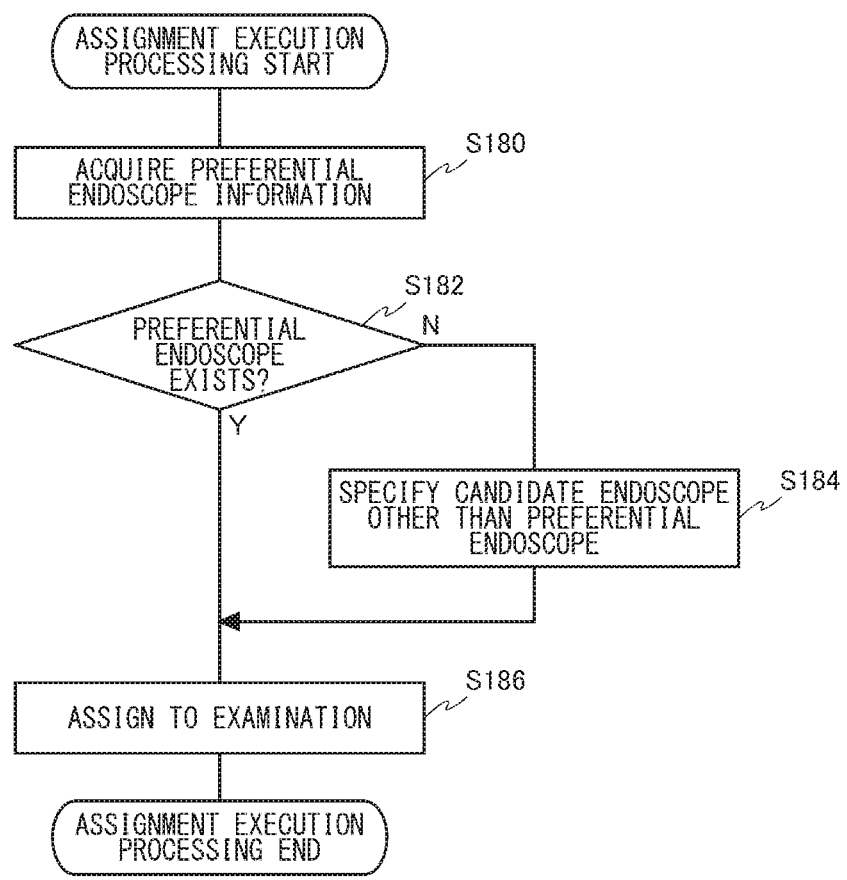
FIG. 31 is a view illustrating a detailed flowchart of S56 of the endoscope assignment processing illustrated in FIG. 9.

FIG. 31 illustrates a detailed flowchart of S56 in the endoscope assignment processing illustrated in FIG. 9. The endoscope assignment unit 126 acquires the preferential endoscope information held in the assigned endoscope information holding unit 228, based on a primary doctor of an endoscopic examination (S180).

Hereinafter, an example will be described, in which candidate endoscopes for the examinations E1, E2, E3, and E4 are specified by the endoscope retrieval processing described in Example 1. In Example 1, the endoscope specification unit 124 specifies the endoscopes with endoscope Nos. 1 to 6 as candidate endoscopes for the examinations E1, E2, and E3, and specifies the endoscopes with endoscope Nos. 15 to 17 as candidate endoscopes for the examination E4, and notifies the endoscope assignment unit 126.

The endoscope assignment unit 126 acquires, for each of the examinations E1, E2, E3, and E4, the preferential endoscope information on an endoscope model to be used from the assigned endoscope information holding unit 228, based on the primary doctor information on each of the examinations (S180).

With reference to the examination schedule of FIG. 4, the doctor B is a primary doctor of the examination E1, and the endoscope assignment unit 126 recognizes that: the preferential endoscope 1 of an upper routine model is G-R-3; the preferential endoscope 2 is G-R-1; and the preferential endoscope 3 is G-R-2, by referring to the preferential endoscope table. The doctor C is a primary doctor of the examination E2, and the endoscope assignment unit 126 recognizes that: the preferential endoscope 1 of an upper routine model is G-R-1; the preferential endoscope 2 is G-R-5; and the preferential endoscope 3 is G-R-4. The doctor E is a primary doctor of the examination E3, and the endoscope assignment unit 126 recognizes that: the preferential endoscope 1 of an upper routine model is G-R-5; the preferential endoscope 2 is G-R-6; and the preferential endoscope 3 is G-R-4. Also, the doctor D is a primary doctor of the examination E4, and the endoscope assignment unit 126 recognizes that the preferential endoscope 1 of a lower routine model is C-R-3.

With respect to the examination E1, the endoscope assignment unit 126 determines that the endoscope G-R-3, the preferential endoscope 1, is included in the candidate endoscopes with endoscope Nos. 1 to 6 (S182/Y), and therefore assigns the endoscope G-R-3 to the examination E1 (S186). Thereby, the doctor B can use the endoscope G-R-3 in the examination E1.

Next, with respect to the examination E2, the endoscope assignment unit 126 determines that the endoscope G-R-1, the preferential endoscope 1, is included in the candidate endoscopes with endoscope Nos. 1, 2, and 4 to 6 (S182/Y), and therefore assigns the endoscope G-R-1 to the examination E2 (S186). Thereby, the doctor C can use the endoscope G-R-1 in the examination E2.

Next, with respect to the examination E3, the endoscope assignment unit 126 determines that the endoscope G-R-5, the preferential endoscope 1, is included in the candidate endoscopes with endoscope Nos. 2 and 4 to 6 (S182/Y), and therefore assigns the endoscope G-R-5 to the examination E3 (S186). Thereby, the doctor E can use the endoscope G-R-5 in the examination E3.

Finally, with respect to the examination E4, the endoscope assignment unit 126 determines that the endoscope C-R-3, the preferential endoscope 1, is included in the candidate endoscopes with endoscope Nos. 15 to 17 (S182/Y), and therefore assigns the endoscope G-R-3 to the examination E4 (S186). Thereby, the doctor D can use the endoscope C-R-3 in the examination E4.

In this way, when there are a plurality of preferential endoscopes in candidate endoscopes, the endoscope assignment unit 126 assigns an endoscope with higher priority to an examination. When a preferential endoscope is not included in the candidate endoscopes, that is, when neither of the preferential endoscope 1, the preferential endoscope 2, and the preferential endoscope 3 is included (S182/N), the endoscope assignment unit 126 specifies a candidate endoscope other than the preferential endoscopes (S184), and assigns to an examination (S186). In this way, if there is no assignable preferential endoscope at the scheduled examination start time, it is preferable to assign another endoscope rather than to wait for the preferential endoscopes to become available, thereby allowing an efficient examination schedule to be generated. If there is no candidate endoscope, it is preferable to notify a user of the fact.

FIG. 32 illustrates an examination schedule updated by the examination schedule management unit 110. When the results of the assignment are notified from the endoscope assignment unit 126, the examination schedule management unit 110 registers the assigned endoscope 30 in the corresponding examination. Herein, it is registered that: the endoscope G-R-3 is used in the examination E1; the endoscope G-R-1 in the examination E2; the endoscope G-R-5 in the examination E3; and the endoscope C-R-3 in the examination E4. The examination schedule management unit 110 records the updated examination schedule in the examination schedule holding unit 206.

In Example 4, the endoscope assignment unit 126 preferentially assigns, as much as possible, a specific endoscope 30 to the examinations that a specific doctor takes charge of, and hence the use frequency of the endoscope 30 by the doctor becomes high.

The usage condition monitoring unit 160 monitors the usage condition of the endoscope 30 used in the actually performed endoscopic examinations, and records it in the history recording unit 232. As a result, the history recording unit 232 records the usage history information on the endoscope 30 used in the actual endoscopic examinations. With respect to the endoscope 30, the history recording unit 232 records the examination room where the endoscope 30 was used, doctor who used it, information on use date and time (examination start time, examination end time), identification information on the patient to whom it was used, examination type information, and the like, by associating them with each other. The history recording unit 232 does not need to record these information as usage history information on the endoscope 30, and may record the execution information in which the examination room where an endoscopic examination was performed, doctor, patient, and the endoscope 30, which are managed by the examination schedule management unit 110, are associated with each other.

The history recording unit 232 also records a history relating to a malfunction of the endoscope 30. For example, the malfunction history may include the doctor who operated when a malfunction occurred, examination type information, and information on date and time.

The display processing unit 150 displays, in a comparable format, the usage history information on a plurality of the endoscopes 30 recorded in the history recording unit 232. At this time, the display content derivation unit 152 calculates a statistical amount based on the usage history information recorded in the history recording unit 232. Herein, the statistical amount means the number of times of use of the endoscope 30, the use time thereof, or the like calculated for each doctor, and the display content derivation unit 152 has the function of deriving the statistical amount in accordance with the contents to be displayed. The display processing unit 150 displays the statistical amount calculated by the display content derivation unit 152.

The period designation unit 154 designates a period for the usage history information. This period is specified by an input by a user into an input frame provided on the screen of the terminal device 12. When the period designation unit 154 designates a period, the display content derivation unit 152 extracts the usage history information during the period from the history recording unit 232 and calculates a statistical amount to be displayed, and the display processing unit 150 displays the usage history information during the designated period, i.e., the statistical amount calculated by the display content derivation unit 152 on the display of the terminal device 12.

FIG. 33 illustrates one example of the usage history information to be displayed on the terminal device 12. When a user inputs the period between 2013/11/1 and 2014/10/30 as a display period, the period designation unit 154 designates this period, and the display content derivation unit 152 extracts the usage history information during this period from the history recording unit 232. Herein, the display content derivation unit 152 generates a number of times of use table by calculating the number of times of use of an upper routine model for each doctor, and the display processing unit 150 displays it on the display of the terminal device 12. The display content derivation unit 152 may calculate the number of times of malfunctions by generating a list of malfunction histories during this period, and the display processing unit 150 may collectively display the number of times of malfunctions and the malfunction histories.

With this number of times of use table, a user can specify an endoscope that caused less malfunctions and a doctor who frequently uses the endoscope. Conversely, a user can specify an endoscope that caused more malfunctions and a doctor who frequently uses the endoscope. As described above, the endoscope assignment unit 126 performs the endoscope assignment processing such that a specific doctor preferentially uses a specific endoscope, whereby the history information in which the endoscope 30 was actually used serves as useful information when failure analysis, etc., is performed. Additionally, because the display processing unit 150 displays the usage history information on a plurality of the endoscopes 30 in a comparable format, a user can recognize at a glance differences among the usage conditions of the endoscopes 30.

Figure 34:
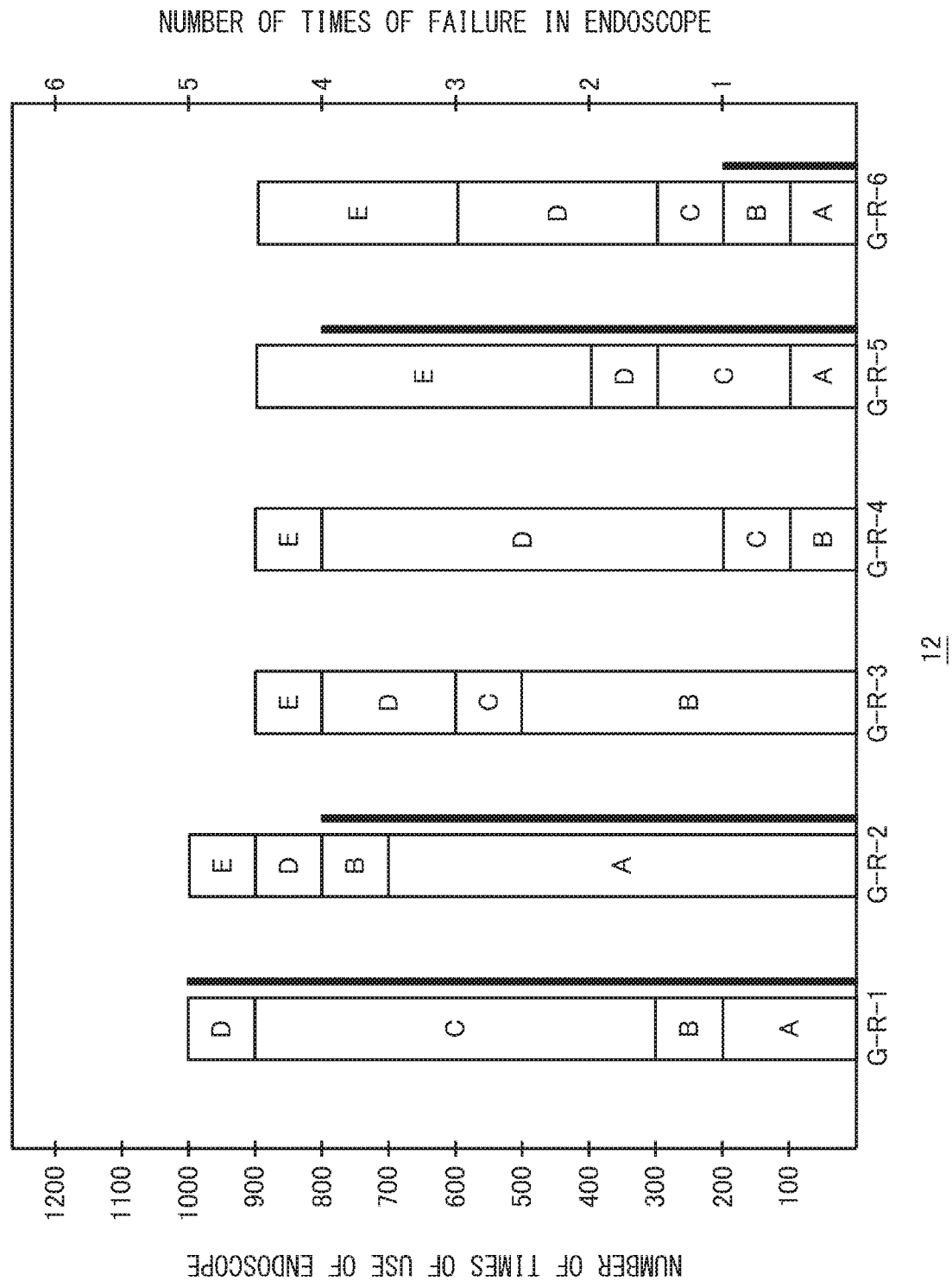
FIG. 34 is a view illustrating one example of usage history information displayed on a terminal device.

FIG. 34 illustrates one example of the usage history information to be displayed on the terminal device 12. This number of times of use graph expresses in graph form the number of times of use table illustrated in FIG. 33. By expressing in graph form in this way, it becomes possible to understand the differences among the usage conditions of the endoscopes 30 at a glance.

In FIGS. 33 and 34, the display processing unit 150 displays the number of times of use of the endoscope 30 for each doctor as the usage history information, but may display, for example, the use time of the endoscope for each doctor as the usage history information. Additionally, the display processing unit 150 may display, for each doctor, the number of times of use or use time of the endoscope 30 used by a doctor.

Example 5

In Example 5, when the scheduling of the endoscope 30 is performed, the processing for assigning cleaning work to a person preparing for examination is performed such that a certain endoscope 30 is cleaned by a specific person preparing for examination as much as possible. By making a set of the cleaning work of the endoscope 30 and a person preparing for examination who cleans it, it can be analyzed that, for example, an endoscope 30, the good condition of which is maintained for a long time, has been skillfully cleaned by a person-in-charge who has frequently experienced cleaning work; on the other hand, it can also be analyzed that an endoscope 30, etc., which is likely to cause a malfunction, is problematically handled in a cleaning step, etc.

Returning to FIG. 3, the assigned person-in-charge information holding unit 230 holds the preferential person-in-charge information on a person-in-charge to whom cleaning work of the endoscope 30 is preferentially assigned. FIG. 35 illustrates a preferential person-in-charge table stored in the assigned person-in-charge information holding unit 230. The preferential person-in-charge table records, for each endoscope 30, preferential person-in-charge information in which the priority of the persons preparing for examination to whom cleaning work is to be assigned (hereinafter, also referred to as a "person-in-charge"). That is, the assigned person-in-charge information holding unit 230 holds, for one endoscope 30, the priority of the person-in-charge to whom cleaning work is to be assigned. In FIG. 35, the "Preferential person-in-charge 1" means a person-in-charge whose assigned priority is No. 1, and the "Preferential person-in-charge 2" a person-in-charge whose assigned priority is No. 2.

For example, for the endoscope G-R-1, the assignment priority of a technician A is set to be No. 1, and that of a technician B to be No. 2. This preferential person-in-charge information is one by which it is designated that when a preferential person-in-charge can be assigned to cleaning work, he/she is preferentially assigned; and a person preparing for examination, who is designated as a preferential person-in-charge, should not necessarily be assigned to the cleaning work of the endoscope. For example, when an examination using the endoscope G-R-1 ends and the endoscope is to be cleaned, and when the technicians A and B are performing other work at the time of cleaning the endoscope, the person-in-charge assignment unit 149 assigns another technician (e.g., technician C) to the cleaning work in order to prevent a delay in cleaning work.

In Example 5, the person-in-charge assignment unit 149 determines a person-in-charge of the cleaning work of an endoscope based on the preferential person-in-charge information held in the assigned person-in-charge information holding unit 230 and the endoscope information managed by the examination schedule management unit 110.

Figure 36:
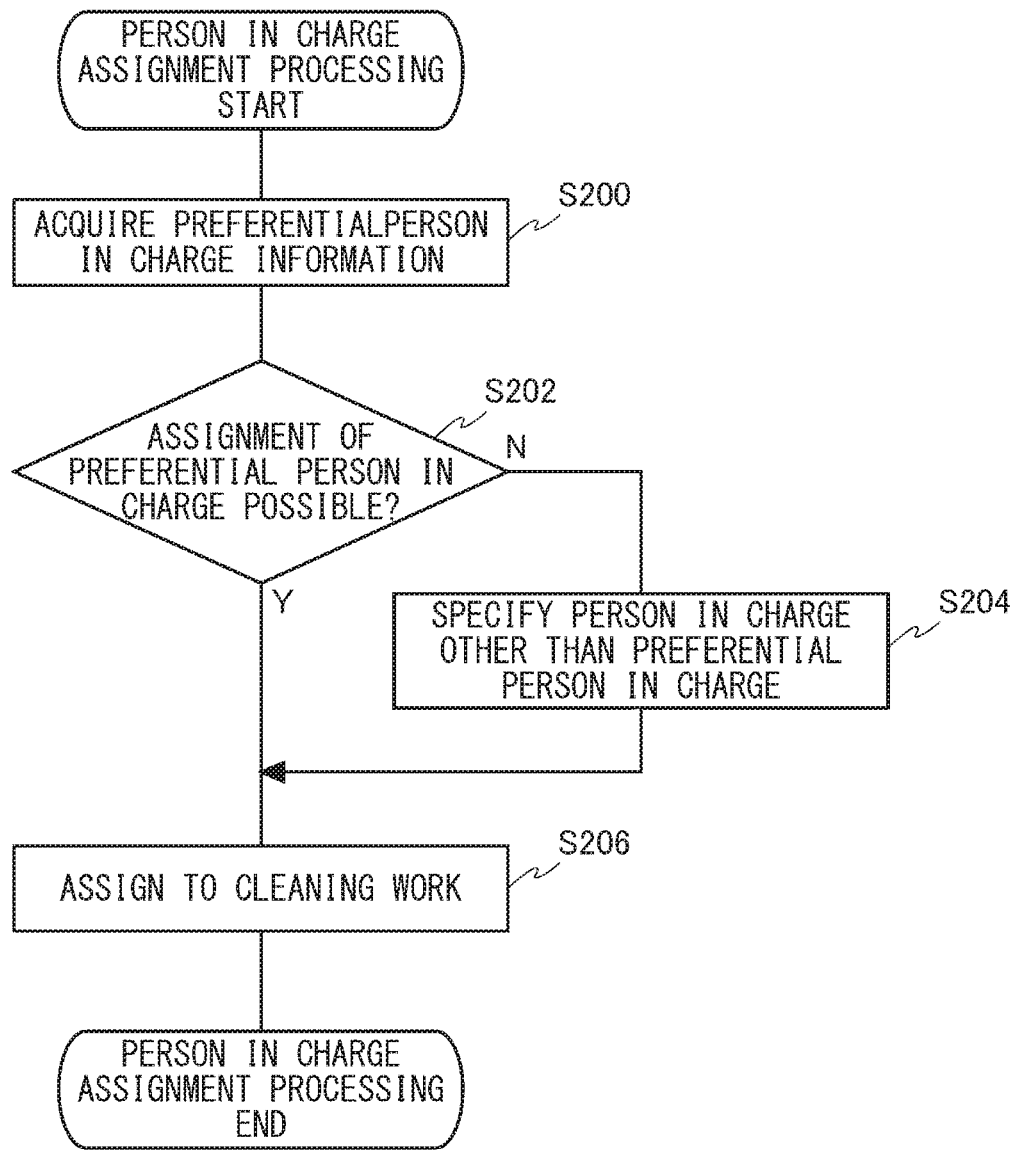
FIG. 36 is a view illustrating a flowchart of person-in-charge assignment processing.

FIG. 36 illustrates a flowchart of person-in-charge assignment processing. The person-in-charge assignment processing illustrated in FIG. 36 is added as processing between S118 and S120 in the cleaning machine assignment processing illustrated in FIG. 13. In the flowchart illustrated in FIG. 13, after the cleaning machine assignment unit 144 assigns the cleaning machine 50 to the used endoscope (S114) and the scheduled cleaning start time and the scheduled cleaning end time are set (S118), the person-in-charge assignment unit 149 acquires the preferential person-in-charge information held in the assigned person-in-charge information holding unit 230 based on the endoscope 30 scheduled to be cleaned (S200).

Hereinafter, an example will be described, in which the endoscopes G-R-3, G-R-1, G-R-5 and C-R-3 are respectively assigned to the examinations E1, E2, E3 and E4 by the endoscope assignment processing described in Example 4.

Figure 37:
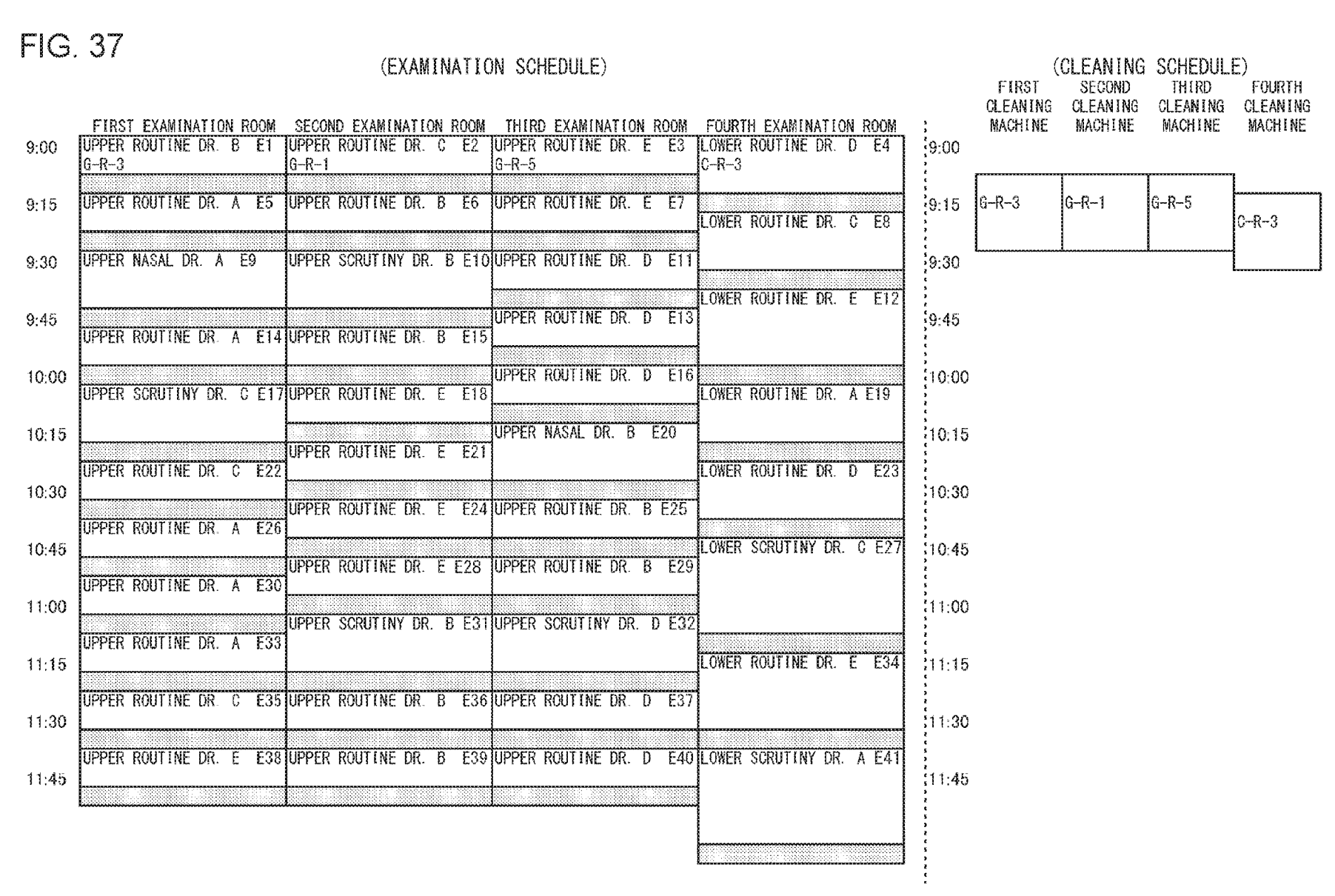

FIG. 37 illustrates a cleaning schedule generated by the cleaning schedule management unit 130. Herein, the results of the assignment by the cleaning machine assignment unit 144 are reflected in the cleaning schedule, and it is specifically registered that between 9:10 and 9:30: the endoscope G-R-3 is cleaned by the first cleaning machine 50a; the endoscope G-R-1 is cleaned by the second cleaning machine 50b; and the endoscope G-R-5 is cleaned by the third cleaning machine 50c, and registered that between 9:15 and 9:35 the endoscope C-R-3 is cleaned by the fourth cleaning machine 50d.

The cleaning schedule management unit 130 of Example 5 manages a cleaning schedule of a plurality of endoscopes, including the cleaning machine 50, information on scheduled cleaning start time, that on scheduled cleaning end time, and person-in-charge of cleaning who take a charge of cleaning work. Hereinafter, a method for registering a person-in-charge of cleaning in the cleaning schedule will be described.

The person-in-charge assignment unit 149 acquires, for each endoscope 30, preferential person-in-charge information from the assigned person-in-charge information holding unit 230, based on the endoscope information assigned to each of the examinations E1, E2, E3, and E4 (S200).

With reference to the preferential person-in-charge table of FIG. 35, the preferential person-in-charge 1 of the endoscope G-R-3 is the technician B, that of the endoscope G-R-1 is the technician A, the preferential person-in-charge of the endoscope G-R-5 is the technician C, and the preferential person-in-charge 1 of the endoscope C-R-3 is the technician C.

With respect to the endoscope G-R-3, the person-in-charge assignment unit 149 determines whether the technician B, preferential person-in-charge 1, can take charge of the cleaning work of the endoscope G-R-3 (S202). In Example 5, the person-in-charge schedule is set for each technician, and the person-in-charge assignment unit 149 determines whether the technician B can take charge of the cleaning work of the endoscope G-R-3 by determining whether there is a vacancy between the scheduled cleaning start time and the scheduled cleaning end time in the person-in-charge schedule. If there is no other work between the scheduled cleaning start time and the scheduled cleaning end time of the endoscope G-R-3, the person-in-charge assignment unit 149 determines that the cleaning work of the endoscope G-R-3 can be assigned to the technician B (S202/Y), and assigns the work to the technician B (S206). If another work is scheduled to be performed either at the scheduled cleaning start time or the scheduled cleaning end time in the person-in-charge schedule, the person-in-charge assignment unit 149 determines that the cleaning work of the endoscope G-R-3 cannot be assigned to the technician B (S202/N). If the work cannot be assigned also to the technician C, preferential person-in-charge 2, the person-in-charge assignment units 149 specifies, of persons-in-charge other than the preferential persons-in-charge, a person-in-charge who does not have work at the time (S204), and assigns the work to this person-in-charge (S206).

Next, with respect to the endoscope G-R-1, the person-in-charge assignment unit 149 determines whether the technician A, preferential person-in-charge 1, can take charge of the cleaning work of the endoscope G-R-1 (S202). When the cleaning work of the endoscope G-R-1 can be assigned to the technician A (S202/Y), the person-in-charge assignment unit 149 assigns the cleaning work of the endoscope G-R-1 to the technician A (S206). If another work is scheduled to be performed either at the scheduled cleaning start time or the scheduled cleaning end time in the person-in-charge schedule, the person-in-charge assignment unit 149 determines that the cleaning work of the endoscope G-R-1 cannot be assigned to the technician A (S202/N). At this time, if the work cannot be assigned also to the technician B, preferential person-in-charge 2, the person-in-charge assignment units 149 specifies, of persons-in-charge other than the preferential persons-in-charge, a person-in-charge who does not have work at the time (S204), and assigns the work to this person-in-charge (S206).

Next, with respect to the endoscope G-R-5, the person-in-charge assignment unit 149 determines whether the technician C, preferential person-in-charge 1, can take charge of the cleaning work of the endoscope G-R-5 (S202). When the cleaning work of the endoscope G-R-5 can be assigned to the technician C (S202/Y), the person-in-charge assignment unit 149 assigns the cleaning work of the endoscope G-R-5 to the technician C (S206). If another work is scheduled to be performed either at the scheduled cleaning start time or the scheduled cleaning end time in the person-in-charge schedule, the person-in-charge assignment unit 149 determines that the cleaning work of the endoscope G-R-5 cannot be assigned to the technician C (S202/N). At this time, if the work cannot be assigned also to the technician B, preferential person-in-charge 2, the person-in-charge assignment units 149 specifies, of persons-in-charge other than the preferential persons-in-charge, a person-in-charge who does not have work at the time (S204), and assigns the work to this person-in-charge (S206).

Next, with respect to the endoscope C-R-3, the person-in-charge assignment unit 149 determines whether the technician C, preferential person-in-charge 1, can take charge of the cleaning work of the endoscope C-R-3 (S202). When the cleaning work of the endoscope C-R-3 can be assigned to the technician C (S202/Y), the person-in-charge assignment unit 149 assigns the cleaning work of the endoscope C-R-3 to the technician C (S206). If another work is scheduled to be performed either at the scheduled cleaning start time or the scheduled cleaning end time in the person-in-charge schedule, the person-in-charge assignment unit 149 determines that the cleaning work of the endoscope C-R-3 cannot be assigned to the technician C (S202/N). At this time, if the work cannot be assigned also to the technician B, preferential person-in-charge 2, the person-in-charge assignment units 149 specifies, of persons-in-charge other than the preferential persons-in-charge, a person-in-charge who does not have work at the time (S204), and assigns the work to this person-in-charge (S206).

When both the preferential person-in-charge 1 and the preferential person-in-charge 2 can be assigned to certain cleaning work, the person-in-charge assignment unit 149 assigns a person-in-charge with higher priority to the cleaning work. The assigned person-in-charge information is notified to the cleaning schedule management unit 130.

FIG. 38 illustrates a cleaning schedule updated by the cleaning schedule management unit 130. When the results of the assignment are notified from the person-in-charge assignment unit 149, the cleaning schedule management unit 130 registers the assigned person-in-charge in the corresponding cleaning processing. Herein, it is registered that: the technician B takes charge of the cleaning work of the endoscope G-R-3: the technician A takes charge of the cleaning work of the endoscope G-R-1; the technician C takes charge of the cleaning work of the endoscope G-R-5; and the technician C takes charge of the cleaning work of endoscope C-R-3. In this way, the cleaning schedule management unit 130 also adds a person-in-charge who performs cleaning work to the cleaning schedule, and records the updated cleaning schedule in the cleaning schedule holding unit 208.

In Example 5, the person-in-charge assignment unit 149 preferentially assigns the cleaning work of a specific endoscope 30 such that a specific person preparing for examination takes charge of the work as much as possible, and hence the cleaning work of the endoscope 30 is performed by the person-in-charge more frequently.

The usage condition monitoring unit 160 monitors the actually performed cleaning processing condition of the endoscope 30, and records it in the history recording unit 232. For example, each cleaning machine 50 is provided with a reading means for reading a person-in-charge ID, so that a person-in-charge performing cleaning work is specified by the person-in-charge causing the reading means to read an ID card, or the like. The usage condition monitoring unit 160 monitors this cleaning processing condition, and the history recording unit 232 records the cleaning history information on the cleaned endoscope 30. With respect to the endoscope 30, the history recording unit 232 records the used cleaning machine 50, information on the date and time when cleaning was performed (cleaning start time, cleaning end time), the person-in-charge who performed cleaning, and the like, by associating them with each other. The history recording unit 232 does not need to record these information as cleaning history information on the endoscope 30, and may record cleaning information in which the used cleaning machine 50, the person-in-charge who performed the cleaning, and the cleaned endoscope 30 are associated with each other, that are managed by the cleaning schedule management unit 130.

The history recording unit 232 also records histories relating to malfunctions and maintenance of the endoscope 30. The above histories may also include, for example, the person-in-charge who worked when a malfunction occurred or maintenance was performed, and information on date and time.

The display processing unit 150 displays, in a comparable format, the cleaning history information on a plurality of the endoscopes 30 recorded in the history recording unit 232. At this time, the display content derivation unit 152 calculates a statistical amount based on the cleaning history information recorded in the history recording unit 232. Herein, the statistical amount means the number of times of cleaning of the endoscope 30, the cleaning time thereof, or the like calculated for each person-in-charge, and the display content derivation unit 152 has the function of deriving the statistical amount in accordance with the contents to be displayed. The display processing unit 150 displays the statistical amount calculated by the display content derivation unit 152.

The period designation unit 154 designates a period for the cleaning history information. This period is specified by an input by a user into an input frame provided on the screen of the terminal device 12. When the period designation unit 154 designate a period, the display content derivation unit 152 extracts the cleaning history information during the period from the history recording unit 232 and calculates the statistical amount to be displayed, and the display processing unit 150 displays the cleaning history information during the designated period, i.e., the statistical amount calculated by the display content derivation unit 152 on the display of the terminal device 12.

FIG. 39 illustrates one example of the cleaning history information to be displayed on the terminal device 12. When a user inputs the period between 2013/11/1 and 2014/10/30 as a display period, the period designation unit 154 designates this period, and the display content derivation unit 152 extracts the cleaning history information during this period from the history recording unit 232. Herein, the display content derivation unit 152 generates a number of times of cleaning table by calculating the number of times of cleaning of an upper routine model for each person-in-charge, and the display processing unit 150 displays it on the display of the terminal device 12. The display content derivation unit 152 may calculate the number of times of malfunctions by generating a list of malfunction histories during this period, and the display processing unit 150 may collectively display the number of times of malfunctions and the malfunction histories.

With this number of times of cleaning table, a user can specify an endoscope that caused less malfunctions and a technician who frequently cleans the endoscope. Conversely, a user can specify an endoscope that caused more malfunctions and a technician who frequently cleans the endoscope. In this way, by the person-in-charge assignment unit 149 preferentially assigning the cleaning work of a specific endoscope to a specific person-in-charge, the information on the histories in which the endoscope 30 was actually cleaned serve as useful information when failure analysis, etc., is performed. Additionally, because the display processing unit 150 displays the cleaning history information on a plurality of the endoscopes 30 in a comparable format, a user can recognize at a glance differences among the usage conditions of the endoscopes 30.

Figure 40:
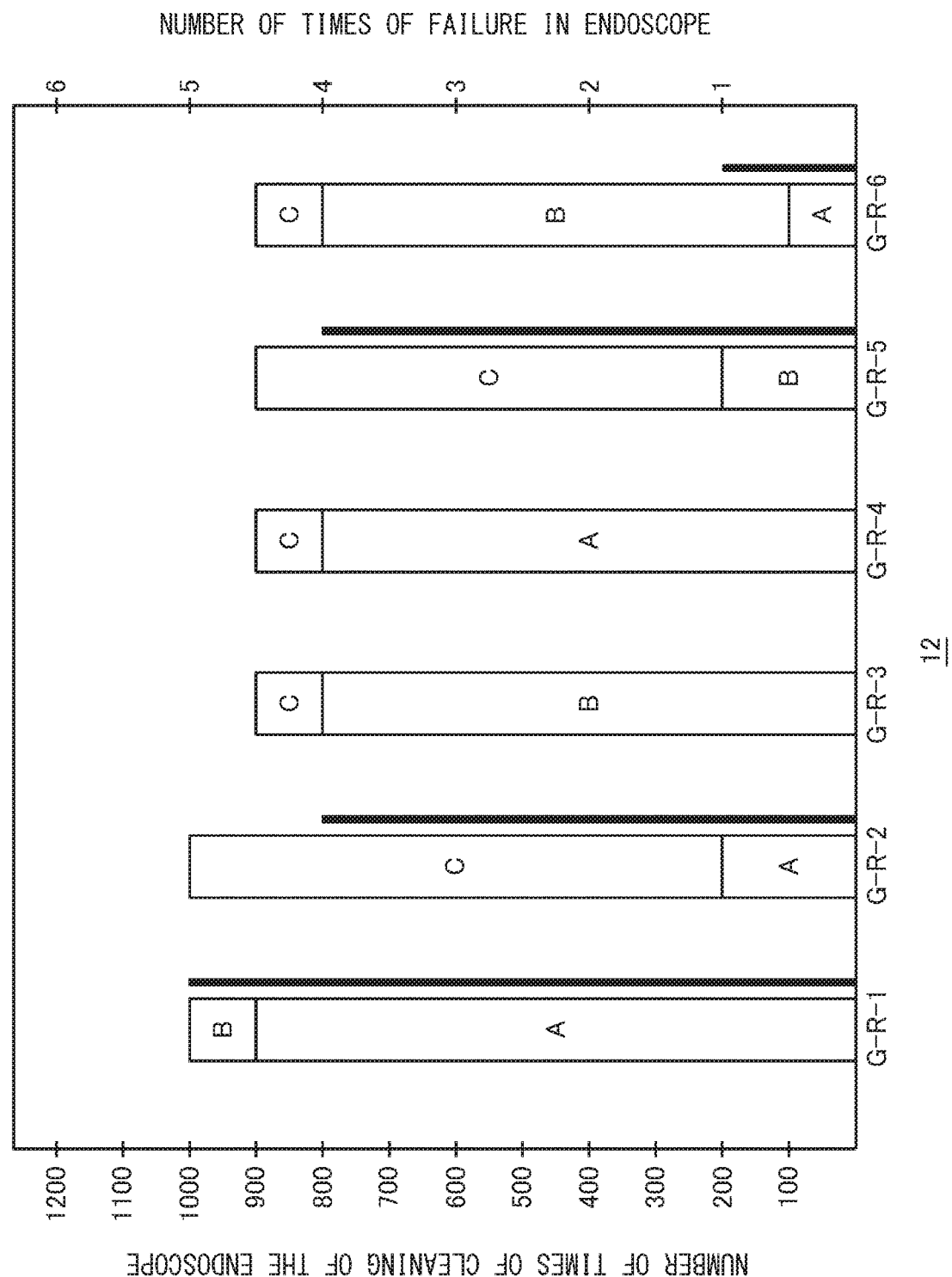
FIG. 40 is a view illustrating one example of cleaning history information displayed on a terminal device.

FIG. 40 illustrates one example of the cleaning history information to be displayed on the terminal device 12. This number of times of cleaning graph expresses in graph form the number of times of cleaning table illustrated in FIG. 39. By expressing in graph form in this way, it becomes possible to understand the differences among the usage conditions of the endoscopes 30 at a glance.

In FIGS. 39 and 40, the display processing unit 150 displays the number of times of cleaning of the endoscope 30 for each person-in-charge as the cleaning history information, but may display, for example, the cleaning time of the endoscope for each person-in-charge as the cleaning history information. Additionally, the display processing unit 150 may display, for each person-in-charge, the number of times of cleaning or cleaning time of the endoscope 30 cleaned by a person-in-charge.

The present invention has been described above based on the embodiment and Examples. It should be understood by those skilled in the art that this embodiment and Examples are described for exemplary purposes only, and that various modifications can be made to combinations of the constituent elements and respective processes, and that such modifications are also within the scope of the present invention. In particular, the use history of an endoscope and the cleaning history thereof are recorded in Examples 4 and 5, respectively, and it is very meaningful to combine both Examples.

In Example 4, it has been described that: with respect to the endoscope 30, the history recording unit 232 records, as endoscope usage information, the examination room where the endoscope 30 was used, doctor who used the endoscope, examination start time, examination end time, identification information on the patient to whom the endoscope was used, examination type information, and the like, by associating them with each other. In Example 5, it has been described that: with respect to the endoscope 30, the history recording unit 232 records, as endoscope cleaning information, the cleaning machine 50 used, cleaning start time, cleaning end time, person-in-charge who cleaned, and the like, by associating them with each other. The history management unit 162 may manage the history of the endoscope 30 based on the endoscope usage information and the endoscope cleaning information that are recorded in the history recording unit 232. Specifically, the history management unit 162 associates the endoscope usage information and the endoscope cleaning information with each other, from both the examination end time of the endoscope 30 included in the endoscope usage information and the cleaning start time of the same endoscope 30 included in the endoscope cleaning information.

For example, when as the endoscope usage information on the endoscope G-R-1, the examination end time is 9:10 on Nov. 6, 2014, and as the endoscope cleaning information, the cleaning start time is 9:12 on Nov. 6, 2014, the history management unit 162 manages the endoscope usage information and the endoscope cleaning information as being associated with each other. Additionally, when as the endoscope cleaning information, the cleaning end time is 9:32 on Nov. 16, 2014, and as the usage information on another endoscope G-R-1, the examination start time is 9: 34, on Nov. 16, 2014, the history management unit 162 manages the endoscope cleaning information and the endoscope usage information by associating with each other. Herein, managing them by associating with each other is equivalent to determining the temporal relationship between the endoscope usage information and the endoscope cleaning information. By managing in this way, the history management unit 162 can manage the history of the endoscope G-R-1, in which: the doctor C used the endoscope G-R-1 to the patient A; then, the technician A cleaned the endoscope G-R-1 by the second cleaning machine; and then, the doctor B used the endoscope G-R-1 to the patient B.

The invention claimed is:

1. An endoscopic examination work support system comprising:
   an examination schedule management unit that manages an examination schedule of a plurality of endoscopic examinations, including an examination room where an endoscopic examination is to be performed, information on scheduled examination start time, that on scheduled examination end time, and examination type information on an examination content of an endoscopic examination;
   an endoscope specification unit that specifies, from a plurality of endoscopes, one or more candidate endoscopes that are available in each endoscopic examination based on examination type information managed by the examination schedule management unit;
   an endoscope assignment unit that assigns, from the one or more candidate endoscopes specified by the endoscope specification unit, an endoscope to each endoscopic examination managed by the examination schedule management unit;
   a cleaning machine assignment unit that assigns, from a plurality of cleaning machines, a cleaning machine for cleaning an endoscope to be used in the each endoscopic examination;
   a cleaning schedule management unit that manages a cleaning schedule of a plurality of endoscopes, including a cleaning machine, information on scheduled cleaning start time, and that on scheduled cleaning end time; and
   a usage condition storage unit that stores past usage condition of a plurality of endoscopes, wherein the past usage condition of each of the plurality of endoscopes comprises information transmitted from the each of the plurality of endoscopes indicating the start time and end time of past examinations performed,
   wherein when there is a plurality of candidate endoscopes specified by the endoscope specification unit, the endoscope assignment unit:
      determines number of times of use in the past and operation time in the past of each of the plurality of candidate endoscopes based on the past usage condition; and
      assigns, from the plurality of candidate endoscopes, an endoscope whose number of times of use in the past is smallest to an endoscopic examination, and when there are a plurality of endoscopes whose numbers of times of use in the past are smallest, assigns an endoscope whose operation time in the past is shortest among them to an endoscopic examination,
   wherein the cleaning machine assignment unit assigns a cleaning machine for cleaning an endoscope, to an endoscope assigned to an endoscopic examination by the endoscope assignment unit, so that a time after a scheduled examination end time of the endoscope becomes a scheduled cleaning start time, and
   wherein the endoscope assignment unit assigns the endoscope to an endoscopic examination, so that a time after a scheduled end time of cleaning by a cleaning machine assigned to the endoscope by the cleaning machine assignment unit becomes a scheduled examination start time.

2. The endoscopic examination work support system according to claim 1, further comprising:
   an endoscope order holding unit that holds priority of a model of an endoscope to be assigned to an examination type of an endoscopic examination, wherein
   the endoscope specification unit specifies an endoscope of a model with high priority.

3. The endoscopic examination work support system according to claim 2, further comprising:
   an endoscope assignment availability confirmation unit that, when the endoscope specification unit specifies an endoscope of a model with low priority and when the endoscope assignment unit assigns the specified endoscope, confirms to a user availability of the endoscope assignment.

4. The endoscopic examination work support system according to claim 1, further comprising:
   a cleaning machine order holding unit that holds priority of a cleaning machine to be assigned to an endoscope, wherein
   the cleaning machine assignment unit assigns a cleaning machine with high priority to an endoscope.

5. The endoscopic examination work support system according to claim 4,
   wherein when there are different models of cleaning machines, the cleaning machine order holding unit holds priority of cleaning machine models.

6. The endoscopic examination work support system according to claim 4,
   wherein the priority of the cleaning machines held in the cleaning machine order holding unit is set based on a medicinal solution to be used in the cleaning machine.

7. The endoscopic examination work support system according to claim 1, further comprising:
   an end time determination unit that determines whether, as a result of assigning a cleaning machine to an endoscope by the cleaning machine assignment unit, a scheduled cleaning end time becomes later than a reference time; and a cleaning machine assignment availability confirmation unit that, when it is determined by the end time determination unit that a scheduled cleaning end time becomes later than the reference time, confirms to a user availability of cleaning machine assignment.

8. The endoscopic examination work support system according to claim 1, further comprising:
a display processing unit that displays a result of assignment of an endoscope by the endoscope assignment unit and/or a result of assignment of a cleaning machine by the cleaning machine assignment unit.

9. The endoscopic examination work support system according to claim 1, further comprising:
a doctor assignment unit that assigns a doctor who performs an examination to the each endoscopic examination managed by the examination schedule management unit.

10. The endoscopic examination work support system according to claim 1, further comprising:
a recording unit that records an examination room where an endoscopic examination managed by the examination schedule management unit was performed, a doctor, a patient, and an endoscope, by associating them with each other.

11. The endoscopic examination work support system according to claim 1, further comprising:
a recording unit that records a cleaning machine by which cleaning managed by the cleaning schedule management unit was performed, a person-in-charge, and an endoscope, by associating them with each other.

12. The endoscopic examination work support system according to claim 1, further comprising:
a recording unit that records both endoscope usage information in which an examination room where an endoscopic examination was performed, examination end time, a doctor, a patient, and an endoscope are associated with each other, and endoscope cleaning information in which a cleaning machine by which cleaning was performed, cleaning start time, a person-in-charge, and an endoscope are associated with each other; and
a history management unit that associates the endoscope usage information and the endoscope cleaning information with each other, from the examination end time of an endoscope included in the endoscope usage information and the cleaning start time of the same endoscope included in the endoscope cleaning information.

13. An endoscopic examination work support method performed by a computer, the endoscope examination work support method comprising:
performing an examination schedule management process of managing an examination schedule of a plurality of endoscopic examinations, including an examination room where an endoscopic examination is to be performed, information on scheduled examination start time, that on scheduled examination end time, and examination type information on an examination content of an endoscopic examination;
performing an endoscope specification process of specifying, from a plurality of endoscopes, one or more candidate endoscopes that are available in each endoscopic examination based on examination type information managed by the examination schedule management process;
performing an endoscope assignment process of assigning, from the one or more candidate endoscopes specified by the endoscope specification process, an endoscope to each endoscopic examination managed by the examination schedule management process;
a cleaning machine assignment process of assigning, from a plurality of cleaning machines, a cleaning machine for cleaning an endoscope to be used in the each endoscopic examination;
a cleaning schedule management process of managing a cleaning schedule of a plurality of endoscopes, including a cleaning machine, information on scheduled cleaning start time, and that on scheduled cleaning end time; and
a usage condition storage process of storing past usage condition of a plurality of endoscopes, wherein the past usage condition of each of the plurality of endoscopes comprises information transmitted from the each of the plurality of endoscopes indicating the start time and end time of past examinations performed,
wherein the endoscope assignment process comprises, when there is a plurality of candidate endoscopes specified by the endoscope specification process:
determining past number of times of use and past use time of each of the plurality of candidate endoscopes specified based on the past usage condition; and
assigning, from the plurality of candidate endoscopes, an endoscope whose past number of times of use is smallest to an endoscopic examination, and when there are a plurality of endoscopes whose past numbers of times of use are smallest, assigns an endoscope whose past use time is shortest among them to an endoscopic examination,
wherein the cleaning machine assignment process comprises assigning a cleaning machine for cleaning an endoscope, to an endoscope assigned to an endoscopic examination by the endoscope assignment process, so that a time after a scheduled examination end time of the endoscope becomes a scheduled cleaning start time, and
wherein the endoscope assignment process comprises assigning the endoscope to an endoscopic examination, so that a time after a scheduled end time of cleaning by a cleaning machine assigned to the endoscope by the cleaning machine assignment process becomes a scheduled examination start time.

* * * * *